US011865177B2

(12) United States Patent
Tomlinson et al.

(10) Patent No.: US 11,865,177 B2
(45) Date of Patent: Jan. 9, 2024

(54) COMPOSITION AND METHODS FOR STABILIZING LIQUID PROTEIN FORMULATIONS

(71) Applicant: Genentech, Inc., South San Francisco, CA (US)

(72) Inventors: Anthony Tomlinson, South San Francisco, CA (US); Barthelemy Luc Demeule, South San Francisco, CA (US); Isidro Angelo Eleazar Zarraga, Millbrae, CA (US)

(73) Assignee: GENENTECH, INC., South San Francisco, CA (US)

(*) Notice: Subject to any disclaimer, the term of this patent is extended or adjusted under 35 U.S.C. 154(b) by 559 days.

(21) Appl. No.: 16/914,100

(22) Filed: Jun. 26, 2020

(65) Prior Publication Data
US 2021/0015920 A1    Jan. 21, 2021

Related U.S. Application Data

(60) Provisional application No. 62/868,615, filed on Jun. 28, 2019.

(51) Int. Cl.
*A61K 39/395* (2006.01)
*A61K 9/08* (2006.01)
*A61K 9/19* (2006.01)
*A61K 47/22* (2006.01)

(52) U.S. Cl.
CPC .......... *A61K 39/39591* (2013.01); *A61K 9/08* (2013.01); *A61K 9/19* (2013.01); *A61K 47/22* (2013.01)

(58) Field of Classification Search
CPC ..... A61K 39/39591; A61K 9/08; A61K 9/107
See application file for complete search history.

(56) References Cited

U.S. PATENT DOCUMENTS

| | | |
|---|---|---|
| 4,399,216 A | 8/1983 | Axel |
| 4,816,567 A | 3/1989 | Cabilly |
| 5,091,178 A | 2/1992 | Hellstrom et al. |
| 5,229,275 A | 7/1993 | Goroff |
| 5,545,806 A | 8/1996 | Lonberg et al. |
| 5,545,807 A | 8/1996 | Surani |
| 5,565,332 A | 10/1996 | Hoogenboom et al. |
| 5,567,610 A | 10/1996 | Borrebaeck |
| 5,569,825 A | 10/1996 | Lonberg |
| 5,571,894 A | 11/1996 | Wels |
| 5,573,905 A | 11/1996 | Lerner |
| 5,587,458 A | 12/1996 | King |
| 5,591,669 A | 1/1997 | Krimpenfort et al. |
| 5,625,126 A | 4/1997 | Lonberg |
| 5,633,425 A | 5/1997 | Lonberg et al. |
| 5,641,870 A | 6/1997 | Rinderknecht |
| 5,661,016 A | 8/1997 | Lonberg et al. |
| 5,731,168 A | 3/1998 | Carter |
| 5,821,337 A | 10/1998 | Carter |
| 5,837,234 A | 11/1998 | Gentile |
| 6,013,605 A | 1/2000 | Rees |
| 6,075,181 A | 6/2000 | Kucherlapati |
| 6,150,584 A | 11/2000 | Kucherlapati |
| 6,982,321 B2 | 1/2006 | Winter |
| 7,087,409 B2 | 8/2006 | Barbas, III |

FOREIGN PATENT DOCUMENTS

| | | | |
|---|---|---|---|
| CN | 108421046 A | * | 8/2018 |
| WO | 198905859 A1 | | 6/1989 |
| WO | 199308829 A1 | | 5/1993 |
| WO | 199404690 A1 | | 3/1994 |
| WO | 199616673 A1 | | 6/1996 |
| WO | 199627011 A1 | | 9/1996 |
| WO | 199717852 A1 | | 5/1997 |
| WO | 2011089062 A2 | | 7/2011 |
| WO | 2011089062 A3 | | 3/2012 |
| WO | 2014096051 A1 | | 6/2014 |
| WO | 2017117311 A1 | | 7/2017 |

OTHER PUBLICATIONS

Stability of IgG1 Monoclonal Antibodies in Intravenous Infusion Bags Under Clinical In-Use Conditions Alavattam Sreedharazephania Kwong Glovernicole Pirosnina Xiaoankit Patelbruce Kabakoff Wiley Online Library (wileyonlinelibrary.com). DOI 10.1002/jps.22739 (Year: 2016).*
Effect of Polysorbate 20 and Polysorbate 80 on the Higher-Order Structure of a Monoclonal Antibody and Its Fab and Fc Fragments Probed Using 2D Nuclear Magnetic Resonance Spectroscopy Singh et al. Journal of Pharmaceutical Sciences 106 (2017) 3486-3498 (Year: 2017).*
Freeze Drying Protein Formulations Adeline Siew, PhD Pharmaceutical Technology May 2, 2014, vol. 38, Issue 5 (Year: 2014).*
Polysorbates 20 and 80 Used in the Formulation of Protein Biotherapeutics: Structure and Degradation Pathways Bruce A. Kerwin Journal of Pharmaceutical Sciences, vol. 97, No. 8, Aug. 2008 (Year: 2008).*
Characterization and Stability Study of Polysorbate 20 in Therapeutic Monoclonal Antibody Formulation by Multidimensional Ultrahigh Performance Liquid Chromatography—Charged Aerosol Detection—Mass Spectrometry Li et al. dx.doi.org/10.1021/ac5009628 | Anal. Chem. 2014, 86, 5150-5157 (Year: 2014).*
Boerner, P. et al. (Jul. 1, 1991). "Production of Antigen-Specific Human Monoclonal Antibodies From in Vitro-Primed Human Splenocytes," J. Immunol. 147(1):86-95.
Brennan, M. et al. (Jul. 5, 1985). "Preparation of Bispecific Antibodies by Chemical Recombination of Monoclonal Immunoglobulin G1 Fragments," Science 229:81-83.

(Continued)

*Primary Examiner* — Jeffrey S Lundgren
*Assistant Examiner* — Eric Tran
(74) *Attorney, Agent, or Firm* — MORRISON & FOERSTER LLP

(57) ABSTRACT

The present disclosure provides liquid formulations comprising polypeptides and surfactants. In particular, it discloses a liquid formulation comprising a polypeptide and a surfactant, wherein at least about 70% (wt %) of the surfactant are isosorbide polyoxyethylene (POE) fatty acid esters. The invention also provides methods for making such liquid formulations, articles of manufacture comprising such liquid formulations and methods of treating a patient with such liquid formulations.

35 Claims, 25 Drawing Sheets

(56) References Cited

OTHER PUBLICATIONS

Brodeur, B.R. et al. (1987). "Mouse-Human Myeloma Partners for the Production of Heterohybridomas," Chapter 4 in Monoclonal Antibody Production Techniques and Applications, Marcel Dekker, Inc. New York, New York, pp. 51-63.

Brüggermann, M. et al. (1993). "Designer Mice: The Production Of Human Antibody Repertoires In Transgenic Animals," Year Immunology 7:33-40.

Carter, P. et al. (Feb. 1992). "High Level *Escherichia coli* Expression and Production of a Bivalent Humanized Antibody Fragment," Bio/Technology 10:163-167.

Carter, P. et al. (May 1992). "Humanization of An Anti-p185HER2 Antibody For Human Cancer Therapy," Proc. Natl. Acad. Sci. USA 89:4285-4289.

Chothia, C. et al. (1987). "Canonical Structures for the Hypervariable Regions of Immunoglobulins," J. Mol. Biol. 196:901-917.

Clackson, T. et al. (Aug. 15, 1991) "Making Antibody Fragments Using Phage Display Libraries," Nature 352:624-628.

Cole, S.P.C. et al. (1985). "The EBV-Hybridoma Technique and its Application to Human Lung Cancer," Monoclonal Antibodies and Cancer Therapy, Alan R. Liss, Inc., New York, New York, pp. 77-96.

Fishwild et al. (Jul. 1996). "High-avidity human IgGK Monoclonal Antibodies from a Novel Strain of Minilocus Transgenic Mice," Nature Biotechnol. 14:845-851.

Goding, J.W. (1986). "Production of Monoclonal Antibodies," Chapter 3 in Monoclonal Antibodies: Principles and Practice, Academic Press, New York, pp. 59-103.

Graham, F.L. et al. (1973) "A New Technique for the Assay of Infectivity of Human Adenovirus 5 DNA," Virology 52:456-467.

Griffiths, A.D. et al. (1993). "Human Anti-Self Antibodies with High Specificity from Phage Display Libraries," Embo J, 12(2):725-734.

Gruber, M. et al. (1994). "Efficient Tumor Cell Lysis Mediated by a Bispecific Single Chain Antibody Expressed in *Escherichia coli*," J. Immunol. 152:5368-5374.

Harris, W.J. (1995). "Production of Humanized Monoclonal and Antibodies for in vivo Imaging and Therapy," Biochem. Soc. Transactions 23:1035-1038.

Hollinger, P. et al. (Jul. 1993). "Diabodies: Small Bivalent And Bispecific Antibody Fragments," Proc. Natl. Acad. Sci. USA 90:6444-6448.

Hoogenboom, ¬H.R et al. (Sep. 1991). "By-Passing Immunisation: Human Antibodies from Synthetic Repertoires of Germline VH Gene Segments Rearranged in vitro," Journal of Molecular Biology 227(2):381-388.

Hurle, M.R. et al. (1994). "Protein Engineering Techniques for Antibody Humanization," Curr. Op. Biotech. 5(4):428-433.

Jakobovits, A. et al. (Mar. 18, 1993). "Germ-Line Transmission and Expression of a Human-Derived Yeast Artificial Chromosome," Nature 362:255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.

Johnson, K.S. et al. (1993). "Human Antibody Engineering," Current Opinion in Structural Biology 3:564-571.

Jones, A.J.S. (1993). "Analysis of Polypeptides and Proteins," Adv. Drug Delivery Rev. 10:29-90.

Jones, P.T. et al. (May 29, 1986). "Replacing the Complementarity-Determining Regions in a Human Antibody With Those From a Mouse," Nature 321:522-525.

Kohler, G. et al. (Aug. 7, 1975) "Continuous Cultures Of Fused Cells Secreting Antibody Of Predefined Specificity," Nature 256:495-497.

Kostelny, S.A. et al. (Mar. 1, 1992). "Formation of a Bispecific Antibody By The Use of Leucine Zippers," J. Immunol. 148(5):1547-1553.

Kozbor, D. (Dec. 1984). "A Human Hybrid Myeloma for Production of Human Monoclonal Antibodies," J. Immunol. 133(6):3001-3005.

Levine, R.L. et al. (Dec. 1996) "Methionine Residues as Endogenous Antioxidants in Proteins," Proceedings of the National Academy of Sciences of the United States of America vol. 93(26):15036-15040.

Li, J. et al. (Mar. 7, 2006). "Human Antibodies for Immunotherapy Development Generated via a Human B Cell Hybridoma Technology," Proc. Natl. Acad. Sci. USA 103:3557-3562, 6 pages.

Lonberg, N. et al. (Apr. 28, 1994). "Antigen-Specific Human Antibodies From Mice Comprising Four Distinct Genetic Modifications," Nature 368:856-859.

Lonberg, N. et al. (1995). "Human Antibodies From Transgenic Mice," Intern. Rev. Immunol. 13:65-93.

Marks, J.D. et al. (1991). "By-Passing Immunization Human Antibodies from V-gene Libraries Displayed on Phage," J. Mol. Biol. 222:581-597.

Marks, J.D. et al. (Jul. 1992). "By-Passing Immunization: Building High Affinity Human Antibodies by Chain Shuffling," Bio/Technology 10:779-783.

Mccafferty, J. et al. (Dec. 6, 1990). "Phage Antibodies: Filamentous Phage Displaying Antibody Variable Domains," Nature 348:552-554.

Milstein, C. et al., (Oct. 6, 1983) "Hybrid Hybridomas and their use in Immunohistochemistry," Nature 305:537-540.

Morimoto, K. et al. (1992). "Single-Step Purification of F(AB')2 Fragments of Mouse Monoclonal Antibodies (Immunoglobulins G1) By Hydrophobic Interaction High Performance Liquid Chromatography Using TSKgel Phenyl-5PW," J. Biochem. Biophys. Method 24:107-117.

Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.

Morrison, S.L. (Apr. 28, 1994). "Success in Specification," Nature 368:812-813.

Munson, P.J. et al. (1980). "Ligand: A Versatile Computerize Approach for Characterization of Ligand-Binding Systems," Anal. Biochem. 107:220-239.

Neuberger, M. (Jul. 1996). "Generating High-Avidity Human Mabs in Mice," Nature Biotechnol. 14:826.

Plückthun, A. (1992). "Mono- and Bivalent Antibody Fragments Produced in *Escherichia coli*: Engineering, Folding and Antigen Binding," Immunol. Revs. 130:151-188.

Presta, L.G. (1992). "Antibody Engineering," Current Opinion in Structural Biology 2:593-596.

Presta, L.G. et al. (Sep. 1, 1993). "Humanization of an Antibody Directed Against IgE," J. Immunol. 151(5):2623-2632.

Riechmann, L. et al. (Mar. 24, 1988). "Reshaping Human Antibodies For Therapy," Nature 332:323-329.

Shalaby, M.R. et al. (Jan. 1, 1992). "Development of Humanized Bispecific Antibodies Reactive With Cytotoxic Lymphocytes and Tumor Cells Overexpressing the HER2 Protooncogene," J. Exp. Med. 175:217-225.

Shaw, C.H. et.al. (Sep. 1983). "A General Method for the Transfer of Cloned Genes to Plant Cells," Gene 23(3):315-330.

Sims, M.J. et al. (Aug. 15, 1993) "A Humanized CD18 Antibody Can Block Function without Cell Destruction," The Journal of Immunology 151(4):2296-2308.

Skerra, A. (1993). "Bacterial Expression of Immunoglobulin Fragments," Curr. Opinion in Immunol. 5:256-262.

Suresh, M.R. et al. (1986). "Bispecific Monoclonal Antibodies From Hybrid Hybridomas," Methods in Enzymology 121:210-228, 19 pages.

Traunecker, A. et al. (1991). "Bispecific Single Chain Molecules (Janusins) Target Cytotoxic Lymphocytes on HIV Infected Cells," EMBO J. 10(12):3655-3659.

Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.

Van Dijk, M.A. et al. (Aug. 2001). "Human Antibodies as Next Generation Therapeutics," Curr. Opin. Pharmacol. 5(4):368-374.

(56) References Cited

OTHER PUBLICATIONS

Vaswani, S.K. et al. (Aug. 1998). "Humanized Antibodies as Potential Therapeutic Drugs," Ann. Allergy, Asthma & Immunol. 1:105-115.
Verhoeyen, M. et al. (Mar. 25, 1988). "Reshaping Human Antibodies: Grafting an Antilysozyme Activity," Science 239:1534-1536.
Waterhouse, P. et al. (1993). "Combinatorial Infection and in Vivo Recombination: a Strategy for Making Large Phage Antibody Repertoires," Nucl. Acids Res. 21(9):2265-2266.
Borisov, O.V. et al. (2011, e-pub. Apr. 27, 2011). "Toward Understanding Molecular Heterogeneity of Polysorbates by Application of Liquid Chromatography—Mass Spectrometry With Computer-Aided Data Analysis," Analytical Chemistry 83(10):3934-3942.
International Preliminary Report on Patentability, dated Dec. 28, 2021, for International Application No. PCT/US2020/039827, filed Jun. 26, 2020, 8 pages.
International Search Report and Written Opinion, dated Oct. 15, 2020, for International Application No. PCT/US2020/039827, filed Jun. 26, 2020, 15 pages.
Jones, M.T. et al. (2018). "Considerations for the Use of Polysorbates in Biopharmaceuticals." Pharmaceutical Research 35(8):148, 8 pages.
Kishore, R.S. K. et al. (2011, e-pub. Mar. 3, 2011) "The Degradation of Polysorbates 20 and 80 and its Potential Impact on the Stability of Biotherapeutics," Pharm. Res. 28(5):1194-1210.
Lippold, S. et al. (2017, e-pub. Sep. 26, 2016). "Impact of Mono- and Poly-ester Fractions on Polysorbate Quantitation Using Mixed-Mode HPCL-CAD/ELSD and the Fluorescence Micelle Assay," Journal of Pharmaceutical and Biomedical Analysis 132:24-34.

* cited by examiner

COMPOSITION AND METHODS FOR STABILIZING LIQUID PROTEIN FORMULATIONS

CROSS-REFERENCE TO RELATED APPLICATIONS

This application claims the priority benefit of U.S. Provisional Application No. 62/868,615, filed Jun. 28, 2019, which is incorporated herein by reference in its entirety.

FIELD OF THE INVENTION

The present disclosure relates generally to stable liquid pharmaceutical formulations comprising polypeptides and surfactants and methods for making the same.

BACKGROUND

Polysorbates (PS), which are commonly used surfactants in biopharmaceutical protein formulations, have been shown to be susceptible to a variety of degradation pathways including: chemical hydrolysis, oxidation, and enzymatic hydrolysis. The degradation of PS can lead to the generation of various peroxides which subsequently oxidize amino acid residues (e.g., methionine) in the protein during long-term storage. Levine et al. *Proc. Nat. Acad. Sci. U.S.A* (1996) 93, 15036-15040. The oxidation of these amino acid residues has potentially negative impact on the biological activity of the protein, thereby limiting the protective effect of PS in protein formulations. In addition, because polysorbates are heterogeneous mixtures, the patterns of the degradation can be strikingly different between the different pathways. Therefore, there remains a need for a more efficient excipient for a surfactant in the development of pharmaceutical protein formulations.

SUMMARY OF THE INVENTION

The present disclosure provides a liquid formulation comprising a polypeptide and a surfactant, wherein at least about 70% (wt %) of the surfactant are isosorbide polyoxyethylene (POE) fatty acid esters. In some embodiments, the isosorbide POE fatty acid esters comprise about 5-30 POE units. In some embodiments, the isosorbide POE fatty acid esters comprise about 20 POE units. In some embodiments, the isosorbide POE fatty acid esters comprise fatty acid chains selected from the group consisting of an optionally substituted $C_{4-28}$ alkyl and an optionally substituted $C_{4-28}$ alkenyl. In some embodiments, the isosorbide POE fatty acid esters are monoesters, diesters, or a mixture of the foregoing. In some embodiments, the isosorbide POE fatty acid esters are selected from the group consisting of isosorbide POE monolaurate, isosorbide POE monomyristate, isosorbide POE monopalmitate, isosorbide POE monostearate, and isosorbide POE monooelate.

In some embodiments, the isosorbide POE fatty acid ester is a compound of Formula (I):

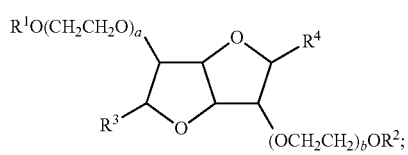

wherein:
a and b are independently integers from 2 to 28, provided that the sum of a and b is an integer from 5-30;
$R^1$ and $R^2$ are independently selected from the group consisting of hydrogen and —C(O)R", wherein R" is an optionally substituted $C_{3-27}$ alkyl or an optionally substituted $C_{3-27}$ alkenyl; and
$R^3$ and $R^4$ are independently hydrogen.

In some embodiments, the sum of a and b is 5, 6, 7, 8, 9, 10, 11, 12, 13, 14, 15, 16, 17, 18, 19, 20, 21, 22, 23, 24, or 25. In some embodiments, the sum of a and b is 9. In some embodiments, the sum of a and b is 20. In some embodiments, $R^1$ is H and $R^2$ is —C(O)R". In some embodiments, $R^2$ is H and $R^1$ is —C(O)R". In some embodiments, both $R^1$ and $R^2$ are —C(O)R". In some embodiments, R" is an unsubstituted $C_{3-27}$ alkyl. In some embodiments, R" is an unsubstituted $C_{11}$ alkyl. In some embodiments, R" is an unsubstituted $C_{3-27}$ alkenyl. In some embodiments, R" is an unsubstituted $C_{17}$ alkenyl.

In some embodiments, the surfactant further comprises POE fatty acid esters. In some embodiments, at least about 80% (wt %) of the surfactant are isosorbide POE fatty acid esters and POE fatty acid esters. In some embodiments, at least about 85%, at least about 90% or at least about 95% (wt %) of the surfactant are isosorbide POE fatty acid esters and POE fatty acid esters. In some embodiments, at least about 90% (wt %) of the surfactant are isosorbide POE fatty acid esters and POE fatty acid esters. In some embodiments, the POE fatty acid ester comprises a fatty acid chains selected from the group consisting of an optionally substituted $C_{4-28}$ alkyl and an optionally substituted $C_{4-28}$ alkenyl. In some embodiments, the POE fatty acid ester is selected from a group consisting of POE monolaurate, POE monomyristate, POE monopalmitate, POE monostearate, and POE monooelate. In some embodiments, less than about 20% of the surfactant are POE fatty acid esters. In some embodiments, less than about 10% of the surfactant are POE fatty acid esters. In some embodiments, the surfactant is about 0.0005% to 0.2% (w:v) in the liquid formulation. In some embodiments, the surfactant comprises a greater amount of isosorbide POE fatty acid esters than POE fatty acid esters. In some embodiments, the surfactant further comprises a sorbitan POE fatty acid ester. In some embodiments, less than about 10%, less than about 8%, less than about 5%, less than about 3% or less than about 1% of the surfactant are sorbitan POE fatty acid esters.

In some embodiments, the polypeptide is a protein. In some embodiments, the protein is an antibody selected from a group consisting of a polyclonal antibody, a monoclonal antibody, a humanized antibody, a human antibody, a chimeric antibody, and an antibody fragment. In some embodiments, the antibody fragment is selected from the group consisting of Fab, Fab', F(ab')2, and Fv fragments. In some embodiments, the antibody concentration is about 0.001 mg/mL to about 300 mg/mL. In some embodiments, the liquid formulation is a reconstituted lyophilized formulation. In some embodiments, the liquid formulation is further diluted with an infusion solution to a concentration of about 0.001 mg/mL to about 100 mg/mL. In some embodiments, the liquid formulation is substantially free of aggregates. In some embodiments, the liquid formulation comprises less free fatty acid particle formation.

Also provided herein is an article of manufacture comprising a container enclosing any liquid formulation described herein. In some embodiments, the container is an IV bag. In some embodiments, the IV bag comprises an injection device. In some embodiments the IV bag comprises an infusion solution. Also provided here is a lyophilized formulation comprising a polypeptide and a surfactant, wherein at least about 70% (wt %) of the surfactant are isosorbide POE fatty acid esters and POE fatty acid esters. In some embodiments, the lyophilized formulation is prepared by lyophilizing any liquid formulation disclosed herein.

Also provided herein is a method of making a liquid formulation comprising adding a polypeptide and a surfactant to an aqueous solution, wherein at least 70% (wt %) of the surfactant are isosorbide POE fatty acid esters. In some embodiments, the isosorbide POE fatty acid esters comprise about 5-30 POE units. In some embodiments, the isosorbide POE fatty acid esters comprise about 20 POE units. In some embodiments, the isosorbide POE fatty acid esters comprise fatty acid chains selected from the group consisting of an optionally substituted $C_{4-28}$ alkyl and an optionally substituted $C_{4-28}$ alkenyl. In some embodiments, the isosorbide POE fatty acid esters are monoesters, diesters, or a mixture of the foregoing. In some embodiments, the isosorbide POE fatty acid esters are selected from the group consisting of isosorbide POE monolaurate, isosorbide POE monomyristate, isosorbide POE monopalmitate, isosorbide POE monostearate, and isosorbide POE monooelate.

In some embodiments, the isosorbide POE fatty acid ester is a compound of Formula (I):

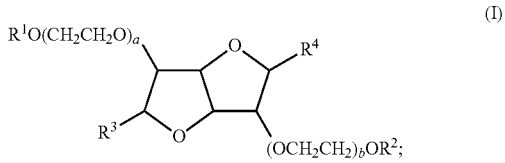

wherein:
a and b are independently integers from 2 to 28, provided that the sum of a and b is an integer from 5-30;
$R^1$ and $R^2$ are independently selected from the group consisting of hydrogen and —C(O)R", wherein R" is an optionally substituted $C_{3-27}$ alkyl or an optionally substituted $C_{3-27}$ alkenyl; and
$R^3$ and $R^4$ are independently hydrogen.

In some embodiments, the sum of a and b is 5, 6, 7, 8, 9, 10, 11, 12, 13, 14, 15, 16, 17, 18, 19, 20, 21, 22, 23, 24, or 25. In some embodiments, the sum of a and b is 9. In some embodiments, the sum of a and b is 20. In some embodiments, $R^1$ is H and $R^2$ is —C(O)R". In some embodiments, $R^2$ is H and $R^1$ is —C(O)R". In some embodiments, both $R^1$ and $R^2$ are —C(O)R". In some embodiments, R" is an unsubstituted $C_{3-27}$ alkyl. In some embodiments, R" is an unsubstituted $C_{11}$ alkyl. In some embodiments, R" is an unsubstituted $C_{3-27}$ alkenyl. In some embodiments, R" is an unsubstituted $C_{17}$ alkenyl.

In some embodiments, the surfactant further comprises POE fatty acid esters. In some embodiments, at least about 80% (wt %) of the surfactant are isosorbide POE fatty acid esters and POE fatty acid esters. In some embodiments, at least about 85%, at least about 90% or at least about 95% (wt %) of the surfactant are isosorbide POE fatty acid esters and POE fatty acid esters. In some embodiments, the method further comprises adding a POE fatty acid ester. In some embodiments, the POE fatty acid ester comprises a fatty acid chains selected from the group consisting of an optionally substituted $C_{4-28}$ alkyl and an optionally substituted $C_{4-28}$ alkenyl. In some embodiments, the POE fatty acid ester is selected from a group consisting of POE monolaurate, POE monomyristate, POE monopalmitate, POE monostearate, and POE monooelate. In some embodiments, less than about 20% of the surfactant are POE fatty acid esters. In some embodiments, less than about 10% of the surfactant are POE fatty acid esters. In some embodiments, the surfactant is about 0.0005% to 0.2% (w:v) in the liquid formulation. In some embodiments, the surfactant comprises a greater amount of isosorbide POE fatty acid esters than POE fatty acid esters. In some embodiments, the surfactant further comprises sorbitan POE fatty acid esters. In some embodiments, less than about 10%, less than about 8%, less than about 5%, less than about 3% or less than about 1% of the surfactant are sorbitan POE fatty acid esters.

In some embodiments, the polypeptide is a protein. In some embodiments, the protein is an antibody selected from a group consisting of a polyclonal antibody, a monoclonal antibody, a humanized antibody, a human antibody, a chimeric antibody, and an antibody fragment. In some embodiments, the antibody fragment is selected from the group consisting of Fab, Fab', F(ab')2, and Fv fragments. In some embodiments, the antibody concentration is about 0.1 mg/mL to about 300 mg/mL. In some embodiments, the liquid formulation is a reconstituted lyophilized formulation. In some embodiments, the liquid formulation is further diluted with an infusion solution to a concentration of about 0.1 mg/mL to about 2 mg/mL. In some embodiments, the liquid formulation is further lyophilized to prepare a lyophilized formulation. In some embodiments, the liquid formulation is substantially free of aggregates. In some embodiments, the liquid formulation comprises less free fatty acid particle formation.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION

Figure 1A:
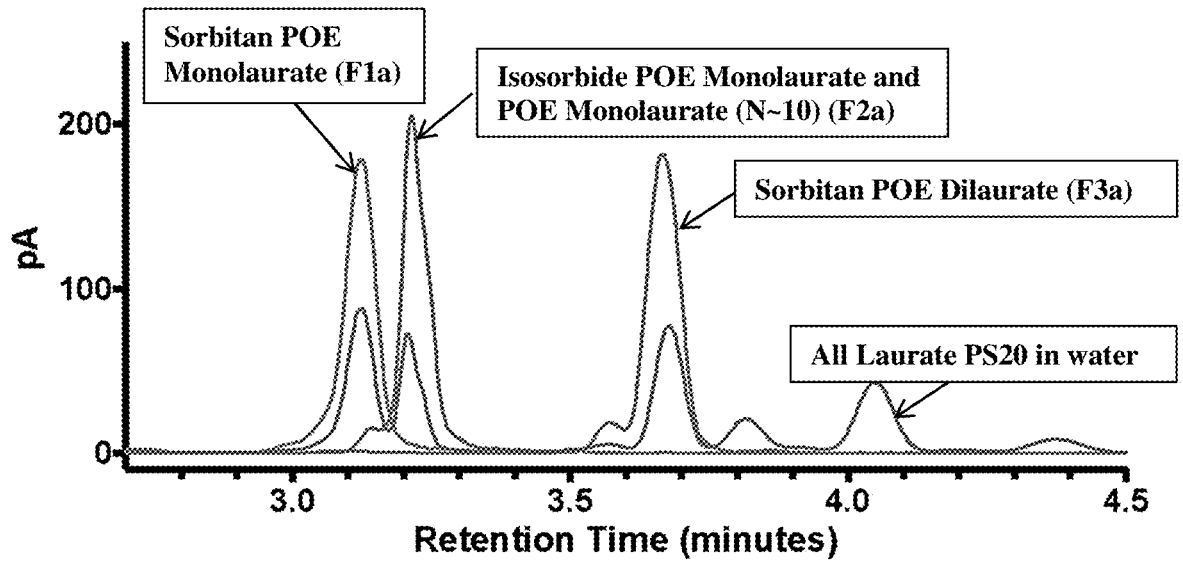
FIGS. 1A and 1B show the UPLC analysis for purity and identity of polysorbate 20 fractions (FIG. 1A) and polysorbate 80 fractions (FIG. 1B).

The present disclosure is based on the discovery that particular fractions of polysorbates provide strong protective effects in pharmaceutical protein formulations. Specifically, they allow usage of less surfactant for the same protective effect, thereby minimizing the negative impact on the biological activity of proteins resulted from degradation of polysorbates. In one aspect, the present disclosure provides a protein formulation comprising one or more such fractions of polysorbates. The protein formulations described herein have demonstrated increased protein stability in formulations. The description also provides kits and methods for making protein formulations.

I. Definitions

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to particular method steps, reagents, or conditions are specifically embraced by the present disclosure and are disclosed herein just as if each and every combination was individually and explicitly disclosed.

As used herein and in the appended claims, the singular forms "a," "an," and "the" include plural referents unless the context clearly dictates otherwise.

Reference to "about" a value or parameter herein includes (and describes) variations that are directed to that value or parameter per se. For example, description referring to "about X" includes description of "X".

The term "pharmaceutical formulation" refers to a preparation which is in such form as to permit the biological activity of the active ingredient to be effective, and which contains no additional components which are unacceptably toxic to a subject to which the formulation would be administered. In some embodiments, the formulations are sterile.

A "reconstituted" formulation is one which has been prepared by dissolving a lyophilized protein or antibody formulation in a diluent such that the protein is dispersed in the reconstituted formulation. The reconstituted formulation is suitable for administration (e.g., parenteral administration) to a patient to be treated with the protein of interest and, in certain embodiments of the invention, may be one which is suitable for subcutaneous administration.

The terms "protein" "polypeptide" and "peptide" are used herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Typically, a protein for use herein will have a molecular weight of at least about 5-20 kD, alternatively at least about 15-20 kD, or at least about 20 kD. Also included within the definition are, for example, proteins containing one or more analogs of an amino acid (including, for example, unnatural amino acids, etc.), as well as other modifications known in the art. Examples of proteins encompassed within the definition herein include mammalian proteins, such as, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; leptin; clotting factors such as factor VIIIC, factor IX, tissue factor, and von Willebrands factor; anti-clotting factors such as Protein C;

atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; a tumor necrosis factor receptor such as death receptor 5 and CD120; TNF-related apoptosis-inducing ligand (TRAIL); B-cell maturation antigen (BCMA); B-lymphocyte stimulator (BLyS); a proliferation-inducing ligand (APRIL); enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; platelet-derived endothelial cell growth factor (PD-ECGF); a vascular endothelial growth factor family protein (e.g., VEGF-A, VEGF-B, VEGF-C, VEGFD, and PlGF); a platelet-derived growth factor (PDGF) family protein (e.g., PDGF-A, PDGF-B, PDGF-C, PDGF-D, and dimers thereof); fibroblast growth factor (FGF) family such as aFGF, bFGF, FGF4, and FGF9; epidermal growth factor (EGF); receptors for hormones or growth factors such as a VEGF receptor(s) (e.g., VEGFR1, VEGFR2, and VEGFR3), epidermal growth factor (EGF) receptor(s) (e.g., ErbB1, ErbB2, ErbB3, and ErbB4 receptor), platelet-derived growth factor (PDGF) receptor(s) (e.g., PDGFR-α and PDGFR-β), and fibroblast growth factor receptor(s); TIE ligands (Angiopoietins, ANGPT1, ANGPT2); Angiopoietin receptor such as TIE1 and TIE2; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CDS, CD19 and CD20; erythropoietin; osteoinductive factors; immunotoxins; a bone morphogenetic protein (BMP); a chemokine such as CXCL12 and CXCR4; an intelferon such as interferon-alpha, -beta, and -gamma; colony stimulating factors (CSFs), e.g., M-CSF, GM-CSP, and G-CSF; a cytokine such as interleukins (ILs), e.g., IL-1 to IL-10; midkine; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; ephrins; Bv8; Delta-like ligand 4 (DLL4); Del-1; BMP9; BMP10; Follistatin; Hepatocyte growth factor (HGF)/scatter factor (SF); Alk1; Robo4; ESM1; Perlecan; EGF-like domain, multiple 7 (EGFL7); CTGF and members of its family; thrombospondins such as thrombospondin1 and thrombospondin2; collagens such as collagen IV and collagen XVIII; neuropilins such as NRP1 and NRP2; Pleiotrophin (PTN); Progranulin; Proliferin; Notch proteins such as Notch1 and Notch4; semaphorins such as Sema3A, Sema3C, and Sema3F; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to one or more protein, including, for example, any of the above-listed proteins.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fe region.

"Antibody fragments" comprise a portion of an intact antibody, optionally comprising the antigen binding region thereof. Examples of antibody fragments include Fab, Fab', F(ab')2, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see e.g., U.S. Pat. No. 4,816,567; and Morrison et al., *Proc. Natl. Acad. Sci. U.S.A.* 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fe), typically that of a human immunoglobulin. For further details, see e.g., Jones et al., *Nature* 321:522-525 (1986); Riechmann et al., *Nature* 332:323-329 (1988); and Presta, *Curr. Op. Struct. Biol.* 2:593-596 (1992). See also e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mal. Biol.*, 227: 381 (1991); Marks et al., *J. Mal. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see e.g., U.S. Pat. Nos. 6,075,181 and 6,150,584 regarding XENOMOUSE™ technology). See also, for example, Li et al., *Proc. Natl. Acad. Sci. U.S.A.*, 103:3557-3562 (2006) regarding human antibodies generated via a human B-cell hybridoma technology.

A "stable" formulation is one in which the protein therein essentially retains its physical stability and/or chemical stability and/or biological activity upon storage. In some embodiments, the formulation essentially retains its physical and chemical stability, as well as its biological activity upon storage. The storage period is generally selected based on the intended shelf-life of the formulation. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993), for example. Stability can be measured at a selected amount of light exposure and/or temperature for a selected time period. Stability can be evaluated qualitatively and/or quantitatively in a variety of different ways, including evaluation of aggregate formation (for example using size exclusion chromatography, by measuring turbidity, and/or by visual inspection); evaluation of ROS formation (for example by using a light stress assay or a 2,2'-Azobis(2-Amidinopropane) Dihydrochloride (AAPH) stress assay); oxidation of specific amino acid residues of the protein (for example a Trp residue and/or a Met residue of a monoclonal antibody); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or target binding function of the protein (e.g., antigen binding function of an antibody); etc. Instability may involve any one or more of: aggregation, deamidation (e.g., Asn deamidation), oxidation (e.g., Met oxidation and/or Trp oxidation), isomerization (e.g., Asp isomerization), clipping/hydrolysis/fragmentation (e.g., hinge region fragmentation), succinimide formation, unpaired cysteine(s), N-terminal extension, C-terminal processing, glycosylation differences, degradation of excipients, formation of particulates (e.g., free fatty acid particles), etc.

A protein "retains its physical stability" in a pharmaceutical formulation if it shows no signs or very little of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve protein oxidation which can be evaluated using tryptic peptide mapping, reverse-phase high-performance liquid chromatography (HPLC) and liquid chromatography-mass spectrometry (LC/MS), for example. Other types of chemical alteration include charge alteration of the protein which can be evaluated by ion-exchange chromatography or icIEF, for example.

A protein "retains its biological activity" in a pharmaceutical formulation, if the biological activity of the protein at a given time is within about 10% (within the errors of the assay) of the biological activity exhibited at the time the pharmaceutical formulation was prepared as determined for example in an antigen binding assay for a monoclonal antibody. As used herein, "biological activity" of a protein refers to the ability of the protein to bind its target, for example the ability of a monoclonal antibody to bind to an antigen. It can further include a biological response which can be measured in vitro or in vivo. Such activity may be antagonistic or agonistic.

As used herein, the terms "polyethylene glycol," "PEG," "polyethylene oxide," "PEO," "polyoxyethylene," and "POE" may be used interchangeably and refer to a polyether compound that is composed of two or more ethylene oxide subunits. "Polyethylene glycol" may be composed of ethylene oxide oligomers (e.g., having from two to nine ethylene oxide monomer subunits) or ethylene oxide polymers (e.g., having ten or more nine ethylene oxide monomer subunits).

"Fatty acids" are carboxylic acids with long-chain hydrocarbon side groups. They are comprised of organic, monobasic acids, which are derived from hydrocarbons by the equivalent of oxidation of a methyl group to an alcohol, aldehyde, and then acid. Fatty acids can be either saturated or unsaturated. For unsaturated fatty acids, they can have cis (Z) or trans (E) configuration, or a combination of both.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl. When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl).

The term "substituted" means that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocyclyl, aralkyl, aminosulfonyl, sulfonylamino, sulfonyl, oxo, and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

A "sterile" formulation is aseptic or free or essentially free from all living microorganisms and their spores.

II. Polypeptide Formulations

Provided herein is a formulation comprising a polypeptide and a surfactant, wherein the surfactant comprises one or more components of polysorbates. In some embodiments, the formulation is a liquid formulation. In some embodiments, the formulation is a lyophilized formulation.

Surfactant

Biopharmaceutical formulations are commonly formulated with surfactants to protect the active pharmaceutical ingredient from interfacial stress. Interactions with interfaces, particularly air-water, have been shown to cause aggregation of therapeutic proteins during agitation or long term storage. Polysorbates are commonly used surfactants to prevent these types of interactions for biopharmaceuticals. They are generally selected for their high surface activity, low critical micelle concentration (CMC), and low toxicity.

These surfactants, however, are heterogeneous mixtures of related compounds, which, as a combination, give them the unique properties required for biopharmaceutical formulations.

Polysorbates (PS) are a class of emulsifiers that are canonically described as ethoxylated sorbitan esterified with fatty acids. PS are mixtures of related compounds with multiple layers of heterogeneity. The first layer is the fatty acid ester tail length. The USP and EP monographs dictate that the distribution of these esters for PS20 should be 40-60% laurate ($C_{12}$) esters, 14-25% myristate ($C_{14}$) esters, and 7-15% palmitate ($C_{16}$) esters with up to 1% caproate ($C_6$) esters, 10% caprylate ($C_8$) esters, 10% caprate ($C_{10}$) esters, 7% stearate ($C_{18}$) esters, 11% monounsaturated $C_{18}$ esters, and 3% diunsaturated $C_{18}$ esters. Additional heterogeneity is derived from the length of the POE chains as well as the presence of di- and tri-esters. Furthermore, during the synthesis of sorbitan from sorbitol, isosorbide is also formed, which can create its own series of PS20 like compounds with two POE arms instead of four. See also infra Table 1. It has been found that the various components have strikingly different solution and interfacial properties. Particularly, the isosorbide POE fatty acid ester components have greater protective properties for polypeptides. Therefore, using a greater concentration of isosorbide POE fatty acid esters (e.g, at least 70% (wt %)) than that in the polysorbates (e.g., as described in EP or USP monograph) allows the usage of a lower amount of surfactant while providing greater protection for the polypeptide in a liquid formulation.

Provided herein is a biopharmaceutical formulation comprising a surfactant with certain components of polysorbates that are efficient at protecting polypeptides in the formulation. In some embodiments, these components allow usage of less surfactant but provide greater stability. In some embodiments, the less amount of surfactant used results in less free fatty acid particle formation. In some embodiments, these components provide greater protection of polypeptides against the free fatty acid particles.

In one aspect, the surfactant comprises isosorbide POE fatty acid esters. In another aspect, the surfactant comprises isosorbide POE fatty acid esters and POE fatty acid esters.

In some embodiments, each isosorbide POE fatty acid ester and each POE fatty acid ester independently have about 5-10 POE units, about 10-15 units, about 15-20 POE units, about 20-25 POE units, about 25-30 POE units, about 15-30 POE units. In some embodiments, each isosorbide POE fatty acid ester and each POE fatty acid ester independently have 5 POE units, 6 POE units, 7 POE units, 8 POE units, 9 POE units, 10 POE units, 11 POE units, 12 POE units, 13 POE units, 14 POE units, 15 POE units, 16 POE units, 17 POE units, 18 POE units, 19 POE units, 20 POE units, 21 POE units, 22 POE units, 23 POE units, 24 POE units, 25 POE units, 26 POE units, 27 POE units, 28 POE units, 29 POE units, 30 POE units, or a combination thereof. In some embodiments, the isosorbide POE fatty acid esters have about 5-10 POE units, about 10-15 units, about 15-20 POE units, about 20-25 POE units, about 25-30 POE units, about 15-30 POE units. In some embodiments, the isosorbide POE fatty acid esters have 5 POE units, 6 POE units, 7 POE units, 8 POE units, 9 POE units, 10 POE units, 11 POE units, 12 POE units, 13 POE units, 14 POE units, 15 POE units, 16 POE units, 17 POE units, 18 POE units, 19 POE units, 20 POE units, 21 POE units, 22 POE units, 23 POE units, 24 POE units, 25 POE units, 26 POE units, 27 POE units, 28 POE units, 29 POE units, 30 POE units, or a combination thereof. In some embodiments, the isosorbide POE fatty acid esters have about 20 POE units. In some embodiments, both isosorbide POE fatty acid esters and POE fatty acid esters have about 5-30 POE units. In some embodiments, both isosorbide POE fatty acid esters and POE fatty acid esters have about 20 POE units.

In some embodiments, each isosorbide POE fatty acid ester and each POE fatty acid ester independently have a fatty acid chain independently selected from the group consisting of an optionally substituted alkyl, an optionally substituted alkenyl, and an optionally substituted alkynyl. In some embodiments, the alkyl is linear. In some embodiments, the fatty acid chain is an unsubstituted $C_{4-28}$ alkyl. In some embodiments, the fatty acid chain is a $C_{4-28}$ alkyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl, or heterocyclyl. In some embodiments, the fatty acid chain is an unsubstituted $C_{4-28}$ alkenyl. In some embodiments, the alkenyl is linear or branched. In some embodiments, the fatty acid chain has one or more double bonds. In some embodiments, each double bond has cis configuration. In some embodiments, each double bond has trans configuration. In some embodiments, the fatty acid chain is a $C_{4-28}$ alkenyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl, or heterocyclyl.

In some embodiments, each isosorbide POE fatty acid ester independently has one, two, three, or four POE arms. In some embodiments, each isosorbide POE fatty acid ester has two POE arms.

In some embodiments, the isosorbide POE fatty acid esters have the following structure of Formula (I):

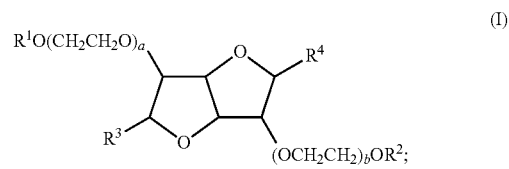

wherein:
a and b are independently integers from 2 to 28, provided that the sum of a and b is an integer from 5-30;
$R^1$ and $R^2$ are independently selected from the group consisting of hydrogen and —C(O)R", wherein R" is an optionally substituted $C_{3-27}$ alkyl or an optionally substituted $C_{3-27}$ alkenyl; and
$R^3$ and $R^4$ are independently hydrogen.

In some embodiments of Formula (I), the sum of a and b is about 5-10, about 10-15, about 15-20, about 20-25, about 25-30, or about 15-30. In some embodiments of Formula (I), the sum of a and b is 5, 6, 7, 8, 9, 10, 11, 12, 13, 14, 15, 16, 17, 18, 19, 20, 21, 22, 23, 24, 25, 26, 27, 28, 29, or 30. In some embodiments, the sum of a and b is 9. In some embodiments, the sum of a and b is 20. In some embodiments of Formula (I), at least one of $R^1$ and $R^2$ is not hydrogen. In some embodiments of Formula (I), both $R^1$ and $R^2$ are —C(O)R". In some embodiments of Formula (I), R" is an optionally substituted $C_{3-27}$ alkyl. In some embodiments of Formula (I), R" is an unsubstituted $C_{3-27}$ alkyl. In some embodiments of Formula (I), the $C_{3-27}$ alkyl is linear. In some embodiments of Formula (I), the $C_{3-27}$ alkyl is branched. In some embodiments of Formula (I), R" is unsubstituted $C_5$ alkyl, $C_7$ alkyl, $C_9$ alkyl, $C_{11}$ alkyl, $C_{1-3}$ alkyl, $C_{15}$ alkyl, $C_{17}$ alkyl, $C_{19}$ alkyl, $C_{21}$ alkyl, or $C_{23}$ alkyl. In some embodiments of Formula (I), R" is unsubstituted linear C alkyl. In some embodiments of Formula (I), R" is an optionally substituted $C_{3-27}$ alkenyl. In some embodiments of Formula (I), R" is an unsubstituted $C_{3-27}$ alkenyl. In some embodiments of Formula (I), the $C_{3-27}$ alkenyl is linear. In some embodiments of Formula (I), R" is unsubstituted $C_5$ alkenyl, $C_7$ alkenyl, $C_9$ alkenyl, $C_{11}$ alkenyl, $C_{1-3}$ alkenyl, $C_{15}$ alkenyl, $C_{17}$ alkenyl, $C_{19}$ alkenyl, $C_{21}$ alkenyl, or $C_{23}$ alkenyl. In some embodiments of Formula (I), R" has two or more double bonds. In some embodiments of Formula (I), the two or more double bonds have cis configuration. In some embodiments of Formula (I), the two or more double bonds have trans configuration. In some embodiments of Formula (I), R" has one double bond with cis configuration. In some embodiments of Formula (I), R" has one double bond with trans configuration. In some embodiments of Formula (I), R" is selected from the group consisting of $-(CH_2)_7CH=CH(CH_2)_3CH_3$, $-(CH_2)_7CH=CH(CH_2)_5CH_3$, $-(CH_2)_4CH=CH(CH_2)_8CH_3$, $-(CH_2)_7CH=CH(CH_2)_7CH_3$, $-(CH_2)_9CH=CH(CH_2)_5CH_3$, $-(CH_2)_7CH=CHCH_2CH=CH(CH_2)_4CH_3$, $-(CH_2)_7CH=CHCH_2CH=CHCH_2CH=CHCH_2CH_3$, $-(CH_2)_3CH=CHCH_2CH=CHCH_2CH=CHCH_2CH=CH(CH_2)_4CH_3$ and $-(CH_2)_{11}CH=CH(CH_2)_7CH_3$. In some embodiments of Formula (I), R" is $-(CH_2)_7CH=CH(CH_2)_7CH_3$ and the double bond has the cis configuration. In some embodiments of Formula (I), R" is $-(CH_2)_7CH=CHCH_2CH=CH(CH_2)_4CH_3$ and both double bonds have the cis configuration. In some embodiments of Formula (I), R" is $-(CH_2)_7CH=CHCH_2CH=CH(CH_2)_4CH_3$ and both double bonds have the trans configuration.

In some embodiments, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% (wt %) of the surfactant are isosorbide POE fatty acid esters and POE fatty acid esters. In some embodiments, at least 70% (wt %) of the surfactant are isosorbide POE fatty acid esters and POE fatty acid esters. In some embodiments, at least 80% (wt %) of the surfactant are isosorbide POE fatty acid esters and POE fatty acid esters. In some embodiments, at least 90% (wt %) of the surfactant are isosorbide POE fatty acid esters and POE fatty acid esters. In some embodiments, at least 95% (wt %) of the surfactant are isosorbide POE fatty acid esters and POE fatty acid esters.

In some embodiments, isosorbide POE fatty acid esters are selected from a monoester, a di-ester, a tri-ester, a tetra-ester and a combination of the foregoing. In some embodiments, isosorbide POE fatty acid esters are monoesters. In some embodiments, isosorbide POE fatty acid monoesters are selected from the group consisting of isosorbide POE monocaproate, isosorbide POE monocaprylate, isosorbide POE monocaprate, isosorbide POE monolaurate, isosorbide POE monomyristate, isosorbide POE monopalmitate, isosorbide POE monopalmitoleate, isosorbide POE monostearate, isosorbide POE monooelate, isosorbide POE monolinoleate, isosorbide POE monolinolenate, and a combination of the foregoing. In some embodiments, isosorbide POE fatty acid esters are di-esters. In some embodiments, isosorbide POE fatty acid di-esters are selected from the group consisting of isosorbide POE dicaproate, isosorbide POE dicaprylate, isosorbide POE dicaprate, isosorbide POE dilaurate, isosorbide POE dimyristate, isosorbide POE dipalmitate, isosorbide POE dipalmitoleate, isosorbide POE distearate, isosorbide POE dioelate, isosorbide POE dilinoleate, isosorbide POE dilinolenate, and a combination of the foregoing. In some embodiments, the isosobide POE fatty acid esters are compounds of Formula (I).

In some embodiments, the isosorbide POE fatty acid ester and the POE fatty acid ester have the same fatty acid chain. In some embodiments, the isosorbide POE fatty acid ester and the POE fatty acid ester have different fatty acid chains. In some embodiments, the POE fatty acid ester is selected from the group consisting of POE monocaproate, POE monocaprylate, POE monocaprate, POE monolaurate, POE monomyristate, POE monopalmitate, POE monopalmitoleate, POE monostearate, POE monooelate, POE monolinoleate, POE monolinolenate, POE dicaproate, POE dicaprylate, POE dicaprate, POE dilaurate, POE dimyristate, POE dipalmitate, POE dipalmitoleate, POE distearate, POE dioelate, POE dilinoleate, POE dilinolenate, and a combination of the foregoing. In some embodiments, the surfactant comprises isosorbide POE monolaurate and POE monolaurate. In some embodiments, the surfactant comprises isosorbide POE monopalmitate and POE monopalmitate. In some embodiments, the surfactant comprises isorsobide POE monomyristate and POE monomyristate. In some embodiments, the surfactant comprises isosorbide POE monooelate and POE monooelate. In some embodiments, the surfactant comprises isorsobide POE monolinoleate and POE monolinoleate. In some embodiments, the surfactant comprises a greater amount of isosorbide POE fatty acid esters than POE fatty acid esters. In some embodiments, less than about 40%, less than about 35%, less than about 30%, less than about 25%, less than about 20%, less than about 15%, less than about 10%, less than about 7.5%, less than about 5%, less than about 4%, less than about 3%, less than about 2%, less than about 1%, less than about 0.75%, less than about 0.5%, or less than about 0.1% (wt %) of the surfactant are POE fatty acid esters.

In another aspect, the surfactant further comprises sorbitan POE fatty acid esters. In some embodiments, each sorbitan POE fatty acid ester independently has about 5-10 POE units, about 10-15 units, about 15-20 POE units, about 20-25 POE units, about 25-30 POE units, about 15-30 POE units. In some embodiments, each sorbitan POE fatty acid ester independently has 5 POE units, 6 POE units, 7 POE units, 8 POE units, 9 POE units, 10 POE units, 11 POE units, 12 POE units, 13 POE units, 14 POE units, 15 POE units, 16 POE units, 17 POE units, 18 POE units, 19 POE units, 20 POE units, 21 POE units, 22 POE units, 23 POE units, 24 POE units, 25 POE units, 26 POE units, 27 POE units, 28 POE units, 29 POE units, 30 POE units, or a combination thereof.

In some embodiments, each sorbitan POE fatty acid ester independently has a fatty acid chain independently selected from the group consisting of an optionally substituted alkyl, an optionally substituted alkenyl, and an optionally substituted alkynyl. In some embodiments, the alkyl is linear. In some embodiments, the fatty acid chain is an unsubstituted $C_{4-28}$ alkyl. In some embodiments, the fatty acid chain is a $C_{4-28}$ alkyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl, or heterocyclyl. In some embodiments, the fatty acid chain is an unsubstituted $C_{4-28}$ alkenyl. In some embodiments, the alkenyl is linear or branched. In some embodiments, the fatty acid chain has one or more double bonds. In some embodiments, each double bond has cis configuration. In some embodiments, each double bond has trans configuration. In some embodiments, the fatty acid chain is a $C_{4-28}$ alkenyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl, or heterocyclyl.

In some embodiments, each sorbitan POE fatty acid ester independently has two, three, or four POE arms. In some embodiments, each sorbitan POE fatty acid ester has four POE arms.

In some embodiments, the sorbitan POE fatty acid esters have the following structure of Formula (II):

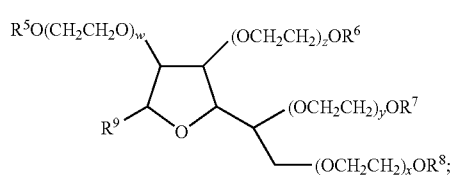

(II)

wherein:
  w, z, y, and x are independently integers from 2 to 24, provided that the sum of w, z, y and x is an integer from 15-30;
  $R^5$, $R^6$, $R^7$ and $R^8$ are independently selected from the group consisting of hydrogen and —C(O)R', wherein R' is an optionally substituted $C_{3-27}$ alkyl or an optionally substituted $C_{3-27}$ alkenyl; and
  $R^9$ is hydrogen.

In some embodiments of Formula (II), the sum of w, z, y and x is about 15-20, about 20-25, about 25-30, or about 15-30. In some embodiments of Formula (II), the sum of w, z, y and x is 15, 16, 17, 18, 19, 20, 21, 22, 23, 24, 25, 26, 27, 28, 29, or 30. In some embodiments of Formula (II), at least one of $R^5$, $R^6$, $R^7$ and $R^8$ is not hydrogen. In some embodiments of Formula (II), at least two of $R^5$, $R^6$, $R^7$ and $R^8$ are not hydrogen. In some embodiments of Formula (II), each one of $R^5$, $R^6$, $R^7$ and $R^8$ is —C(O)R'. In some embodiments, $R^5$, $R^6$ and $R^7$ are H, and $R^8$ is —C(O)R'. In some embodiments, $R^5$ and $R^6$ are H, and $R^3$ and $R^4$ are —C(O)R'. In some embodiments, $R^6$ is H, and $R^5$, $R^7$ and $R^8$ are —C(O)R'. In some embodiments of Formula (II), R' is an optionally substituted $C_{3-27}$ alkyl. In some embodiments of Formula (II), R' is an unsubstituted $C_{3-27}$ alkyl. In some embodiments of Formula (II), the $C_{3-27}$ alkyl is linear. In some embodiments of Formula (II), the $C_{3-27}$ alkyl is branched. In some embodiments of Formula (II), R' is unsubstituted $C_5$ alkyl, $C_7$ alkyl, $C_9$ alkyl, $C_{11}$ alkyl, $C_{13}$ alkyl, $C_{15}$ alkyl, $C_{17}$ alkyl, $C_{19}$ alkyl, $C_{21}$ alkyl, or $C_{23}$ alkyl. In some embodiments of Formula (II), R' is unsubstituted linear $C_{11}$ alkyl. In some embodiments of Formula (II), R' is an optionally substituted $C_{3-27}$ alkenyl. In some embodiments of Formula (II), R' is an unsubstituted $C_{3-27}$ alkenyl. In some embodiments of Formula (II), the $C_{3-27}$ alkenyl is linear. In some embodiments of Formula (II), R' is unsubstituted $C_5$ alkenyl, $C_7$ alkenyl, $C_9$ alkenyl, $C_{11}$ alkenyl, $C_{1-3}$ alkenyl, $C_{15}$ alkenyl, $C_{17}$ alkenyl, $C_{19}$ alkenyl, $C_{21}$ alkenyl, or $C_{23}$ alkenyl. In some embodiments of Formula (II), R' has two or more double bonds. In some embodiments of Formula (II), the two or more double bonds have cis configuration. In some embodiments of Formula (II), the two or more double bonds have trans configuration. In some embodiments of Formula (II), R' has one double bond with cis configuration. In some embodiments of Formula (II), R' has one double bond with trans configuration. In some embodiments of Formula (II), R' is selected from the group consisting of —(CH$_2$)$_7$CH=CH(CH$_2$)$_3$CH$_3$, —(CH$_2$)$_7$CH=CH(CH$_2$)$_5$CH$_3$, —(CH$_2$)$_4$CH=CH(CH$_2$)$_8$CH$_3$, —(CH$_2$)$_7$CH=CH(CH$_2$)$_7$CH$_3$, —(CH$_2$)$_9$CH=CH(CH$_2$)$_5$CH$_3$, —(CH$_2$)$_7$CH=CHCH$_2$CH=CH(CH$_2$)$_4$CH$_3$, —(CH$_2$)$_7$CH=CHCH$_2$CH=CHCH$_2$CH=CHCH$_2$CH$_3$, —(CH$_2$)$_3$CH=CHCH$_2$CH=CHCH$_2$CH=CHCH$_2$CH=CH(CH$_2$)$_4$CH$_3$ and —(CH$_2$)$_{11}$CH=CH(CH$_2$)$_7$CH$_3$. In some embodiments of Formula (II), R' is —(CH$_2$)$_7$CH=CH(CH$_2$)$_7$CH$_3$ and the double bond has the cis configuration. In some embodiments of Formula (II), R' is —(CH$_2$)$_7$CH=CHCH$_2$CH=CH(CH$_2$)$_4$CH$_3$ and both double bonds have the cis configuration. In some embodiments of Formula (II), R' is —(CH$_2$)$_7$CH=CHCH$_2$CH=CH(CH$_2$)$_4$CH$_3$ and both double bonds have the trans configuration.

In some embodiments, less than about 30%, less than about 25%, less than about 20%, less than about 15%, less than about 10%, less than about 9%, less than about 8%, less than about 7%, less than about 6%, less than about 5%, less than about 4%, less than about 3%, at less than about 2%, or less than about 1% (wt %) of the surfactant are sorbitan POE fatty acid esters. In some embodiments, at least 1% (wt %) of the surfactant are sorbitan POE fatty acid esters. In some embodiments, at least 5% (wt %) of the surfactant are sorbitan POE fatty acid esters. In some embodiments, at least 10% (wt %) of the surfactant are sorbitan POE fatty acid esters. In some embodiments, at least 15% (wt %) of the surfactant are sorbitan POE fatty acid esters.

In some embodiments, each sorbitan POE fatty acid ester is independently a monoester, a di-ester, a tri-ester, or a tetra-ester. In some embodiments, each sorbitan POE fatty acid ester is independently selected from the group consisting of sorbitan POE monocaproate, sorbitan POE monocaprylate, sorbitan POE monocaprate, sorbitan POE monolaurate, sorbitan POE monomyristate, sorbitan POE monopalmitate, sorbitan POE monopalmitoleate, sorbitan POE monostearate, sorbitan POE monooelate, sorbitan POE monolinoleate, sorbitan POE monolinolenate, sorbitan POE dicaproate, sorbitan POE dicaprylate, sorbitan POE dicaprate, sorbitan POE dilaurate, sorbitan POE dimyristate, sorbitan POE dipalmitate, sorbitan POE dipalmitoleate, sorbitan POE distearate, sorbitan POE dioelate, sorbitan POE dilinoleate, sorbitan POE dilinolenate, sorbitan POE tricaproate, sorbitan POE tricaprylate, sorbitan POE tricaprate, sorbitan POE trilaurate, sorbitan POE trimyristate, sorbitan POE tripalmitate, sorbitan POE tripalmitoleate, sorbitan POE tristearate, sorbitan POE trioelate, sorbitan POE trilinoleate, and sorbitan POE trilinolenate. In some embodiments, the sorbitan POE fatty acid esters are compounds of Formula (II).

In another aspect, the surfactant disclosed herein has a critical micelle concentration (CMC) of greater than about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, or about 0.1% (w:v). In another aspect, the surfactant has a surface tension of less than about 20 mN/m, about 25 mN/m, about 30 mN/m, about 35 mN/m, about 40 mN/m, about 45 mN/m, about 50 mN/m, about 55 mN/m, or about 60 mN/m.

Polypeptide

The disclosure herein relates to liquid formulations comprising a polypeptide and a surfactant. In some embodiments, the polypeptide in the liquid formulations described herein is essentially pure. In some embodiments, the polypeptide in the liquid formulations described herein is essentially homogeneous (i.e., free from contaminating proteins). "Essential pure" polypeptide means a composition comprising at least about 90% by weight of the polypeptide, based on the total weight of the composition. In some embodiments, the polypeptide is at least 95% by weight based on the total weight of the composition. "Essentially homogeneous" polypeptide means a composition comprising at least about 99% by weight of the polypeptide, based on the total weight of the composition.

In some embodiments, the polypeptide is an antibody. The antibody herein is directed against an "antigen" of interest. In some embodiments, the antigen is a biologically important protein and administration of the antibody to a mammal suffering from a disease or disorder can result in a therapeutic benefit in that mammal. In some embodiments, antibodies directed against non-protein antigens (such as tumor-associated glycolipid antigens; see e.g., U.S. Pat. No. 5,091,178) are also contemplated. Where the antigen is a protein, it may be a transmembrane molecule (e.g., receptor) or ligand such as a growth factor. Exemplary antigens include any proteins described herein. In some embodiments, molecular targets for antibodies encompassed by the present disclosure include CD polypeptides such as CD3, CD4, CD8, CD19, CD20 and CD34; members of the HER receptor family such as the EGF receptor (HER1), HER2, HER3 or HER4 receptor; interleukins (ILs), e.g., IL-1 to IL-10; cell adhesion molecules such as LFA-1, Macl, p150,95, VLA-4, ICAM-1, VCAM and av/b3 integrin including either a or b subunits thereof (e.g., anti-CD11a, antiCD18 or anti-CD11b antibodies); growth factors such as VEGF; IgE; blood group antigens; flk2/flt3 receptor; obesity (OB) receptor; mpl receptor; CTLA-4; programmed cell death protein 1 (PD-1); programmed death-ligand 1 (PD-L1); polypeptide C etc. Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule.

In some embodiments, the antibody includes, but is not limited to, polyclonal, monoclonal, humanized, human, bispecific, polyspecific, chimeric, and heteroconjugate antibodies. In some embodiments, the antibody includes antibody fragments and whole antibodies. In some embodiments, the antibody fragment is selected from the group consisting of Fab, Fab', F(ab')$_2$, and Fv fragments.

Polypeptide in the formulation may be prepared using methods known in the art, such as by culturing cells transformed or transfected with a vector containing nucleic acid encoding the polypeptide, or through synthetic techniques (e.g., recombinant techniques and peptide synthesis or a combination of these techniques) or may be isolated from an endogenous source of the polypeptide.

A. Protein Preparation

Preparation of the protein to be formulated by the method of the disclosure by recombinant means may be accomplished by transfecting or transforming suitable host cells with expression or cloning vectors and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, Ed. (IRL Press, 1991) and Sambrook et al., *Molecular Cloning: A Laboratory Manual*, New York: Cold Spring Harbor Press. Methods of transfection are known to the ordinarily skilled artisan, and include for example, CaPO$_4$ and CaCl$_2$) transfection, electroporation, microinjection, etc. Suitable techniques are also described in Sambrook et al., supra. Additional transfection techniques are described in Shaw et al., *Gene* 23: 315 (1983); WO 89/05859; Graham et al., *Virology* 52: 456-457 (1978) and U.S. Pat. No. 4,399,216.

The nucleic acid encoding the desired protein for formulation according to the present method may be inserted into a replicable vector for cloning or expression. Suitable vectors are publicly available and may take the form of a plasmid, cosmid, viral particle or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, and enhancer element, a promoter, and a transcription termination sequence. Construction of suitable vectors containing one or more of these components employs standard ligation techniques which are known to the skilled artisan.

Forms of the protein to be formulated may be recovered from culture medium or from host cell lysates. If membrane-bound, it can be released from the membrane using a suitable detergent or through enzymatic cleavage. Cells employed for expression can also be disrupted by various physical or chemical means, such as freeze-thaw cycling, sonication, mechanical disruption or cell lysing agents.

Purification of the protein to be formulated may be effected by any suitable technique known in the art, such as for example, fractionation on an ion-exchange column, ethanol precipitation, reverse phase HPLC, chromatography on silica or cation-exchange resin (e.g., DEAE), chromatofocusing, SDS-PAGE, ammonium sulfate precipitation, gel filtration using protein A Sepharose columns (e.g., Sephadex® G-75) to remove contaminants such as IgG, and metal chelating columns to bind epitope-tagged forms.

B. Antibody Preparation

In certain embodiments of the invention, the protein of choice is an antibody. Techniques for the production of antibodies, including polyclonal, monoclonal, humanized, bispecific and heteroconjugate antibodies follow.

1. Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. In some embodiments, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

2. Monoclonal Antibodies.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The immunizing agent will typically include the protein to be formulated. Generally either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, Monoclonal antibodies: Principles and Practice, Academic Press (1986), pp. 59-103.

Immortalized cell lines are usually transformed mammalian cell, particularly myeloma cells of rodent, bovine and human origin. Usually, rat or mouse myeloma cell lines are employed. The hybridoma cells thus prepared are seeded and grown in a suitable culture medium that optionally contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Suitable immortalized myeloma cells are those that fuse efficiently, support stable high-level production of antibody by the selected antibody-producing cells, and are sensitive to a medium such as HAT medium. In some embodiments, myeloma cell lines are murine myeloma lines, such as those derived from MOPC-21 and MPC-11 mouse tumors available from the Salk Institute Cell Distribution Center, San Diego, California USA, and SP-2 cells (and derivatives thereof, e.g., X63-Ag8-653) available from the American Type Culture Collection, Manassas, Virginia USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The culture medium in which the hybridoma cells are cultured can be assayed for the presence of monoclonal antibodies directed again desired antigen. In some embodiments, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. The binding affinity of the monoclonal antibody can, for example, be determined by the Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., Curr. Opinion in Immunol. 5:256-262 (1993) and Pliickthun, Immunol. Revs. 130: 151-188 (1992).

In a further embodiment, antibodies can be isolated from antibody phage libraries generated using the techniques described in McCafferty et al., Nature, 348:552-554 (1990). Clackson et al., Nature, 352:624-628 (1991) and Marks et al., J. Mal. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nucl. Acids Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3. Humanized Antibodies.

The antibodies of the invention may further comprise humanized or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domain, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332:323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.,* 151:2296 (1993); Chothia et al., *J. Mal. Biol.,* 196:901 (1987). Another method uses a particular framework derived from the consensus sequence of all human antibodies of a particular subgroup of light or heavy chains. The same framework may be used for several different humanized antibodies. Carter et al., Proc. Natl. Acad. Sci. USA, 89:4285 (1992); Presta et al., *J. Immunol.,* 151:2623 (1993).

It is further important that antibodies be humanized with retention of high affinity for the antigen and other favorable biological properties. To achieve this goal, in some embodiments, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Various forms of the humanized antibody are contemplated. For example, the humanized antibody may be an antibody fragment, such as an Fab, which is optionally conjugated with one or more cytotoxic agent(s) in order to generate an immunoconjugate. Alternatively, the humanized antibody may be an intact antibody, such as an intact IgGI antibody.

4. Human Antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 1:33 (1993); U.S. Pat. No. 5,591,669 and WO 97/17852.

Alternatively, phage display technology can be used to produce human antibodies and antibody fragments in vitro, from immunoglobulin variable (V) domain gene repertoires from unimmunized donors. McCafferty et al., Nature 348: 552-553 (1990); Hoogenboom and Winter, J. Mal. Biol. 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Curr. Opin Struct. Biol. 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also, U.S. Pat. Nos. 5,565,332 and 5,573,905.

The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., J. Immunol. 147(1): 86-95 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resemble that seen in human in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., Bio/Technology 10:779-783 (1992); Lenberg et al., Nature 368: 856-859 (1994); Morrison, Nature 368: 812-13 (1994), Fishwild et al., Nature Biotechnology 14: 845-51 (1996), Neuberger, Nature Biotechnology 14: 826 (1996) and Lenberg and Huszar, Intern. Rev. Immunol. 13:65-93 (1995).

Finally, human antibodies may also be generated in vitro by activated B cells (see U.S. Pat. Nos. 5,567,610 and 5,229,275).

5. Antibodies Fragments

In certain circumstances there are advantages to using antibody fragments, rather than whole antibodies. Smaller fragment sizes allow for rapid clearance, and may lead to improved access to solid tumors.

Various techniques have been developed for the production of antibody fragments. Traditionally, these fragments were derived via proteolytic digestion of intact antibodies (see, e.g., Morimoto et al., J Biochem Biophys. Method. 24:107-117 (1992); and Brennan et al., Science 229:81 (1985)). However, these fragments can now be produced directly by recombinant host cells. Fab, Fv and scFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-167 (1992)). According- to another approach, F(ab')2 fragments can be isolated directly from recombinant host cell culture. Fab and F(ab')$_2$ with increase in vivo half-life is described in U.S. Pat. No. 5,869,046. In other embodiments, the antibody of choice is a single chain Fv fragment (scFv). See WO 93/16185; U.S. Pat. Nos. 5,571,894 and 5,587,458. The antibody fragment may also be a "linear antibody", e.g., as described in U.S. Pat. No. 5,641,870. Such linear antibody fragments may be monospecific or bispecific.

6. Bispecific and Polyspecific Antibodies

Bispecific antibodies (BsAbs) are antibodies that have binding specificities for at least two different epitopes, including those on the same or another protein. Alternatively, one arm can be armed to bind to the target antigen, and another arm can be combined with an arm that binds to a triggering molecule on a leukocyte such as a T-cell receptor molecule (e.g., CD3) or Fc receptors for IgG (FcγR) such as FcγRI (CD64), FcγRII (CD32) and FcγRIII (CD16), so as to focus and localize cellular defense mechanisms to the target antigen-expressing cell. Such antibodies can be derived from full length antibodies or antibody fragments (e.g., F(ab')2 bispecific antibodies).

Bispecific antibodies may also be used to localize cytotoxic agents to cells which express the target antigen. Such antibodies possess one arm that binds the desired antigen and another arm that binds the cytotoxic agent (e.g., saporin, anti-interferon-a, vinca alkaloid, ricin A chain, methotrexate or radioactive isotope hapten). Examples of known bispecific antibodies include anti-ErbB2/anti-FcgRIII (WO 96/16673), anti-ErbB2/anti-FcgRI (U.S. Pat. No. 5,837, 234), anti-ErbB2/anti-CD3 (U.S. Pat. No. 5,821,337).

Methods for making bispecific antibodies are known in the art. Traditional production of full length bispecific antibodies is based on the co-expression of two immunoglobulin heavy chain-light chain pairs, where the two chains have different specificities. Millstein et al., Nature, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., EMBO J., 10:3655-3659 (1991).

According to a different approach, antibody variable domains with the desired binding specificities (antibody-antigen combining sites) are fused to immunoglobulin constant domain sequences. In some embodiments, the fusion is with an immunoglobulin heavy chain constant domain, comprising at least part of the hinge, CH2, and CH3 regions. In some embodiments, the first heavy-chain constant region (CH1) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecules provides for an easy way of separation. This approach is disclosed in WO 94/04690. For further details of generating bispecific antibodies, see, for example, Suresh et al., Methods in Enzymology 121:210 (1986).

According to another approach described in WO 96/27011 or U.S. Pat. No. 5,731,168, the interface between a pair of antibody molecules can be engineered to maximize the percentage of heterodimers which are recovered from recombinant cell culture. In some embodiments, the interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., Science 229:81 (1985) describes a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175: 217-225 (1992) describes the production of fully humanized bispecific antibody F(ab')$_2$ molecules. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., Proc. Nat. Acad. Sci. USA, 90:6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (scFv) dimers has also been reported. See Gruber et al., J. Immunol., 152:5368 (1994).

Antibodies with more than two valencies are contemplated. For example, trispecific antibodies can be prepared. Tutt et al., J. Immunol. 147: 60 (1991).

Exemplary bispecific antibodies may bind to two different epitopes on a given molecule. Alternatively, an anti-protein arm may be combined with an arm which binds to a triggering molecule on a leukocyte such as a T-cell receptor molecule (e.g., CD2, CD3, CD28 or B7), or Fc receptors for IgG (FcR), such as FcγRI (CD64), FcγRII (CD32) and FcγRIII (CD 16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

Formulation

Provided herein is a liquid formulation comprising a polypeptide and a surfactant. Any surfactant described herein may be used in the liquid formulation. In some embodiments, the surfactant in the liquid formulation has a concentration of about 0.0005% to 0.2%, about 0.0005% to 0.001%, about 0.001% to 0.002%, about 0.002% to 0.003%, about 0.003% to 0.004%, about 0.004% to 0.005%, about 0.005% to 0.006%, about 0.006% to 0.007%, about 0.007% to 0.008%, about 0.008% to 0.009%, about 0.009% to 0.01%, about 0.01% to 0.015%, about 0.015% to 0.02%, about 0.02% to 0.025%, about 0.025% to 0.03%, about 0.03% to 0.035%, about 0.035% to 0.04%, about 0.04% to 0.045%, about 0.045% to 0.05%, about 0.05% to 0.055%, about 0.055% to 0.06%, about 0.06% to 0.065%, about 0.065% to 0.07%, about 0.07% to 0.075%, about 0.075% to 0.08%, about 0.08% to 0.085%, about 0.085% to 0.09%, about 0.09% to 0.095%, about 0.095% to 0.1%, about 0.1% to 0.11%, about 0.11% to 0.12%, about 0.12% to 0.13%, about 0.13% to 0.14%, about 0.14% to 0.15%, about 0.15% to 0.16%, about 0.16% to 0.17%, about 0.17% to 0.18%, about 0.18% to 0.19%, about 0.19% to 0.2%, about 0.0005% to 0.01%, about 0.01% to 0.02%, about 0.02% to 0.03%, about 0.03% to 0.04%, about 0.04% to 0.05%, about 0.05% to 0.06%, about 0.06% to 0.07%, about 0.07% to 0.08%, about 0.08% to 0.09%, about 0.09% to 0.1%, about 0.1% to 0.12%, about 0.12% to 0.14%, about 0.14% to 0.16%, about 0.16% to 0.18%, about 0.18% to 0.2%, or about 0.0005% to 0.02% (w:v) of the liquid formulation.

In some embodiments, the isosorbide POE fatty acid esters in the liquid formulation have a concentration of about 0.00035% to 0.2%, about 0.00035% to 0.0005%, about 0.0005% to 0.001%, about 0.001% to 0.002%, about 0.002% to 0.003%, about 0.003% to 0.004%, about 0.004% to 0.005%, about 0.005% to 0.006%, about 0.006% to 0.007%, about 0.007% to 0.008%, about 0.008% to 0.009%, about 0.009% to 0.01%, about 0.01% to 0.015%, about 0.015% to 0.02%, about 0.02% to 0.025%, about 0.025% to 0.03%, about 0.03% to 0.035%, about 0.035% to 0.04%, about 0.04% to 0.045%, about 0.045% to 0.05%, about 0.05% to 0.055%, about 0.055% to 0.06%, about 0.06% to 0.065%, about 0.065% to 0.07%, about 0.07% to 0.075%, about 0.075% to 0.08%, about 0.08% to 0.085%, about 0.085% to 0.09%, about 0.09% to 0.095%, about 0.095% to 0.1%, about 0.1% to 0.11%, about 0.11% to 0.12%, about 0.12% to 0.13%, about 0.13% to 0.14%, about 0.14% to 0.15%, about 0.15% to 0.16%, about 0.16% to 0.17%, about 0.17% to 0.18%, about 0.18% to 0.19%, about 0.19% to 0.2%, about 0.00035% to 0.01%, about 0.01% to 0.02%, about 0.02% to 0.03%, about 0.03% to 0.04%, about 0.04% to 0.05%, about 0.05% to 0.06%, about 0.06% to 0.07%, about 0.07% to 0.08%, about 0.08% to 0.09%, about 0.09% to 0.1%, about 0.1% to 0.12%, about 0.12% to 0.14%, about 0.14% to 0.16%, about 0.16% to 0.18%, about 0.18% to 0.2%, or about 0.00035% to 0.14% (w:v) of the liquid formulation.

The concentration of the polypeptide in the liquid formulation can vary based on the storage configuration and the desired route of administration (e.g., subcutaneous, intramuscular, or intravitreal administration, intravenous injection or infusion, etc.). In some embodiments, the polypeptide in the liquid formulation has a concentration of about 0.1 mg/mL to 300 mg/mL, about 0.1 mg/mL to 0.5 mg/mL, about 0.5 mg/mL to 1 mg/mL, about 1 mg/mL to 1.5 mg/mL, about 1.5 mg/mL to 2 mg/mL, about 2 mg/mL to 2.5 mg/mL, about 2.5 mg/mL to 3 mg/mL, about 3 mg/mL to 3.5 mg/mL, about 3.5 mg/mL to 4 mg/mL, about 4 mg/mL to 4.5 mg/mL, about 4.5 mg/mL to 5 mg/mL, about 0.1 mg/mL to 1 mg/mL, about 1 mg/mL to 2 mg/mL, about 2 mg/mL to 3 mg/mL, about 3 mg/mL to 4 mg/mL, about 4 mg/mL to 5 mg/mL, about 5 mg/mL to 10 mg/mL, about 10 mg/mL to 15 mg/mL, about 15 mg/mL to 20 mg/mL, about 20 mg/mL to 30 mg/mL, about 30 mg/mL to 40 mg/mL, about 40 mg/mL to 50 mg/mL, about 50 mg/mL to 100 mg/mL, about 100 mg/mL to 150 mg/mL, about 150 mg/mL to 200 mg/mL, about 200 mg/mL to 250 mg/mL, about 250 mg/mL to 300 mg/mL, about 0.1 mg/mL to 2 mg/mL, about 0.5 mg/mL to 2 mg/mL, about 50 mg/mL to 150 mg/mL, about 150 mg/mL to 200 mg/mL, or 200 mg/mL to 300 mg/mL. In some embodiments, the concentration of the polypeptide in the liquid formulation is about 0.5 mg/mL. In some embodiments, the polypeptide in the liquid formulation has a concentration of greater than about 50 mg/mL, greater than about 150 mg/mL, greater than about 200 mg/mL, greater than about 250 mg/mL or greater than about 300 mg/mL. In some embodiments, the liquid formulation can be diluted to decrease the concentration of polypeptide by about 1-5 folds, about 5-10 folds, about 10-15 folds, about 15-20 folds, about 20-30 folds, about 30-40 folds, about 40-50 folds, about 50-100 folds, about 100-150 folds, about 150-200 folds, about 200-300 folds, about 300-400 folds, about 400-500 folds, about 500-600 folds, about 600-700 folds, about 700-800 folds, about 800-900 folds, about 900-1000 folds, about 1000-1500 folds, about 1500-2000 folds, about 2000-2500 folds, about 2500-3000 folds, or about 3000-5000 folds.

In some embodiments, the liquid formulation is diluted with an infusion solution. In some embodiments, the infusion solution includes, but is not limited to, dextrose-containing solution, lactated Ringer's solution, saline, half-saline or buffered saline. In some embodiments, the saline is normal saline (about 0.9% (w:v)). In some embodiments, the saline is isotonic saline. In some embodiments, the saline is buffered saline, including, but not limited to, phosphate buffered saline or Krebs-Ringer's solution. In some embodiments, the saline is isotonic or approximately isotonic with the osmolarity of the blood from the subject. The saline includes salts, such as sodium chloride, potassium chloride, magnesium chloride, or calcium chloride. In some embodiments, the saline includes one or more buffers, such as phosphate buffer (such as sodium phosphate or potassium phosphate), sodium carbonate, or HEPES. When buffered saline is used, pH is kept in a range which optimizes the therapeutic effectiveness of the polypeptide, especially if its stability is pH-dependent.

A. Lyophilized Formulations

In some embodiments, the liquid formulations described herein may also be prepared as reconstituted lyophilized formulations. The polypeptide described herein can be lyophilized and then reconstituted to produce the liquid formulation. In some embodiments, after preparation of the protein of interest as described above, a "pre-lyophilized formulation" is produced. In some embodiments, the polypeptide concentration in the reconstituted formulation is higher than in the pre-lyophilized formulation. In some embodiments, the polypeptide concentration in the reconstituted formulation is lower than that in the pre-lyophilized formulation. The concentrations of the polypeptide present in the pre-lyophilized liquid formulation and the reconstituted liquid formulation are determined taking into account the desired dose volumes, modes of administration, etc.

1. Preparation of Lyophilized Formulations.

When preparing the lyophilized formulations, the protein to be formulated is generally present in solution. For example, in the elevated ionic strength reduced viscosity formulations of the invention, the protein may be present in a pH-buffered solution at a pH from about 4-8, and preferably from about 5-7. The buffer concentration can be from about 1 mM to about 20 mM, alternatively from about 3 mM to about 15 mM, depending, for example, on the buffer and the desired tonicity of the formulation (e.g., of the reconstituted formulation). Exemplary buffers and/or salts are those which are pharmaceutically acceptable and may be created from suitable acids, bases and salts thereof, such as those which are defined under "pharmaceutically acceptable" acids, bases or buffers.

In some embodiments, a lyoprotectant is added to the pre-lyophilized formulation. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. However, exemplary lyoprotectant concentrations in the pre-lyophilized formulation are from about 10 mM to about 400 mM, alternatively from about 30 mM to about 300 mM, alternatively from about 50 mM to about 100 mM. Exemplary lyoprotectants include sugars and sugar alcohols such as sucrose, mannose, trehalose, glucose, sorbitol, and mannitol. However, under particular circumstances, certain lyoprotectants may also contribute to an increase in viscosity of the formulation. As such, care should be taken so as to select particular lyoprotectants which minimize or neutralize this effect. Additional lyoprotectants are described above under the definition of "lyoprotectants," also referred herein as "pharmaceutically-acceptable sugars".

The ratio of protein to lyoprotectant can vary for each particular protein or antibody and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, or from about 200 to about 1000 moles of lyoprotectant to 1 mole antibody, for example from about 200 to about 600 moles of lyoprotectant to 1 mole antibody.

The formulation herein may also contain more than one protein as necessary for the particular indication being treated, such as those with complementary activities that do not adversely affect the other protein. For example, it may be desirable to provide two or more antibodies which bind to the desired target (e.g., receptor or antigen) in a single formulation. Such proteins are suitably present in combination in amounts that are effective for the purpose intended.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, optional lyoprotectant and other optional components are mixed together, the formulation is lyophilized. Many different freeze-dryers are available for this purpose such as Hull50™ (Hull, USA) or GT20™ (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g., 40-60 hrs). Optionally, a secondary drying stage may also be performed depending upon the desired residual moisture level in the product. The temperature at which the secondary drying is carried out ranges from about 0-40° C., depending primarily on the type and size of container and the type of protein employed. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g., 10-15 hours). The pressure may be the same as that employed during the primary drying step. Freeze-drying conditions can be varied depending on the formulation and vial size.

2. Reconstitution of Lyophilized Formulations

Prior to administration to the patient, the lyophilized formulation is reconstituted with a pharmaceutically acceptable diluent such that the protein concentration in the reconstituted formulation is at least about 50 mg/mL, for example from about 50 mg/mL to about 400 mg/mL, alternatively from about 80 mg/mL to about 300 mg/mL, alternatively from about 90 mg/mL to about 150 mg/mL. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 0.1-2 mg/mL, from about 2-10 mg/mL, or from about 10-50 mg/mL protein in the reconstituted formulation). In certain embodiments, the protein concentration in the reconstituted formulation is significantly higher than that in the pre-lyophilized formulation. In certain embodiments, the protein concentration in the reconstituted formulation is significantly lower than that in the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g., phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0%, or from about 0.5-1.5%, or from about 1.0-1.2%.

In some embodiments, the liquid formulation, including but not limited to reconstituted liquid formulation, is substantially free of aggregates. In some embodiments, the liquid formulation, including but not limited to reconstituted liquid formulation, comprises less free fatty acid particle formation.

III. Methods of Making Liquid Formulations

Also provided here are methods for making a liquid formulation comprising adding a polypeptide and a surfactant to an aqueous solution, wherein the surfactant comprises one or more components of polysorbates.

In some embodiments, the surfactant comprises isosorbide POE fatty acid esters. In some embodiments, the surfactant further comprises POE fatty acid esters. In some embodiments, the isosorbide POE fatty acid esters and POE fatty acid esters independently have about 5-30 POE units. In some embodiments, the isosorbide POE fatty acid esters and POE fatty acid esters independently have fatty acid chains independently selected from the group consisting of an optionally substituted $C_{4-28}$ alkyl and an optionally substituted $C_{4-28}$ alkenyl. In some embodiments, the isosorbide POE fatty acid esters are compounds of Formula (I). In some embodiments, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% (wt %) of the surfactant are isosorbide POE fatty acid esters and POE fatty acid esters. In some embodiments, isosorbide POE fatty acid esters are selected from the group consisting of isosorbide POE monocaproate, isosorbide POE monocaprylate, isosorbide POE monocaprate, isosorbide POE monolaurate, isosorbide POE monomyristate, isosorbide POE monopalmitate, isosorbide POE monopalmitoleate, isosorbide POE monostearate, isosorbide POE monooelate, isosorbide POE monolinoleate, isosorbide POE monolinolenate, and a combination of the foregoing. In some embodiments, the POE fatty acid esters are selected from the group consisting of POE monocaproate, POE monocaprylate, POE monocaprate, POE monolaurate, POE monomyristate, POE monopalmitate, POE monopalmitoleate, POE monostearate, POE monooelate, POE monolinoleate, POE monolinolenate, and a combination of the foregoing. In some embodiments, the surfactant comprises isosorbide POE monolaurate and POE monolaurate. In some embodiments, the surfactant comprises isosorbide POE monopalmitate and POE monopalmitate. In some embodiments, the surfactant comprises isosorbide POE monomyristate and POE monomyristate. In some embodiments, the surfactant comprises isosorbide POE monooelate and POE monooelate. In some embodiments, the surfactant comprises isosorbide POE monolinoleate and POE monolinoleate.

In some embodiments, the surfactant further comprises sorbitan POE fatty acid esters. In some embodiments, the sorbitan POE fatty acid esters independently have fatty acid chains independently selected from the group consisting of an optionally substituted $C_{4-28}$ alkyl and an optionally substituted $C_{4-28}$ alkenyl. In some embodiments, the sorbitan POE fatty acid esters are compounds of Formula (II). In some embodiments, less than about 30%, less than about 25%, less than about 20%, less than about 15%, less than about 10%, less than about 9%, less than about 8%, less than about 7%, less than about 6%, less than about 5%, less than about 4%, less than about 3%, at less than about 2%, or less than about 1% (wt %) of the surfactant are sorbitan POE fatty acid esters. In some embodiments, at least 1% (wt %) of the surfactant are sorbitan POE fatty acid esters. In some embodiments, at least 5% (wt %) of the surfactant are sorbitan POE fatty acid esters. In some embodiments, at least 10% (wt %) of the surfactant are sorbitan POE fatty acid esters. In some embodiments, at least 15% (wt %) of the surfactant are sorbitan POE fatty acid esters.

In some embodiments, each sorbitan POE fatty acid ester is independently selected from the group consisting of sorbitan POE monocaproate, sorbitan POE monocaprylate, sorbitan POE monocaprate, sorbitan POE monolaurate, sorbitan POE monomyristate, sorbitan POE monopalmitate, sorbitan POE monopalmitoleate, sorbitan POE monostearate, sorbitan POE monooelate, sorbitan POE monolinoleate, sorbitan POE monolinolenate, sorbitan POE dicaproate, sorbitan POE dicaprylate, sorbitan POE dicaprate, sorbitan POE dilaurate, sorbitan POE dimyristate, sorbitan POE dipalmitate, sorbitan POE dipalmitoleate, sorbitan POE distearate, sorbitan POE dioelate, sorbitan POE dilinoleate, sorbitan POE dilinolenate, sorbitan POE tricaproate, sorbitan POE tricaprylate, sorbitan POE tricaprate, sorbitan POE trilaurate, sorbitan POE trimyristate, sorbitan POE tripalmitate, sorbitan POE tripalmitoleate, sorbitan POE tristearate, sorbitan POE trioelate, sorbitan POE trilinoleate, and sorbitan POE trilinolenate.

Any of the surfactant described herein can be used in the method to make liquid formulations.

In some embodiments, the surfactant in the liquid formulation has a concentration of about 0.0005% to 0.2%, about 0.0005% to 0.001%, about 0.001% to 0.002%, about 0.002% to 0.003%, about 0.003% to 0.004%, about 0.004% to 0.005%, about 0.005% to 0.006%, about 0.006% to 0.007%, about 0.007% to 0.008%, about 0.008% to 0.009%, about 0.009% to 0.01%, about 0.01% to 0.015%, about 0.015% to 0.02%, about 0.02% to 0.025%, about 0.025% to 0.03%, about 0.03% to 0.035%, about 0.035% to 0.04%, about 0.04% to 0.045%, about 0.045% to 0.05%, about 0.05% to 0.055%, about 0.055% to 0.06%, about 0.06% to 0.065%, about 0.065% to 0.07%, about 0.07% to 0.075%, about 0.075% to 0.08%, about 0.08% to 0.085%, about 0.085% to 0.09%, about 0.09% to 0.095%, about 0.095% to 0.1%, about 0.1% to 0.11%, about 0.11% to 0.12%, about 0.12% to 0.13%, about 0.13% to 0.14%, about 0.14% to 0.15%, about 0.15% to 0.16%, about 0.16% to 0.17%, about 0.17% to 0.18%, about 0.18% to 0.19%, about 0.19% to 0.2%, about 0.0005% to 0.01%, about 0.01% to 0.02%, about 0.02% to 0.03%, about 0.03% to 0.04%, about 0.04% to 0.05%, about 0.05% to 0.06%, about 0.06% to 0.07%, about 0.07% to 0.08%, about 0.08% to 0.09%, about 0.09% to 0.1%, about 0.1% to 0.12%, about 0.12% to 0.14%, about 0.14% to 0.16%, about 0.16% to 0.18%, about 0.18% to 0.2%, or about 0.0005% to 0.02% (w:v) of the liquid formulation.

The concentration of the polypeptide in the liquid formulation can vary based on the storage configuration and the desired route of administration (e.g., subcutaneous, intramuscular, or intravitreal administration, intravenous injection or infusion, etc.). In some embodiments, the polypeptide in the liquid formulation has a concentration of about 0.1 mg/mL to 300 mg/mL, about 0.1 mg/mL to 0.5 mg/mL, about 0.5 mg/mL to 1 mg/mL, about 1 mg/mL to 1.5 mg/mL, about 1.5 mg/mL to 2 mg/mL, about 2 mg/mL to 2.5 mg/mL, about 2.5 mg/mL to 3 mg/mL, about 3 mg/mL to 3.5 mg/mL, about 3.5 mg/mL to 4 mg/mL, about 4 mg/mL to 4.5 mg/mL, about 4.5 mg/mL to 5 mg/mL, about 0.1 mg/mL to 1 mg/mL, about 1 mg/mL to 2 mg/mL, about 2 mg/mL to 3 mg/mL, about 3 mg/mL to 4 mg/mL, about 4 mg/mL to 5 mg/mL, about 5 mg/mL to 10 mg/mL, about 10 mg/mL to 15 mg/mL, about 15 mg/mL to 20 mg/mL, about 20 mg/mL to 30 mg/mL, about 30 mg/mL to 40 mg/mL, about 40 mg/mL to 50 mg/mL, about 50 mg/mL to 100 mg/mL, about 100 mg/mL to 150 mg/mL, about 150 mg/mL to 200 mg/mL, about 200 mg/mL to 250 mg/mL, about 250 mg/mL to 300 mg/mL, about 0.1 mg/mL to 2 mg/mL, about 0.5 mg/mL to 2 mg/mL, about 50 mg/mL to 150 mg, about 150 mg/mL to 200 mg/mL, or 200 mg/mL to 300 mg/mL. In some embodiments, the concentration of the polypeptide in the liquid formulation is about 0.5 mg/mL. In some embodiments, the polypeptide in the liquid formulation has a concentration of greater than about 50 mg/mL, greater than about 150 mg/mL, greater than about 200 mg/mL, greater than about 250 mg/mL or greater than about 300 mg/mL.

In some embodiments, the method further comprises diluting the liquid formulation to decrease the concentration of polypeptide by about 1-5 folds, about 5-10 folds, about 10-15 folds, about 15-20 folds, about 20-30 folds, about 30-40 folds, about 40-50 folds, about 50-100 folds, about 100-150 folds, about 150-200 folds, about 200-300 folds, about 300-400 folds, about 400-500 folds, about 500-600 folds, about 600-700 folds, about 700-800 folds, about 800-900 folds, about 900-1000 folds, about 1000-1500 folds, about 1500-2000 folds, about 2000-2500 folds, about 2500-3000 folds, or about 3000-5000 folds. In some embodiments, the method further comprises diluting the liquid formulation with an infusion solution. In some embodiments, the infusion solution includes, but is not limited to, dextrose-containing solution, lactated Ringer's solution, saline or buffered saline. In some embodiments, the saline is normal saline (about 0.9% (w:v)). In some embodiments, the saline is isotonic saline. In some embodiments, the saline is buffered saline, including, but is not limited to, phosphate buffered saline or Krebs-Ringer's solution. In some embodiments, saline is isotonic or approximately isotonic with the osmolarity of the blood from the subject. The saline includes salts, such as sodium chloride, potassium chloride, magnesium chloride, or calcium chloride. In some embodiments, the saline includes one or more buffers, such as phosphate buffer (such as sodium phosphate or potassium phosphate), sodium carbonate, or HEPES. When buffered saline is used, pH is kept in a range which optimizes the therapeutic effectiveness of the polypeptide, especially if its stability is pH-dependent. In some embodiments, the liquid formulation is diluted prior to administration to a subject.

When the liquid formulation is prepared by reconstituting a lyophilized formulation, the reconstitution generally takes place at a temperature of about 25° C. to ensure complete hydration, although other temperatures may be employed as desired. The time required for reconstitution will depend, e.g., on the type of diluent, amount of excipient(s) and polypeptide. Exemplary diluents include sterile water, bacteriostatic water for injection (BWFI), a pH buffered solution (e.g., phosphate-buffered saline), sterile saline solution, Ringer's solution or dextrose solution. The diluent optionally contains a preservative.

In some embodiments, the polypeptide used in the method is an antibody. In some embodiments, the antibody is polyclonal, monoclonal, humanized, human, bispecific, polyspecific, chimeric, or heteroconjugate antibody. In some embodiments, the antibody includes antibody fragments and whole antibodies. In some embodiments, the antibody fragment is selected from the group consisting of Fab, Fab', F(ab')$_2$, and Fv fragments.

In another aspect, the methods may be used to make any liquid formulations described herein.

IV. Article of Manufacture

Provided here are articles of manufacture comprising a container enclosing the liquid formulation, wherein the liquid formulation comprises a polypeptide and a surfactant, wherein the surfactant comprises one or more components of polysorbates.

The article of manufacture comprises a container. Suitable containers include, but are not limited to, bottles, vials (e.g., dual-chamber vials), syringes (e.g., single- or dual-chamber syringes), test tubes, and intravenous therapy (IV) bags. In some embodiments, the IV bag comprises an infusion solution. In some embodiments, the infusion solution includes, but is not limited to, dextrose-containing solution, lactated Ringer's solution, saline or buffered saline. The container may be formed form a variety of materials such as glass, metal alloy (e.g., stainless steel), or plastic. The label, which is on, or associated with, the container holding the liquid formulation may indicate directions for reconstitution and/or use. In some embodiments, the label may further indicate that the formulation is useful or intended for subcutaneous administration. In some embodiments, the label may further indicate that the formulation is useful or intended for intravenous administration (e.g., as a bolus or by continuous infusion over a period of time, by intramuscular, intraperitoneal, intracerobrospinal, subcutaneous, intra-articular, intrasynovial, or intrathecal administration). In some embodiments, the label may further indication that the formation is useful or intended for intravitreal administration. The container holding the formulation may be a multi-use vial, which allows for repeat administrations (e.g., from 2-6 administrations) of the liquid formulation. In some embodiments, the article of manufacture comprises a polypeptide with a concentration of about 0.1 mg/mL to about 300 mg/mL. The article of manufacture may further comprise a second container comprising a suitable diluent (e.g., water, formulation buffer, surfactant solution, and infusion solution, such as dextrose-containing solution, saline, lactated Ringer's solution and BWFI). Upon mixing of the diluent and the liquid formulation, the final protein concentration in the diluted formulation will generally be at least 0.001 mg/mL. In some embodiments, the diluent is mixed with a lyophilized formulation to form a reconstituted liquid formulation. In some embodiments, the final protein concentration in the liquid formulation, including the reconstituted liquid formulation, is about 0.5 mg/mL to about 2 mg/mL. The article of manufacture may further include other materials desirable from a commercial and user standpoint, including other buffers, diluents, filters, needles, syringes, and package inserts with instructions for use. In some embodiments, the article of manufacture contains syringes or equipment for intravenous administration, and/or a sterile buffered solution for preparing a lyophilized composition for administration.

In another aspect, the article of manufacture may contain any liquid formulations described herein. In another aspect, the article of manufacture may contain a liquid formulation that is prepared according to any method of making described herein.

V. Medicaments and Methods of Treatment Using the Liquid Formulation

Also provided herein are methods for treating a disease or disorder in a subject comprising administering an effective amount of a liquid formulation described herein to the subject in need thereof. Also provided herein are uses of a liquid formulation described herein in the preparation of a medicament for treating a patient in need of treatment with the polypeptide in the liquid formulation. Also provided are liquid formulations as described herein for treating a disease or disorder in a subject in need of the treatment with the polypeptide in the liquid formulations. Also provided are liquid formulations as described herein for treating a patient comprising administering an effective amount of the liquid formulation to the patient.

Where the antibody in the formulation binds to HER2, the suspension formulation can be used to treat cancer. The cancer will generally comprise HER2-expressing cells, such that the HER2 antibody herein is able to bind to the cancer cells. Thus, the invention in this embodiment concerns a method for treating HER2-expressing cancer in a subject, comprising administering the HER2 antibody pharmaceutical formulation to the subject in an amount effective to treat the cancer. Exemplary cancers to be treated herein with a HER2 antibody (e.g., trastuzumab or pertuzumab) are HER2-positive breast cancer or gastric cancer.

Where the antibody in the formulation binds to a B-cell surface maker such as CD20, the formulation may be used to treat a B-cell malignancy, such as NHL or CLL, or an autoimmune disease (e.g., rheumatoid arthritis or vasculitis).

Where the antibody in the formulation binds VEGF (e.g., bevacizumab), the formulation may be used to inhibit angiognesis, treat cancer (such as colorectal, non-small cell lung (NSCL), glioblastoma, breast cancer, and renal cell carcinoma), or treat age-related macular degeneration (AMD) or macular edema.

Where the indication is cancer, the patient may be treated with a combination of the suspension formulation, and a chemotherapeutic agent. The combined administration includes co-administration or concurrent administration, using separate formulations or a single pharmaceutical formulation, and consecutive administration in either order, wherein there is a time period when both (or all) active agents simultaneously exert their biological activities. Thus, the chemotherapeutic agent may be administered prior to, or following, administration of the composition. In this embodiment, the timing between at least one administration of the chemotherapeutic agent and at least one administration of the formulation is approximately 1 month or less, or approximately 2 weeks or less. Alternatively, the chemotherapeutic agent and the formulation are administered concurrently to the patient, in a single formulation or separate formulations.

Treatment with the suspension formulation will result in an improvement in the signs or symptoms of the disease or disorder. Moreover, treatment with the combination of the chemotherapeutic agent and the antibody formulation may result in a synergistic, or greater than additive, therapeutic benefit to the patient.

In some embodiments, the liquid formulation described herein is administered intravenously. In some embodiments, the liquid formulation described herein is administered by intravenous injection with the rate of administration controlled such that administration occurs over at least about 30 minutes or longer. The dosing schedule and actual dosage administered may vary depending on such factors as the nature and severity of the infection, the age, weight, and general health of the patient and the disease or disorder to be treated, and will be ascertainable to health professionals. The liquid formulation is suitably administered to the subject at one time or over a series of treatments. Depending on the type and severity of the disease, about 1 g/kg to 50 mg/kg (e.g., 0.1-20 mg/kg) of antibody is an initial candidate dosage for administration to the patient, whether, for example, by one or more separate administrations. The dosage of the antibody will generally be from about 0.05 mg/kg to about 10 mg/kg. If a chemotherapeutic agent is administered, it is usually administered at dosages known therefor, or optionally lowered due to combined action of the drugs or negative side effects attributable to administration of the chemotherapeutic agent.

EXAMPLES

The following examples are offered to illustrate but not to limit the invention. One of skill in the art will recognize that the following procedures may be modified using methods known to one of ordinary skill in the art.

Materials

Monoclonal antibodies A through D were manufactured by Genentech, Inc. (South San Francisco, CA, USA). Polysorbate 20 containing ~99% laurate esters was synthesized by BASF SE (Ludwigshafen, Germany). Polysorbate 80 HX2 Ultra-Purity grade containing ~98% oleate esters was synthesized by NOF America Corp. (Irvine, CA). All polysorbate samples were stored with a nitrogen overlay at 2-8° C. when not in use. Acetonitrile and Methanol (HPLC grade) were purchased from Avantor Performance Materials, Inc. (Phillipsburg, NJ).

Example 1 Polysorbate Fractionation and Analysis

Polysorbate Fractionation

Fractionation of polysorbates (PS) was conducted using a Gilson PLC-2050 Prep HPLC system. For all PS samples, 2 grams of polysorbate 20 (PS20) or polysorbate 80 (PS80) were dissolved in 8 mL of >18 MΩ cm water and injected onto a Waters X-Bridge BEH C4 column (30×100 mm). The samples were then fractionated using a gradient of >18 MΩ·cm water (mobile phase A) and acetonitrile (mobile phase B). The gradient conditions were: 0.0-3.0 minutes, 5% B; 3.0-20.0 minutes, 5-100% B; 20.0-27.0 minutes, 100% B; 27-27.1 minutes, 100-5% B; 27.1-30.0 minutes, 5% B. The flow rate was 40 mL/min with a total run time of 30 minutes. 25 mL fractions were collected throughout the run. These fractions were then analyzed using a reversed phase ultra high performance liquid chromatography method with charged aerosol detection (RP-UHPLC-CAD), described in the subsequent section. Following the analysis, the fractions were pooled and dried using a rotavap.

Polysorbate Fraction Pry Analysis

Fractionated PS samples were assessed for pooling and purity using a Waters Acquity UPLC H-Class system equipped with a Thermo Corona Ultra CAD detector. The column used was a Waters Acquity BEH C8 column (2.1×50 mm, 120 Å, and 2.5 μm particle size). The gradient was as follows: 0.0-0.5 minutes, 5% B; 0.5-5.0 minutes, 5-100% B; 5.0-6.0 minutes, 100% B; 6.0-6.1 minutes, 100-5% B; 6.1-8.0 minutes, 5% B. CAD was performed with data collection at 10 Hz and nebulizer temperature at 30° C.

Results

Figure 1B:
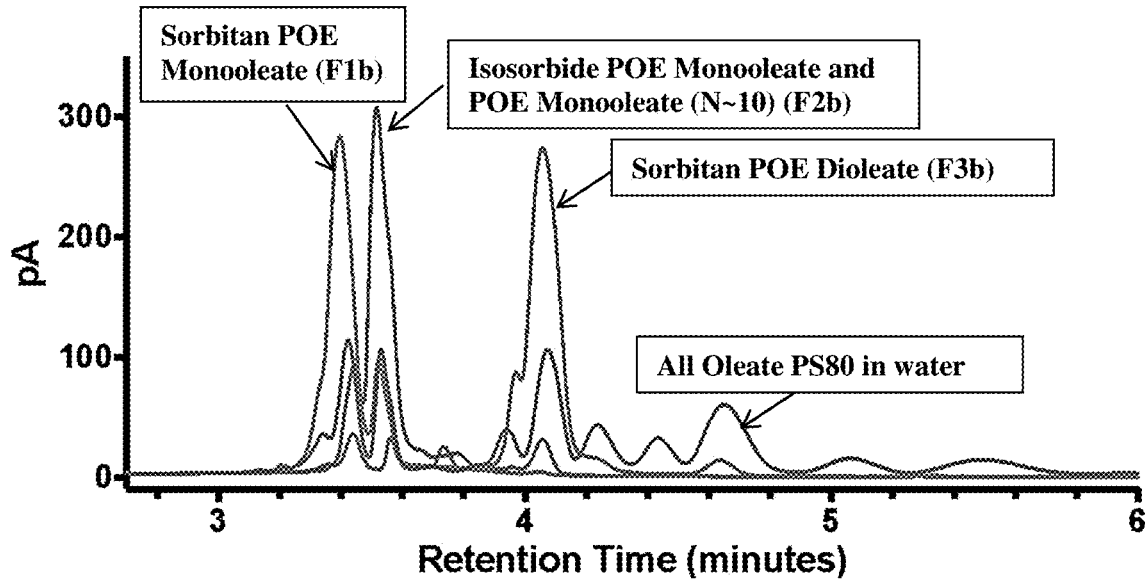

PS20 and PS80 fractions were purified and dried by rotavap. Their relative purities as determined by RP-UHPLC-CAD are shown in Table 1 below. Three fractions were purified and analyzed from each PS type. For PS20, these fractions were: POE-sorbitan monolaurate ("Fraction 1 or F1a"), POE-isosorbide monolaurate and POE monolaurate (N~10) ("Fraction 2 or F2a"), and POE-sorbitan dilaurate ("Fraction 3 or F3a"). For PS80, the fractions were: POE-sorbitan monooleate ("Fraction 1 or F1b"), POE-isosorbide monooleate and POE monooleate (N~10) ("Fraction 2 or F2b"), and POE-sorbitan dioleate ("Fraction 3 or F3b"). The identity of each of the fractions was confirmed by LC-MS analysis. The reversed phase UHPLC-CAD analysis confirmed the most hydrophobic of the Polysorbate ester fractions was F3, followed by F2 then F1 as the least hydrophobic (FIGS. 1A and 1B).

TABLE 1

| | PS20 | | PS80 | |
| | USP/EP Specs | All Laurate PS20 (custom material) | USP/EP Specs | All Oleate PS80 from Source B |
| Acid | | | | |
| --- | --- | --- | --- | --- |
| Caproic (C6) | ≤1.0% | NT | — | — |
| Caprylic (C8) | ≤10.0% | NT | — | — |
| Capric (C10) | ≤10.0% | NT | — | — |
| Lauric (C12) | 40.0-60.0% | >99% | — | — |
| Myristic (C14) | 14.0-25.0% | NT | ≤5.0% | NT |
| Palmitic (C16) | 7.0-15.0% | NT | ≤16.0% | NT |
| Palmitoleic (C16:1) | — | NT | ≤8.0% | NT |

TABLE 1-continued

| | PS20 | | PS80 | |
| --- | --- | --- | --- | --- |
| | | All Laurate | | |
| Acid | USP/EP Specs | PS20 (custom material) | USP/EP Specs | All Oleate PS80 from Source B |
| Stearic (C18) | ≤7.0% | NT | ≤6.0% | NT |
| Oleic (C18:1) | ≤11.0% | NT | ≥58.0% | 98.9% |
| Linoleic (C18:2) | ≤3.0% | NT | ≤18.0% | NT |
| Linolenic (C18:3) | — | — | ≤4.0% | NT |

*NT: not determined

Example 2 Critical Micelle Concentration (CMC) Determination

Purified PS fractions were assessed for their critical micelle concentration (CMC) using the fluorescent dye N-Phenylnaphthalen-1-amine (NPN). This assay was performed by making 2-fold serial dilutions into a diluent composed of 0.15 M sodium chloride, 0.05 M TRIS, 5% ACN, 5 M N-phenyl-1-naphtylamine and 15 ppm Brij35 at pH 8.0. The samples were analyzed immediately in a Molecular Devices Spectramax M5 fluorescence plate reader with excitation at 350 nm and emission at 420 nm.

Figure 2A:
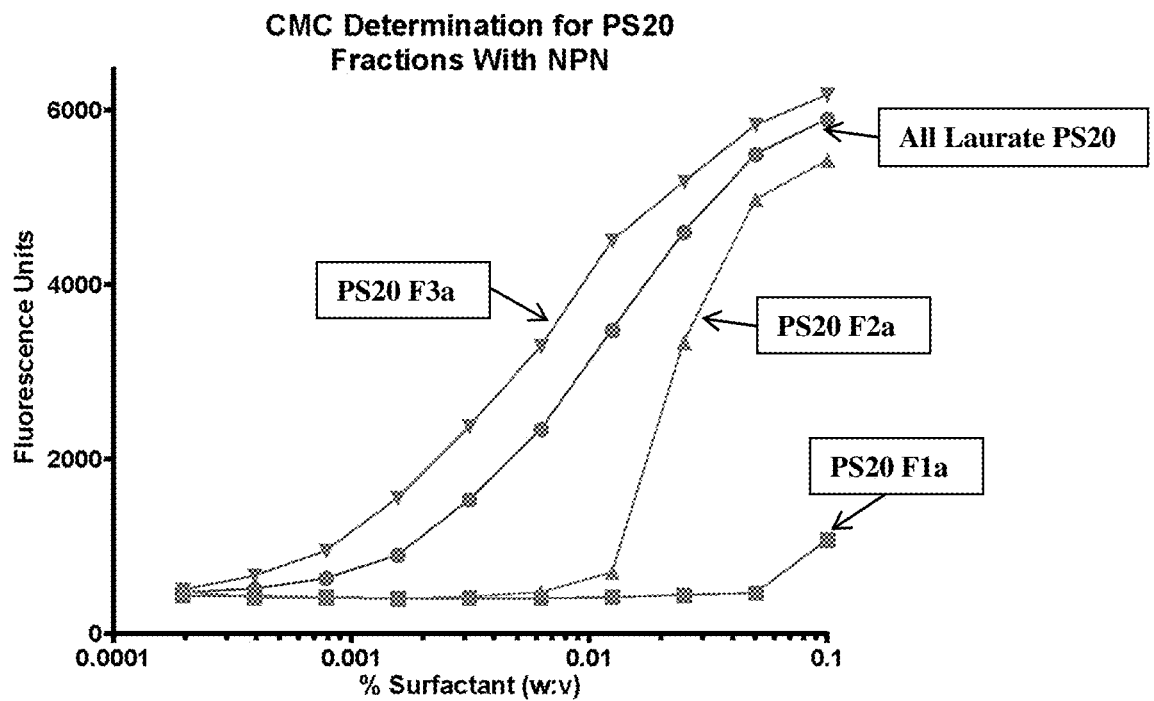
FIGS. 2A and 2B show the Critical Micelle Concentrations (CMC) of polysorbate 20 fractions (FIG. 2A) and polysorbate 80 fractions (FIG. 2B) using fluorescent dye N-phenylnaphthalen-1-amine (NPN).
Figure 2B:
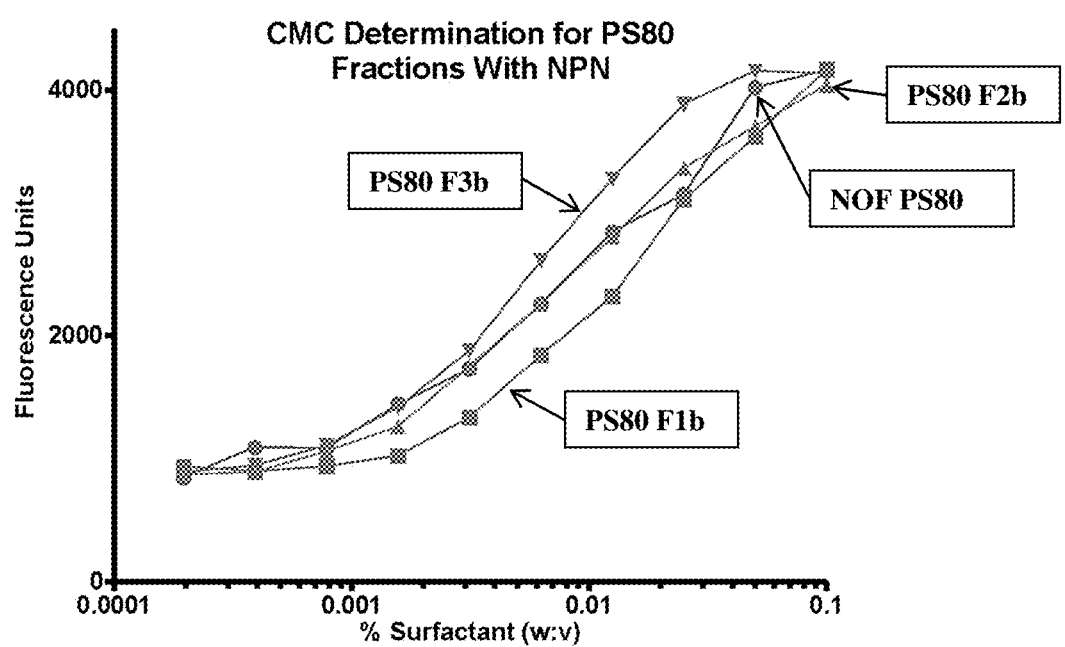

For PS20, the order of increasing CMC was F3a>F2a>F1a, consistent with the order of hydrophobicity. The CMC was widely separated, with ~0.1 wt % for F1a, ~0.015 wt % for F2a, and ~0.001 wt % for F3a, corresponding to approximately 500 fluorescence units change from the baseline (FIG. 2A). In contrast, while the PS80 ester CMCs had similar ordering, the range of the values was much narrower, spanning just 0.001 to 0.003 wt % (FIG. 2B).

Example 3 Surface Activity of Fractionated PS Samples

The surface activity of purified fractions of PS was determined using a Kruss (Hamburg, Germany) K100 Force Tensiometer using a roughened platinum Wilhemy plate. The samples were measured at room temperature (20-25° C.) with >70% relative humidity to prevent evaporation. Purified fractions of PS20 were each dissolved to 0.2 mg/mL in purified water prior to testing. Three milliliters of sample was placed in the sample holder with particular care not to introduce bubbles. The changes in surface tension of each sample were measured until equilibrium at 60 minutes, with one measurement per second. Same procedure was followed for PS80 analysis.

Figure 3A:
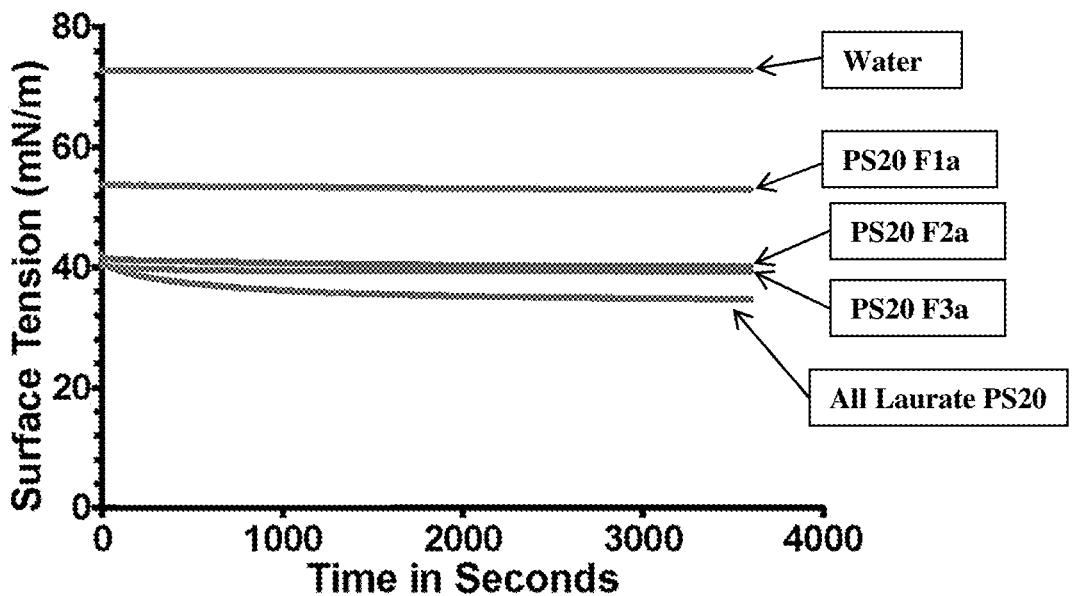
FIGS. 3A and 3B show the surface tension over time for polysorbate 20 fractions (FIG. 3A) and polysorbate 80 fractions (FIG. 3B).
Figure 3B:
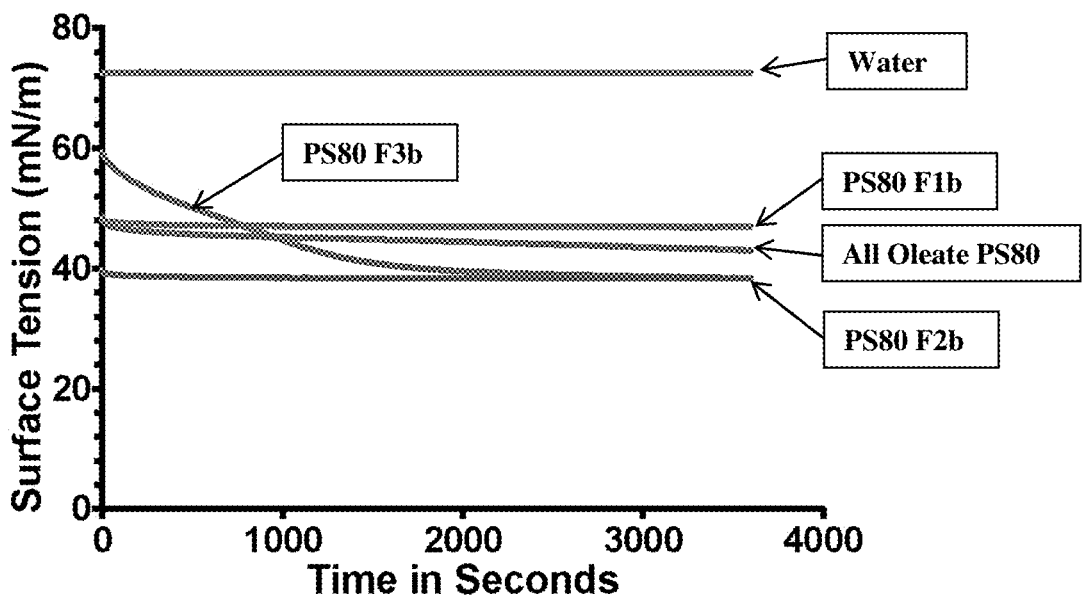

The surface tension results showed that at equilibrium, for the same concentration of 0.02 wt %, the PS20 F3a and F2a fractions were significantly more effective in lowering surface tension than the less hydrophobic F1a fraction (FIG. 3A). A similar trend is seen for the PS80 F1b to F3b fractions (FIG. 3B). Interestingly, the surface tension of PS20 fraction F3a is approximately the same as F2a, and that of PS80 fraction F3b is likewise similar to F2b. Furthermore, the unfractionated PS20 containing all the ester fractions lowered the surface tension even more than the F3a or F2a fractions (FIG. 3A). In contrast, the unfractionated PS80 showed a surface tension in between that of its F1b and F3b fractions (FIG. 3B).

Example 4 Dynamic Light Scattering of Micelle Size

Dynamic light scattering (DLS) was performed on a Malvern (Westborough, MA) Zetasizer Nano instrument. The measurements were performed by diluting each fraction sample to a final concentration of 10 mg/mL in water—so as to be above the CMC for each fraction.

Figure 4A:
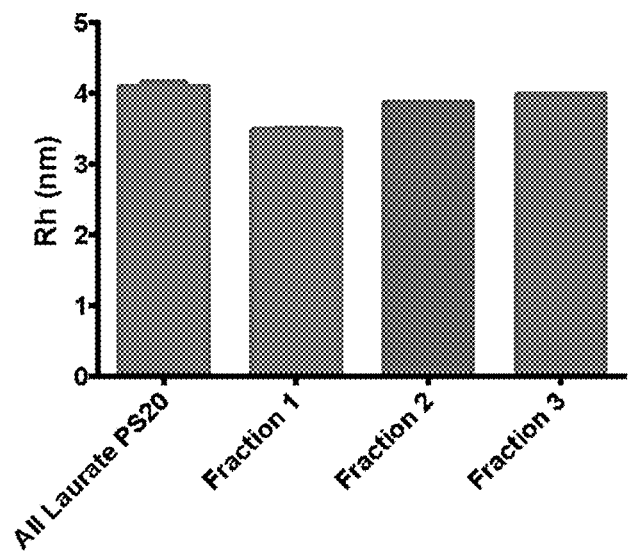
FIGS. 4A and 4B show the micelle size for polysorbate 20 fractions (FIG. 4A) and polysorbate 80 fractions (FIG. 4B) with each fraction having a concentration of 1 wt %.
Figure 4B:
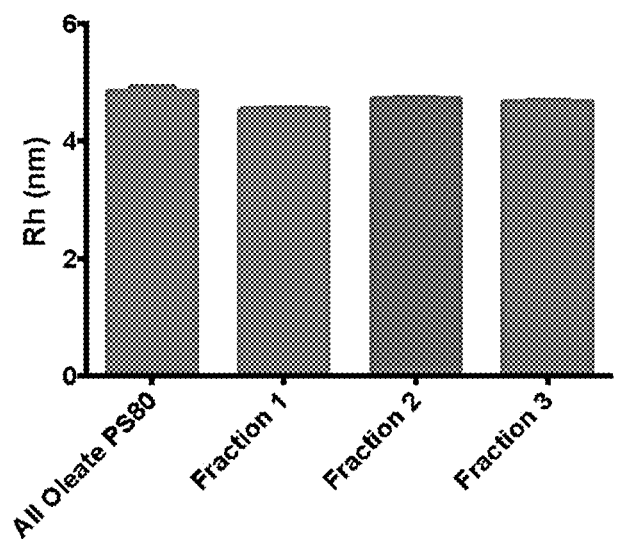

The micelle radius or hydrodynamic radius ($R_h$) was obtained using dynamic light scattering (DLS) and using a fraction concentration of 1 wt %, which is well above the CMC of all the ester fractions studied. For PS20, the $R_h$ for the unfractionated PS20 was about 4 nm, and the F2a and F3a fractions were about 3.9 nm. The $R_h$ of the F1a monoester is a bit smaller, around 3.5 nm (FIG. 4A). For PS80, the micelle size was likewise a bit larger for the unfractionated PS80 sample ($R_h$~4.8 nm) compared to the F2b and F3b fractions whose $R_h$ are similar at around 4.5 nm. The $R_h$ of the F1b, like F1a, is the smallest in the PS80 sample set, but not by much with $R_h$~4.3 nm (FIG. 4B).

Example 5 Agitation Protection Study

The purified fractions were tested for their ability to prevent surface induced aggregation through the use of an agitation study. mAb A was diluted to 0.5 mg/mL in 0.9% saline with varying amounts of each of the PS20 fractions (F1a, F2a, and F3a from 0.0001% to 0.01%, w:v) in 10 mL PETG vials. These vials were agitated on an orbital shaker at 180 RPM for 2 hours at ambient temperature. Following agitation, the samples were observed using a Bosch APK system with 10× magnification and rotation.

Figure 5:
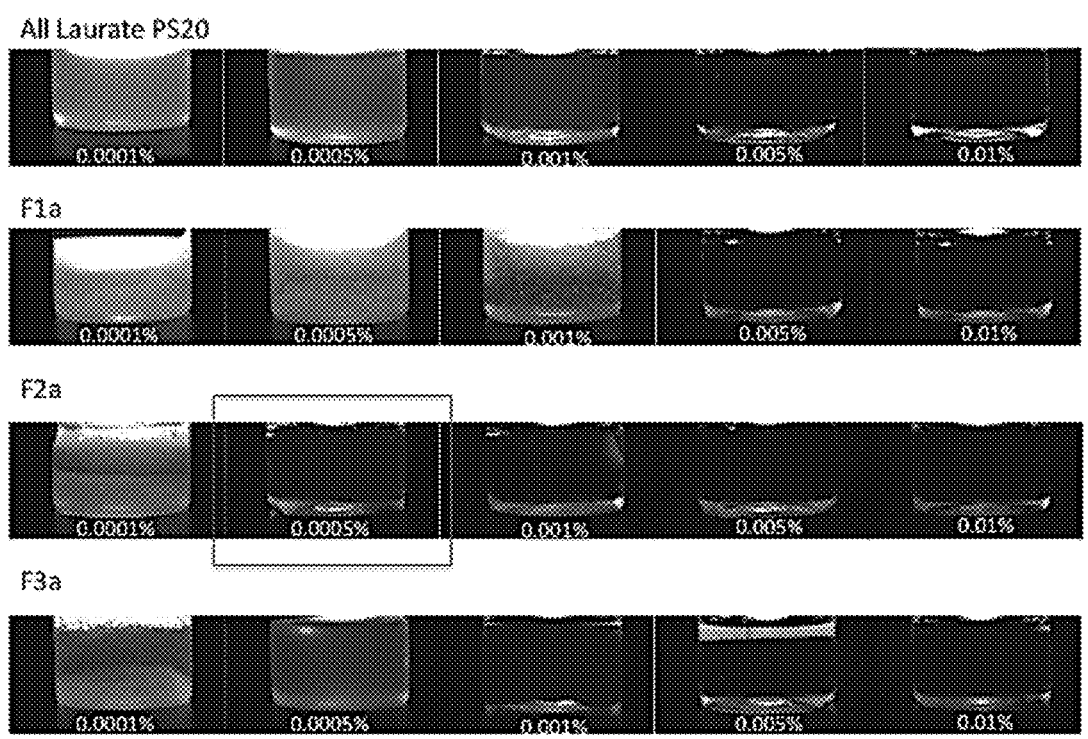
FIG. 5 shows images of antibody formulations containing polysorbate 20 fractions at various concentrations.

During the agitation study, it was observed that F2a required the lowest concentration to be protective from visible particle formation upon agitation, with F1a requiring the most. F3a and the all laurate PS20 produced similar results (FIG. 5). Although F2a had a higher CMC and comparable equilibrium surface tension impact to F3a and all laurate PS20, it was the most protective of the mAb against agitation stress and particle formation.

Example 6 IV Bag Agitation Model Study

The purified fractions were tested for their ability to prevent surface induced aggregation through the use of an agitation study. mAb B and mAb C were diluted to 0.5 mg/mL with a buffer in 0.9% saline with varying amounts of each of the PS20 fractions (F1a, F2a, and F3a from 0.0001% to 0.01%, w/v) in 5 mL PETG vials. The samples were agitated on an orbital shaker at 180 RPM for 2 hours at ambient temperature. Following agitation, the samples were observed using a Bosch APK system with 10× magnification and rotation. The samples were also subjected to HIAC (high accuracy fluid particle counting) to quantify SVPs (sub-visible particles) in the formulations and SEC-HPLC (size exclusion high performance liquid chromatography) to quantify the HMWF (high molecular weight fraction) and the concentration of active antibody in the formulation. SEC and IEC were performed on an Agilent 1260 HPLC with a binary pump and diode array detector. The subvisible particle measurements were performed on a HIAC 9703+ Pharmaceutical Particle Counter from Royco.

Figure 6A:
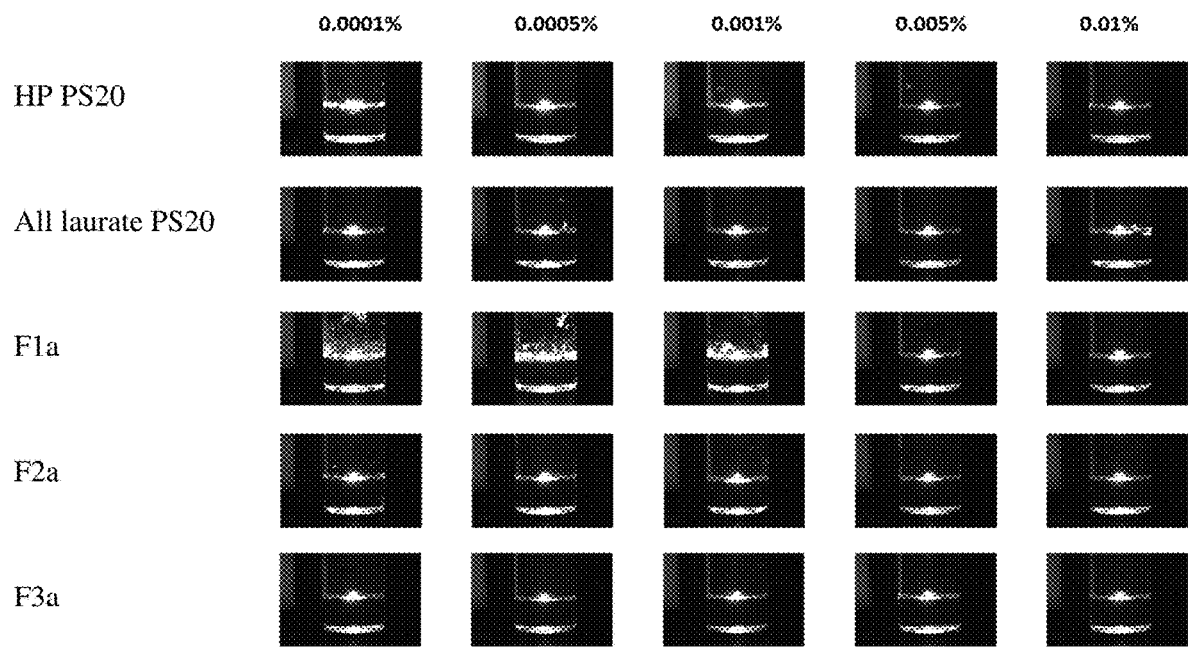
FIG. 6A and FIG. 6B show images of antibody formulations containing polysorbate 20 fractions at various concentrations.
Figure 6B:
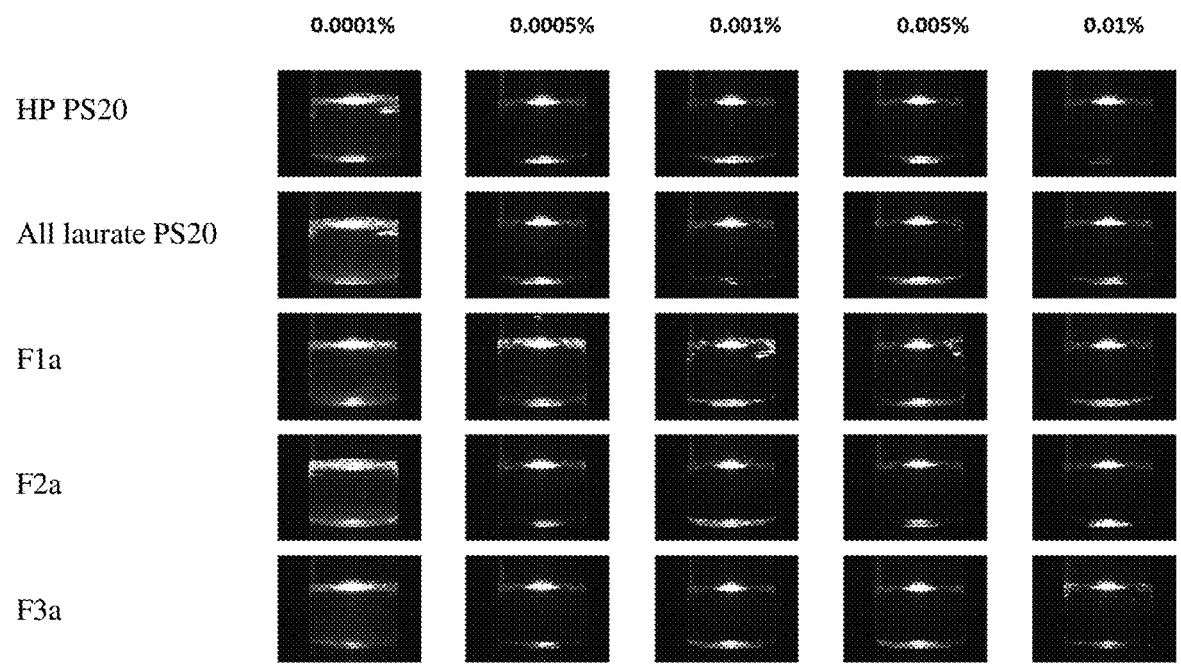
Figure 7A:
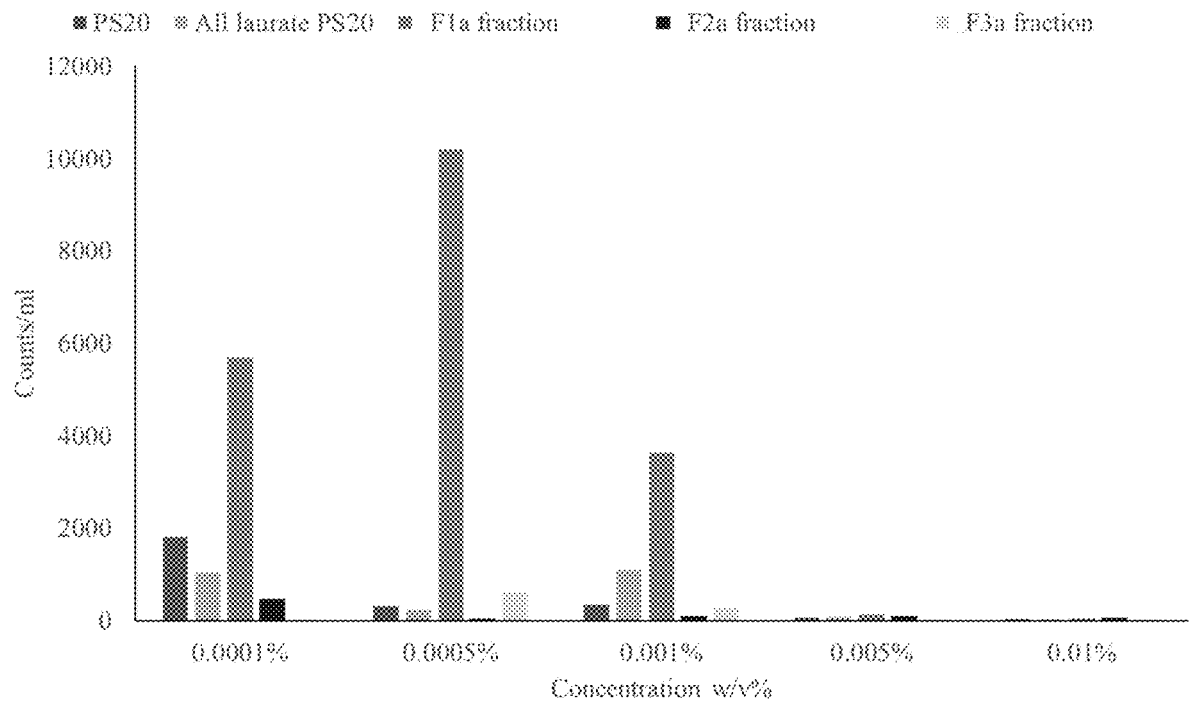
FIG. 7A and FIG. 7B show the results of HIAC for antibody formulations of mAb B and mAB C containing polysorbate 20 fractions at various concentrations.
Figure 7B:
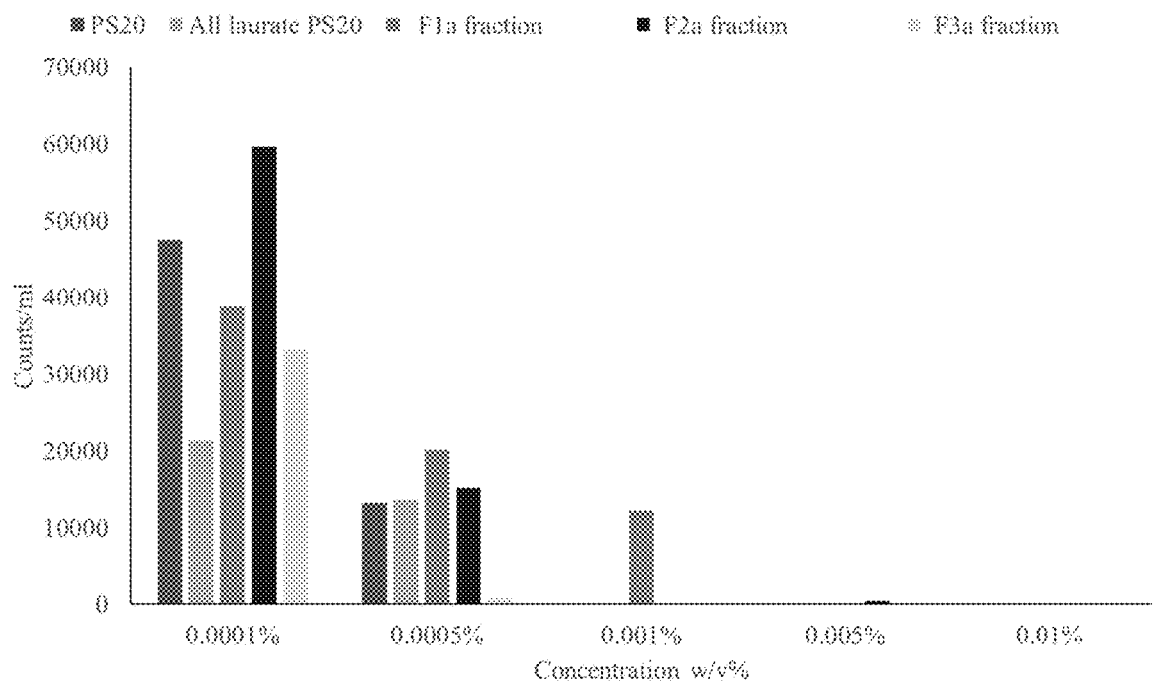
Figure 8A:
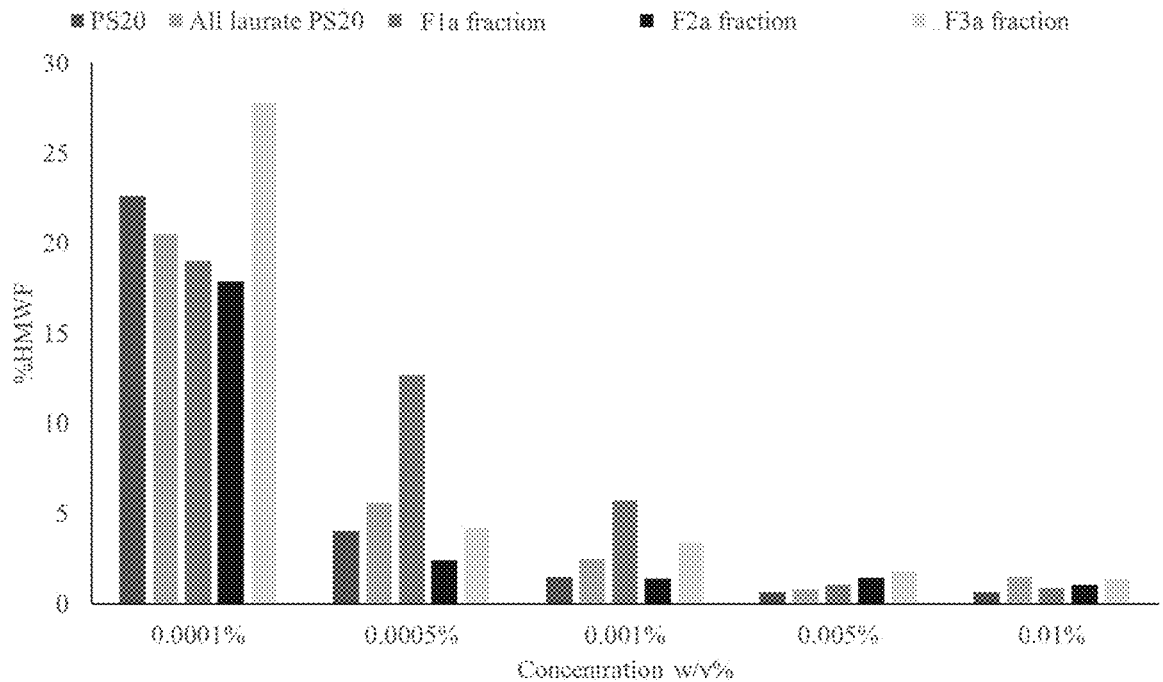
FIG. 8A, FIG. 8B, FIG. 9A, and FIG. 9B show the results of HIAC for antibody formulations of mAB B and mAb C containing polysorbate 20 fractions at various concentrations.
Figure 8B:
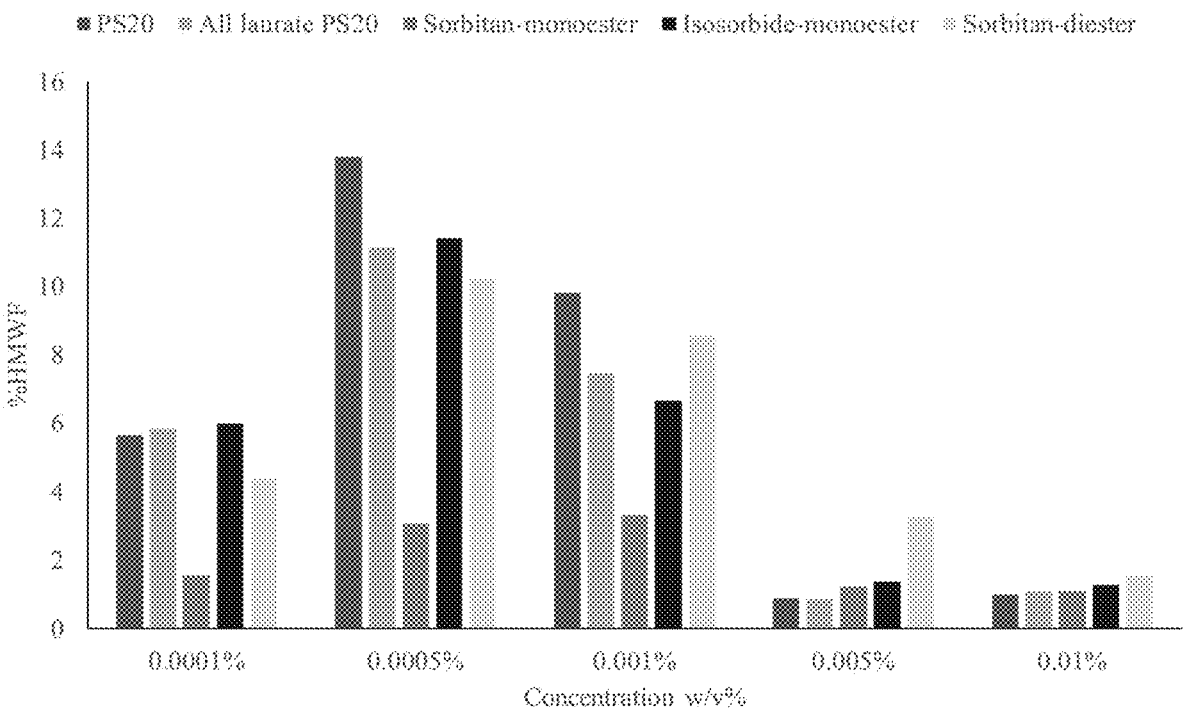
Figure 9A:
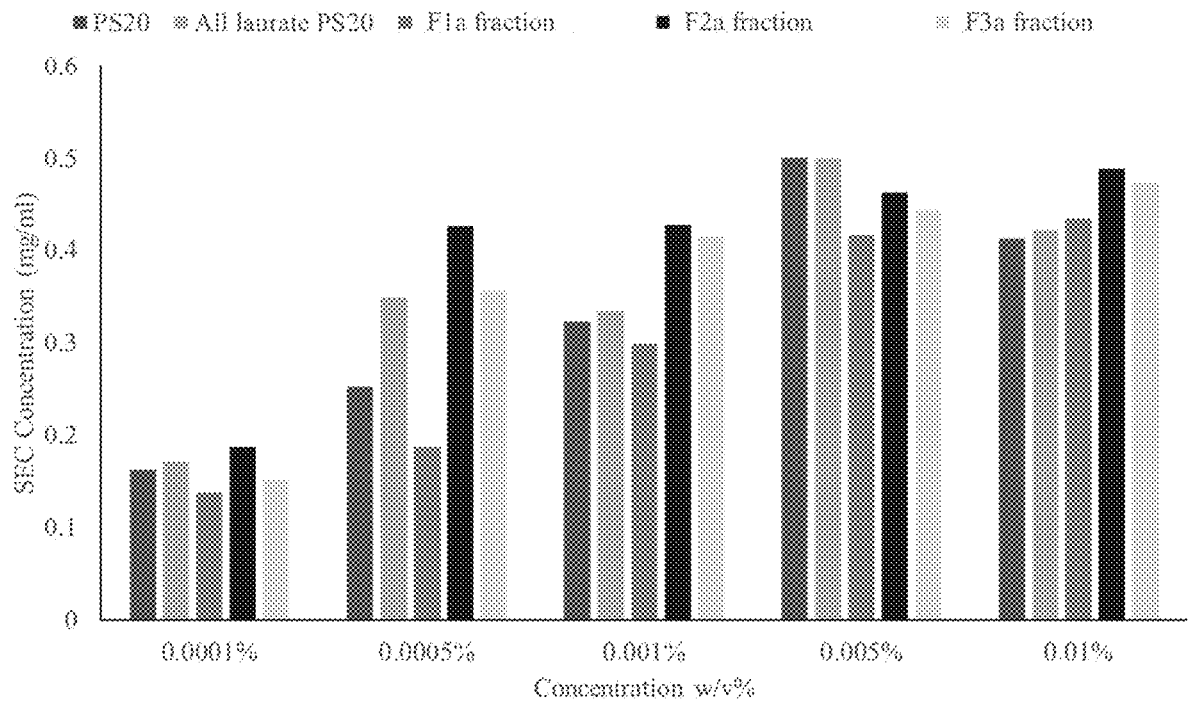
Figure 9B:
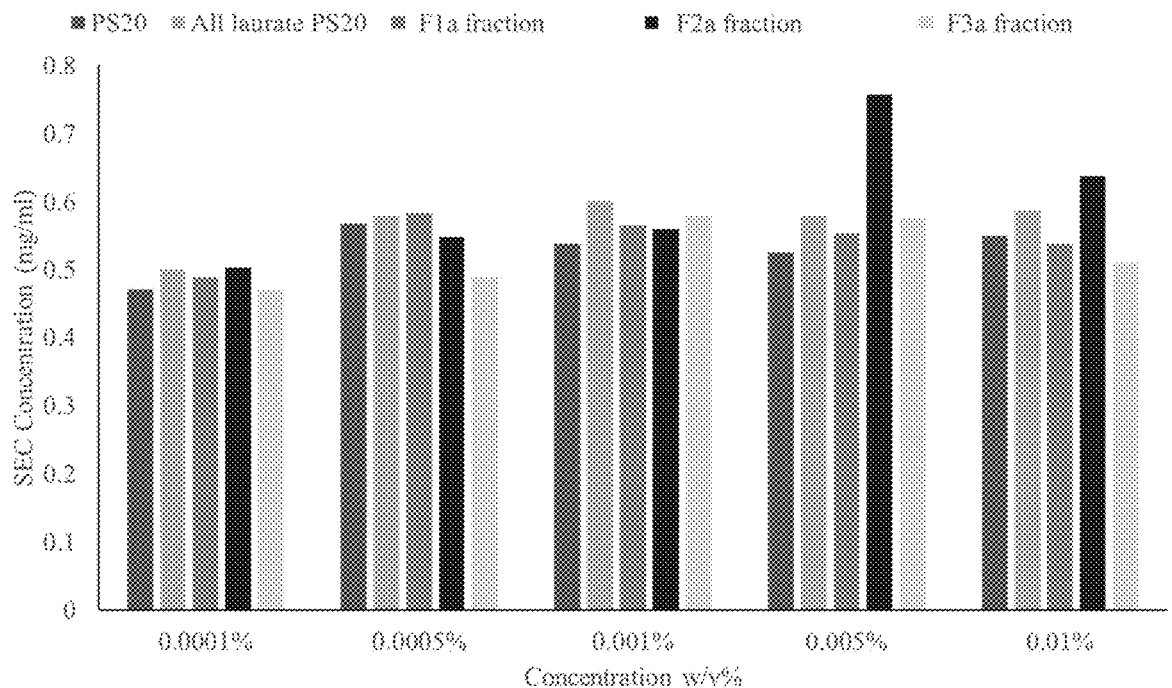

The observation results suggested that the all fractions tested were protective for mAb B (FIG. 6A) and mAb C (FIG. 6B). The results of the HIAC for mAb B (FIG. 7A) and mAb C (FIG. 7B) showed that all fractions were capable of reducing the number of sub-visible particles, indicating a lower level of aggregation. F2a is as good or better than HP or all laurate PS20 at lowering the level of aggregation. The results of the SEC-HPLC assay showed that all fractions lowered the % HMWF (FIG. 8A and FIG. 8B) and better preserved the soluble fractions (FIG. 9A and FIG. 9B) of the antibody formulations of both mAb B (FIG. 8A and FIG. 9A) and mAb C (FIG. 8B and FIG. 9B) during the agitation. F2a is especially effective at lower surfactant concentrations (FIGS. 8A, 8B, 9A, and 9B). All of the surfactants successfully mitigated degradation of the protein.

Example 7 Stability Study

The long-term stability of the formulations was tested for formulations of PS20 and F2a (each at 0.02% w/v) with the proteins mAb C and mAb D (each at 30 mg/mL). The formulations were stored at 5° C., 25° C., and 40° C. and subjected to visual inspection (APK), HIAC, and SEC-HPLC at various intervals. Formulations of PS20 and F2a were also subjected to IEC at 5° C., 25° C., and 40° C.

Figure 10A:
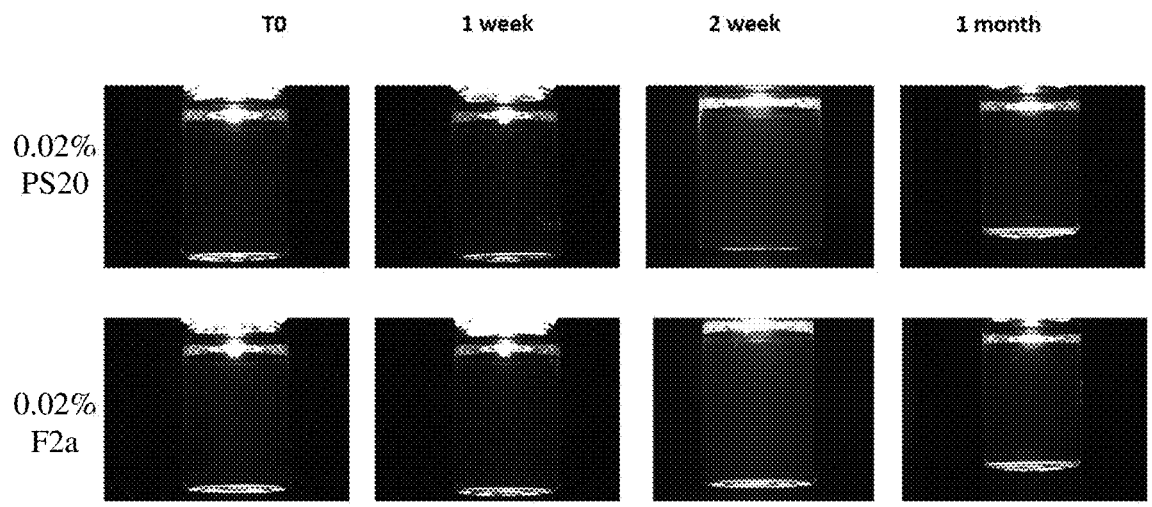
FIG. 10A and FIG. 10B show images of antibody formulations containing polysorbate 20 fractions at various concentrations which were stored at 40° C. for various lengths of time.
Figure 10B:
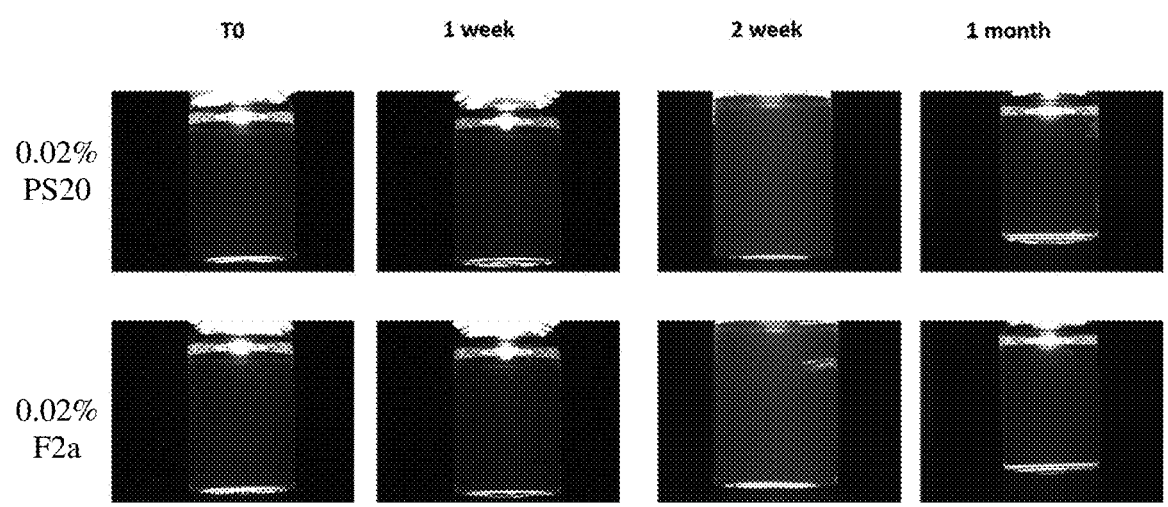

Visual inspection for the formulations stored at 40° C. indicated that both surfactants were effective at limiting particle formation in formulations of both mAb C (FIG. 10A) and mAb D (FIG. 10B) at 40° C. for up to a month.

Figure 11A:
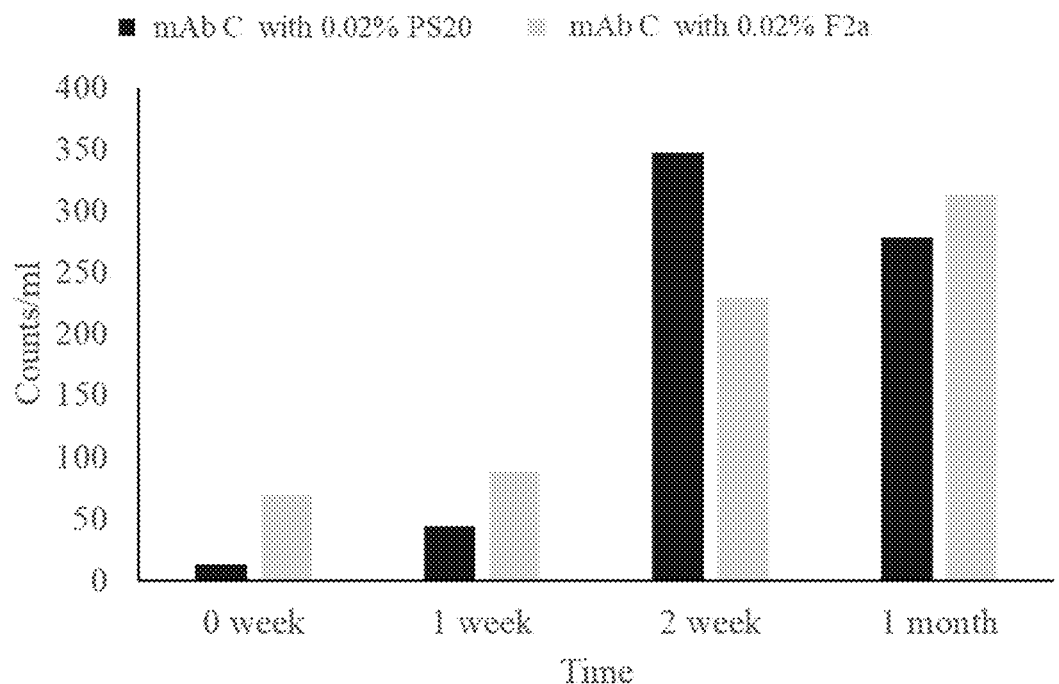
FIG. 11A and FIG. 11B show the results of HIAC for antibody formulations of mAB B and mAb C containing polysorbate 20 fractions at various concentrations stored at 40° C. showed.
Figure 11B:
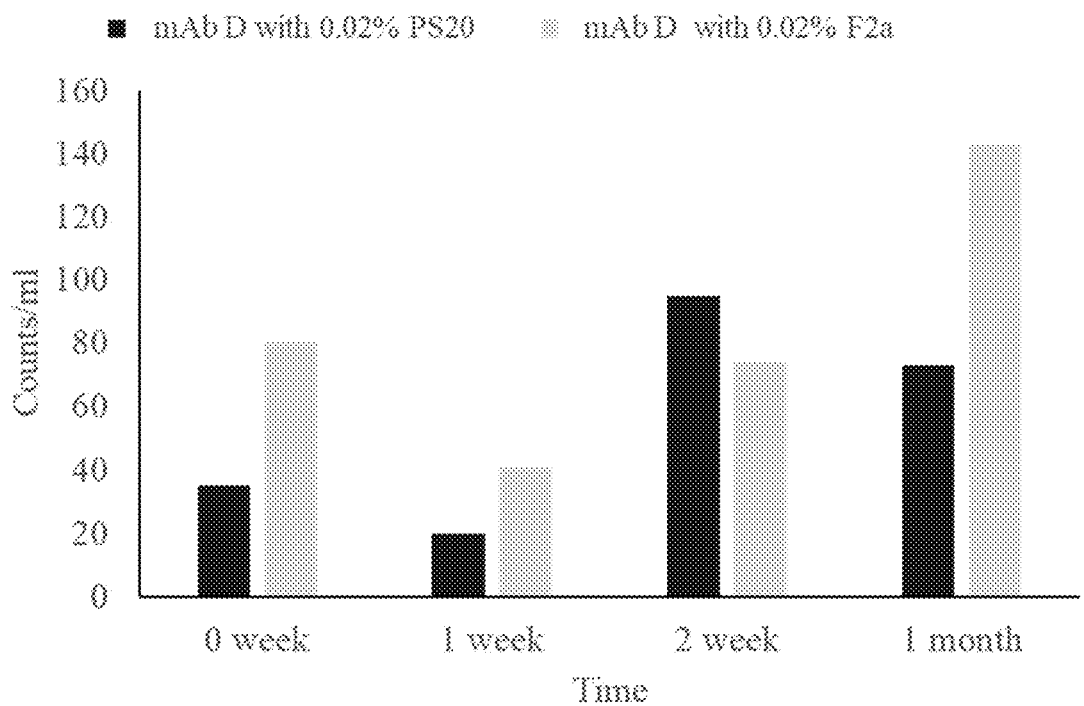

HIAC results for the formulations stored at 40° C. showed that both surfactants were effective at limiting the formation sub-visible particles in formulations of both mAb C (FIG. 11A) and mAb D (FIG. 11B) at 40° C., even when stored for up to a month.

Figure 12A:
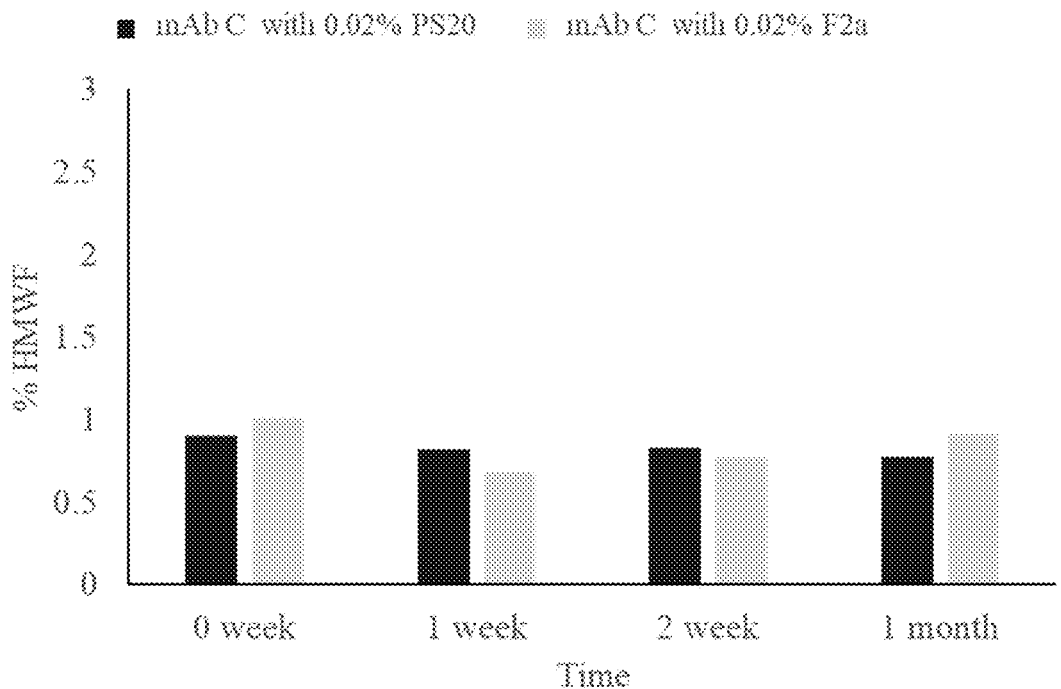
FIG. 12A, FIG. 12B, FIG. 13A, and FIG. 13B show the results of SEC-HPLC for antibody formulations of mAb B and mAb C containing polysorbate 20 fractions at various concentrations stored at 40° C.
Figure 12B:
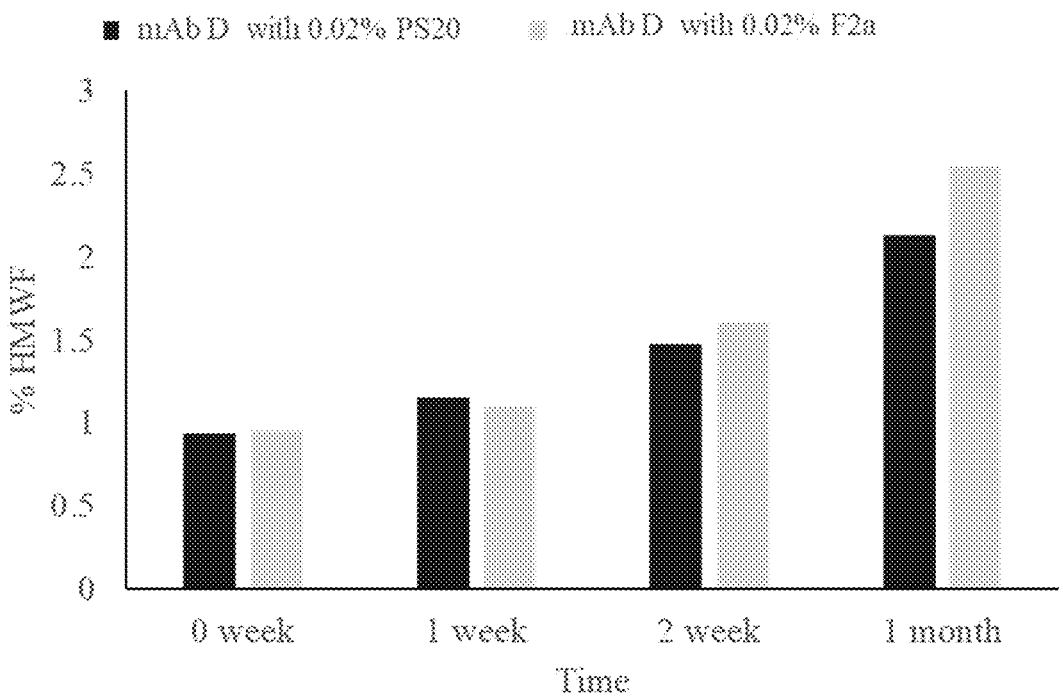
Figure 13A:
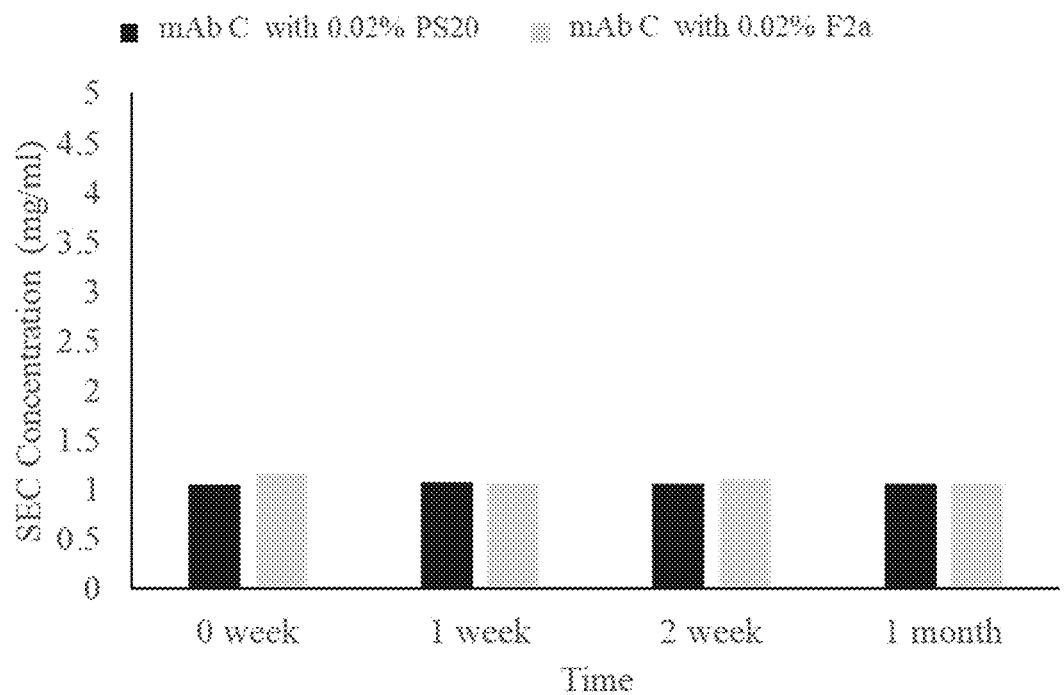
Figure 13B:
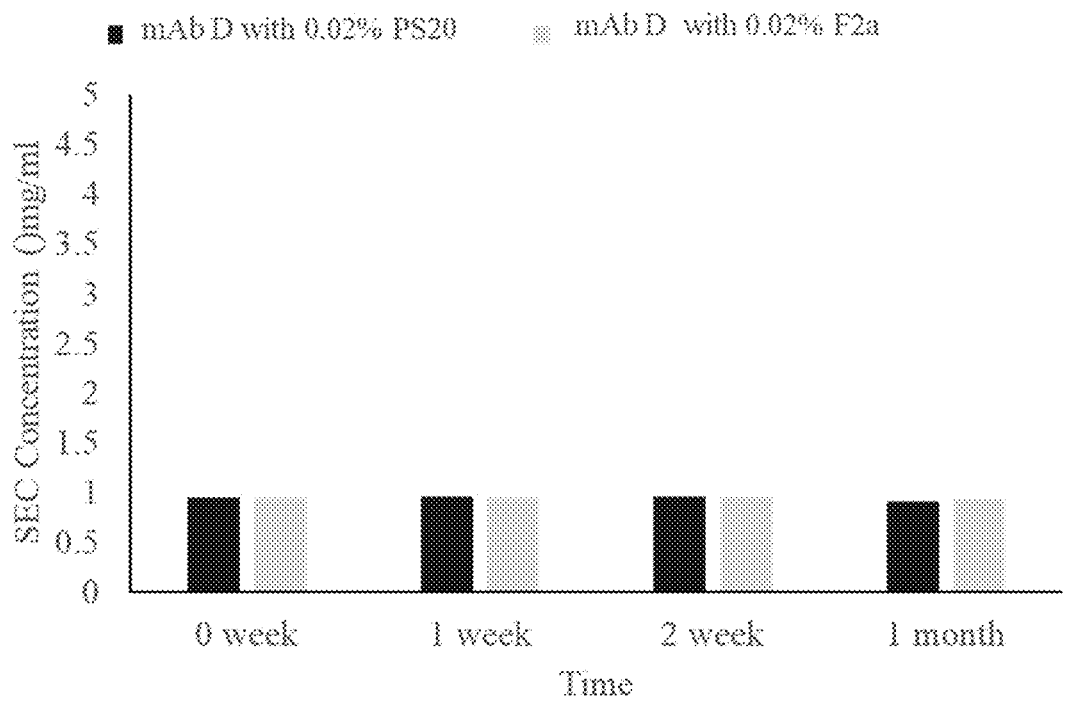

SEC-HPLC results for the formulations stored at 40° C. showed that both surfactants were effective at limiting aggregation in formulations of both mAb C (FIG. 12A) and mAb D (FIG. 12B). SEC results also showed that both surfactants were effective at maintaining active antibody concentration in formulations of both mAb C (FIG. 13A) and mAb D (FIG. 13B) at 40° C. for up to a month.

Figure 14:
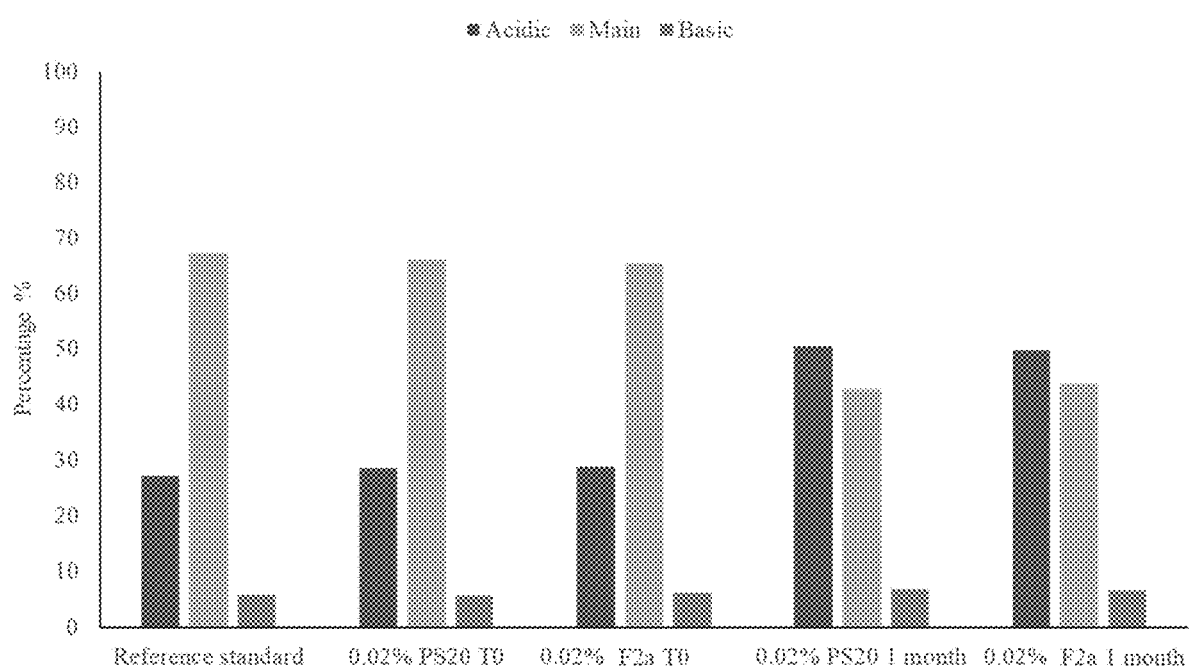
FIG. 14 shows the results of IEC for antibody formulations of mAb B containing polysorbate 20 fractions stored at 40° C.

IEC data for the formulations stored at 40° C. showed that both surfactants limited degradation of mAb C with similar effectiveness for a month (FIG. 14) at 40° C.

Figure 15A:
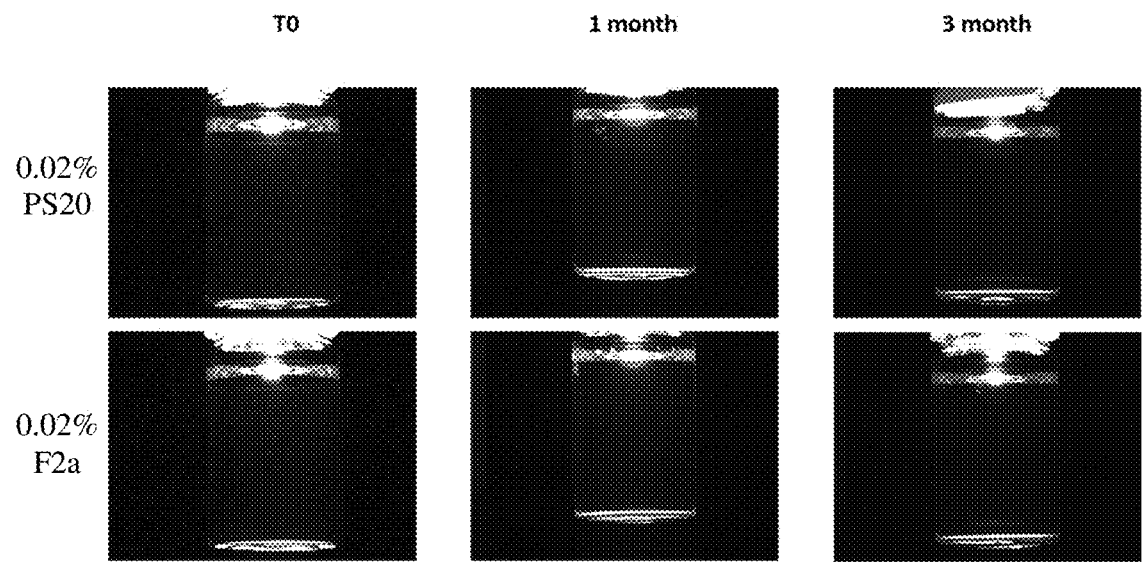
FIG. 15A and FIG. 15B show images of antibody formulations containing polysorbate 20 fractions at various concentrations which were stored at 25° C. for various lengths of time.
Figure 15B:
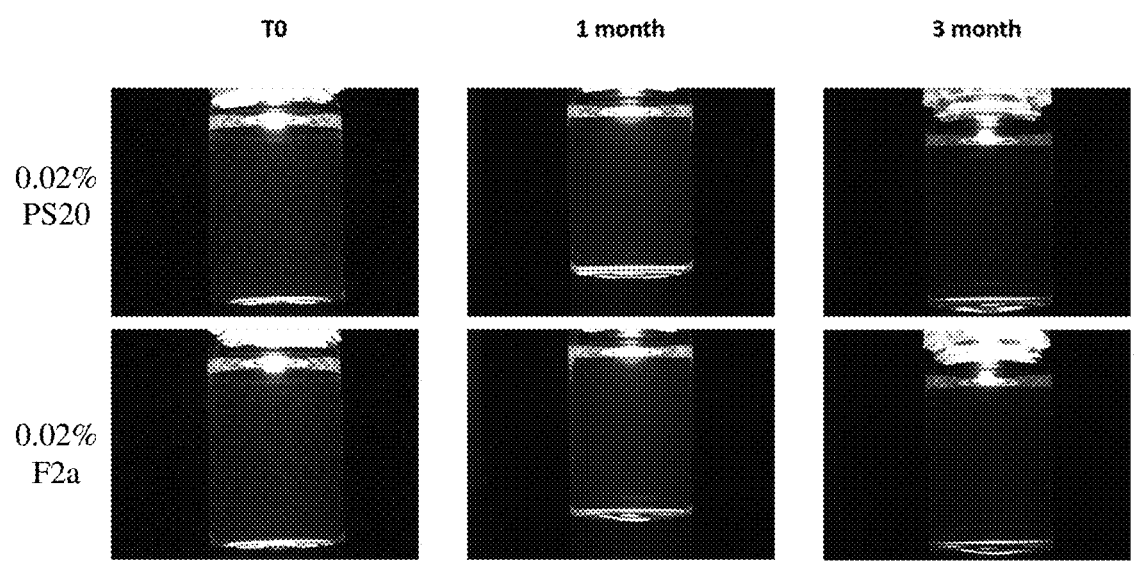

Visual inspection data for the formulations stored at 25° C. showed that both surfactants were effective at limiting aggregation for up to 3 months in formulations of mAb C (FIG. 15A) and mAb D (FIG. 15B).

Figure 16A:
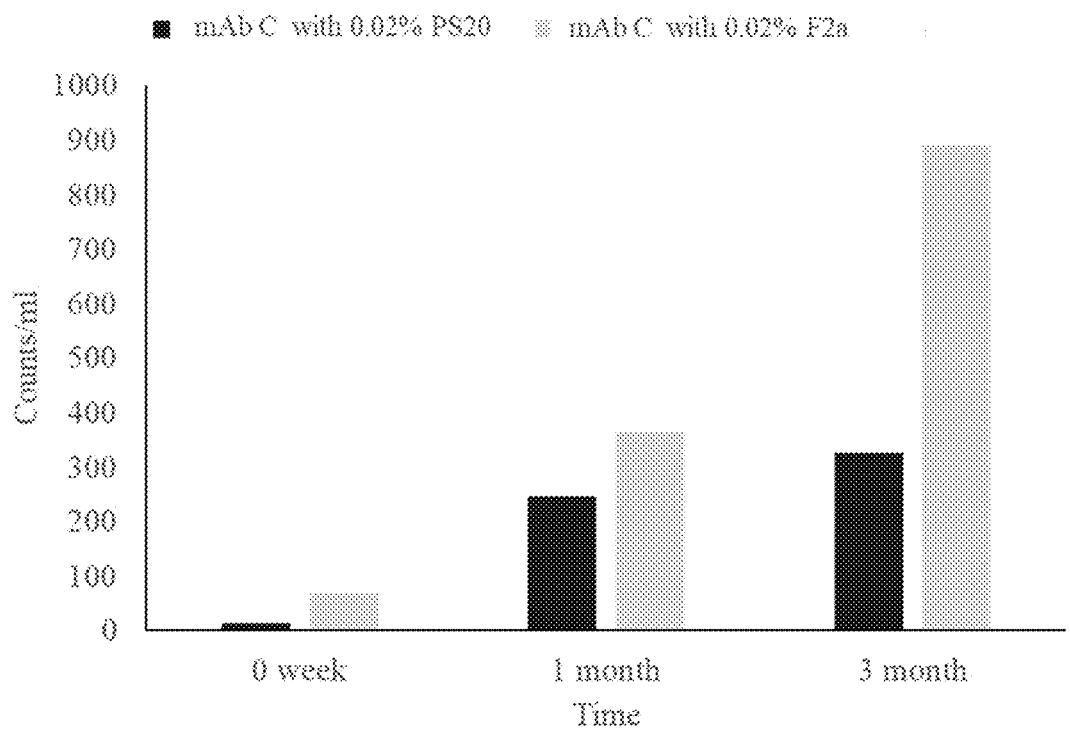
FIG. 16A and FIG. 16B show the results of HIAC for antibody formulations of mAb B and mAb C containing polysorbate 20 fractions at various concentrations stored at 25° C.
Figure 16B:
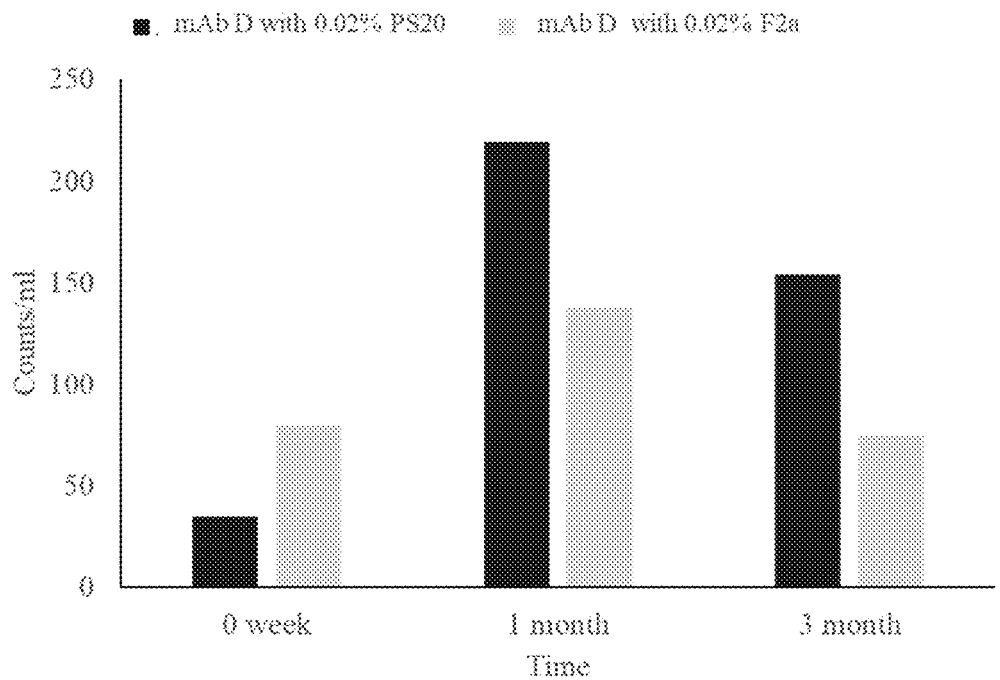

HIAC results for the formulations stored at 25° C. showed that both surfactants were effective at limiting the formation sub-visible particles in formulations of both mAb C (FIG. 16A) and mAb D (FIG. 16B) at 25° C., even when stored for up to 3 months.

Figure 17A:
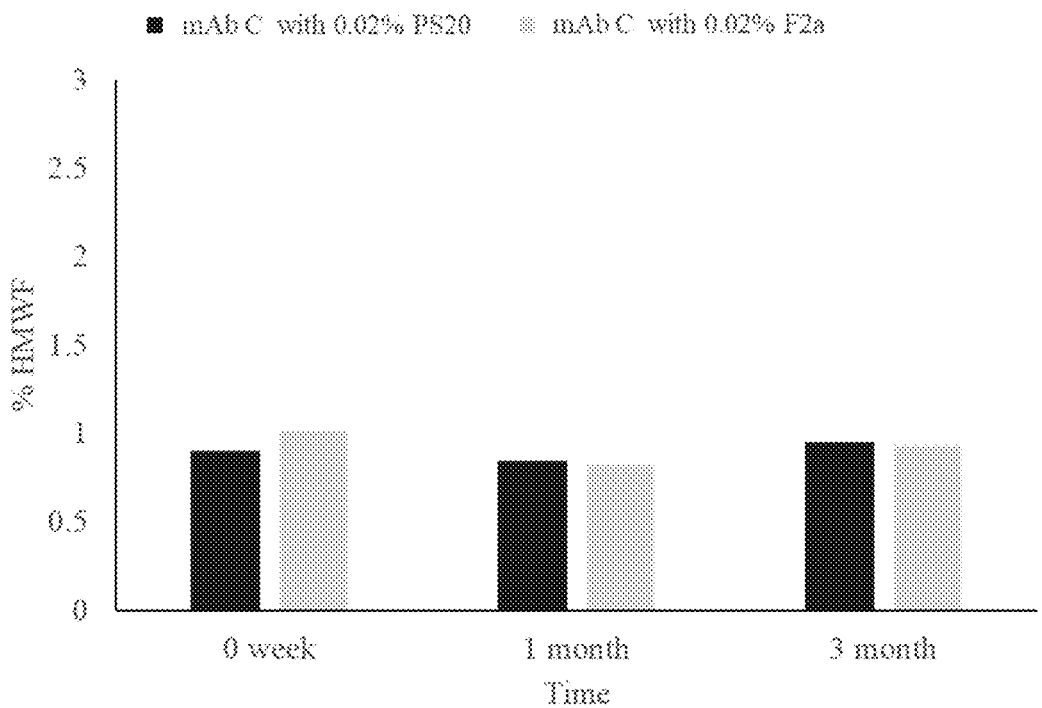
FIG. 17A, FIG. 17B, FIG. 18A, and FIG. 18B show the results of SEC-HPLC for antibody formulations of mAb B and mAb C containing polysorbate 20 fractions at various concentrations stored at 25° C.
Figure 17B:
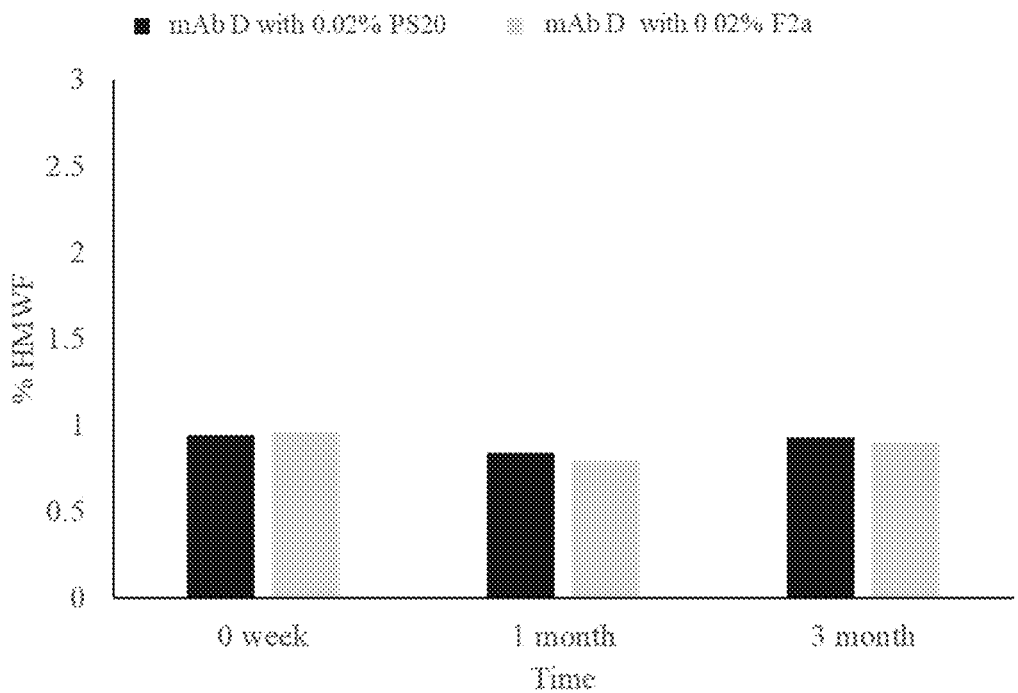
Figure 18A:
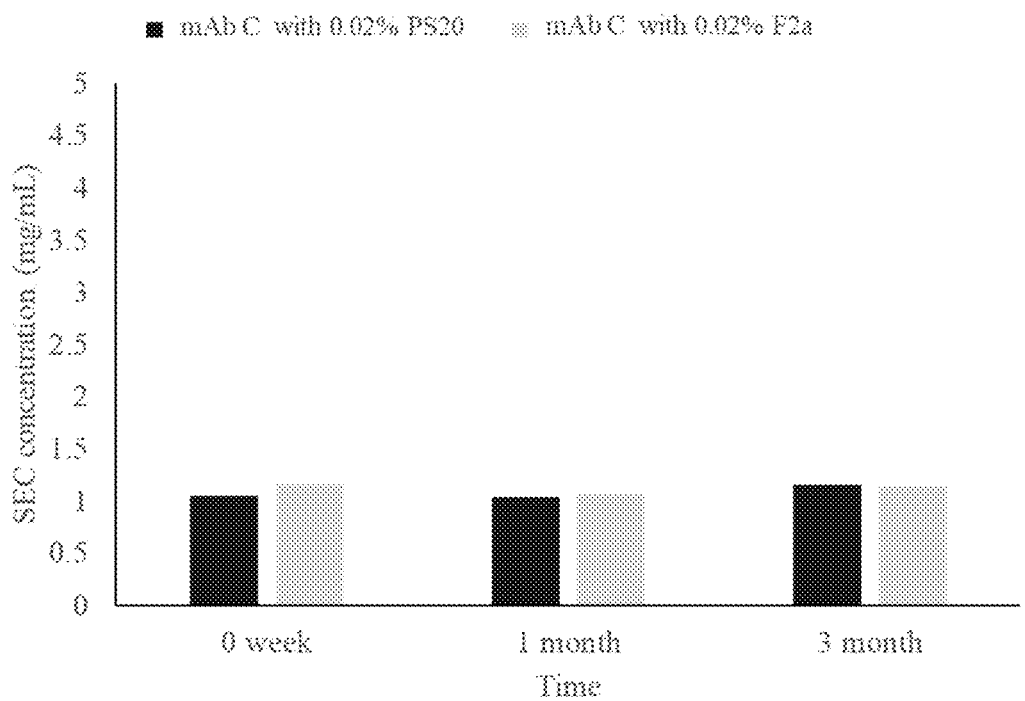
Figure 18B:
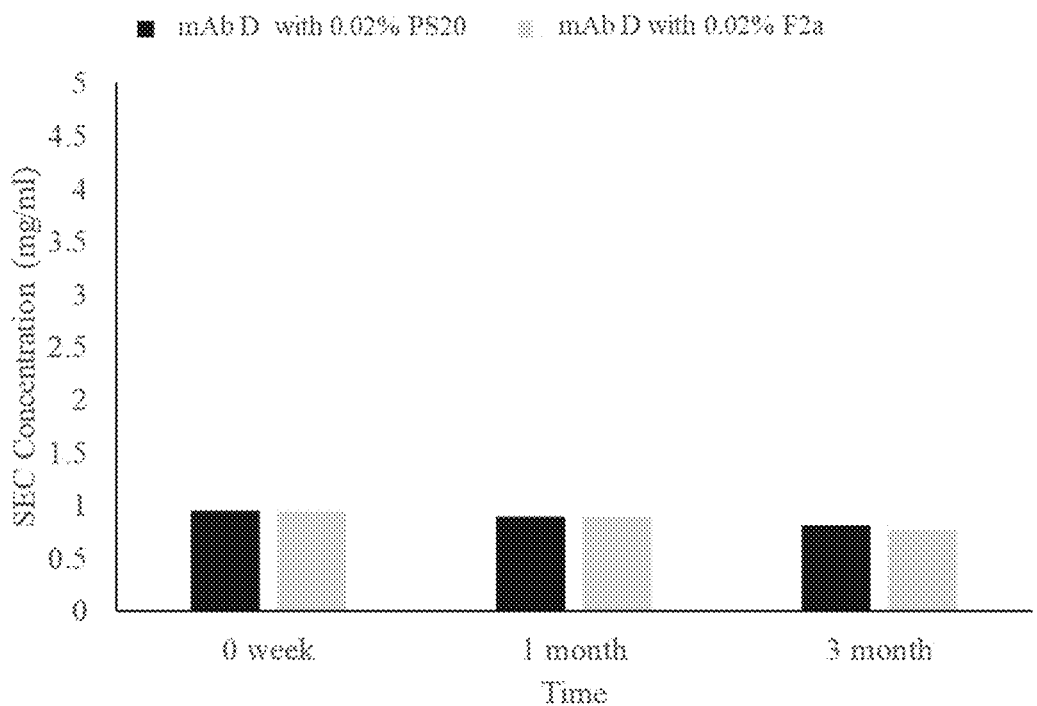

SEC-HPLC results for the formulations stored at 25° C. showed that both surfactants were effective at limiting aggregation in formulations of both mAb C (FIG. 17A) and mAb D (FIG. 17B). SEC results also showed that both surfactants were effective at maintaining active antibody concentration in formulations of both mAb C (FIG. 18A) and mAb D (FIG. 18B) at 25° C. for up to 3 months.

Figure 19:
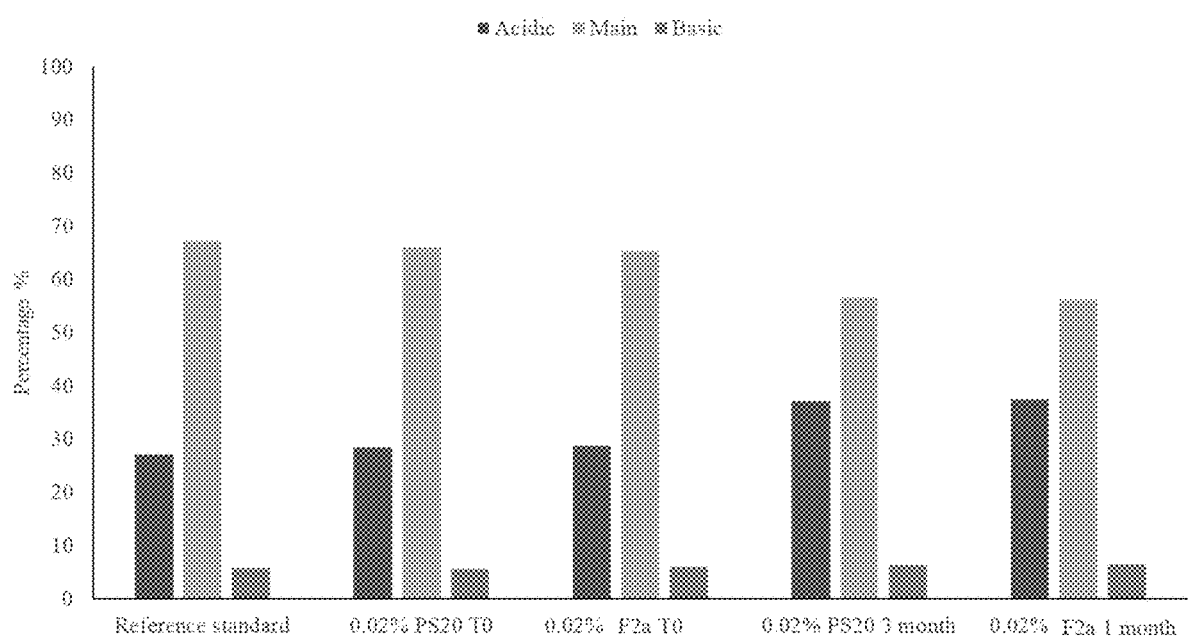
FIG. 19 shows the results of IEC for antibody formulations of mAb B containing polysorbate 20 fractions stored at 25° C.

IEC data for the formulations stored at 25° C. showed that both surfactants limited degradation of mAb C with similar effectiveness for 3 months (FIG. 19) at 25° C.

Figure 20A:
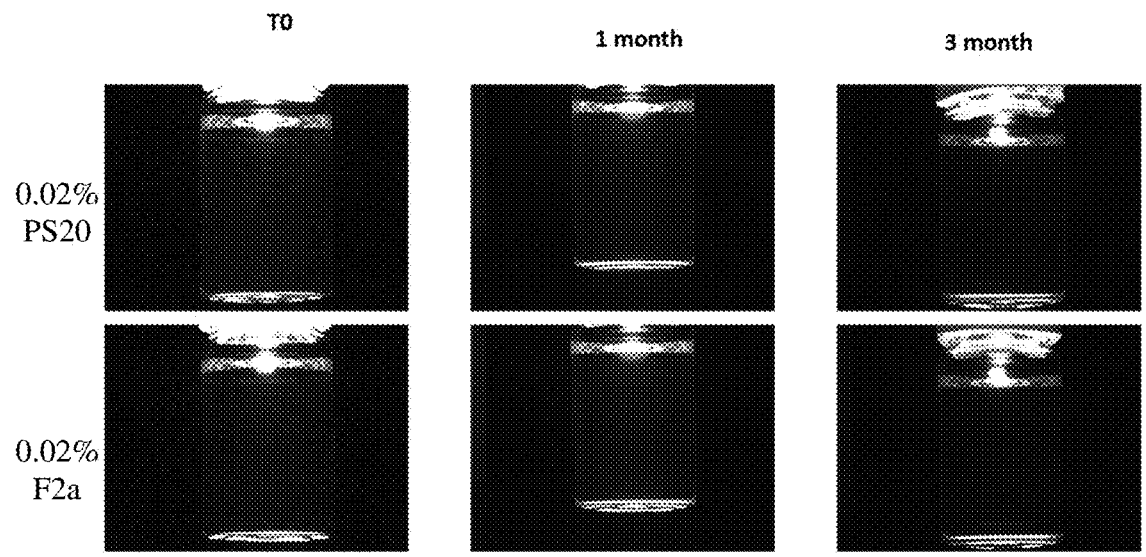
FIG. 20A and FIG. 20B show images of antibody formulations containing polysorbate 20 fractions at various concentrations which were stored at 5° C. for various lengths of time.
Figure 20B:
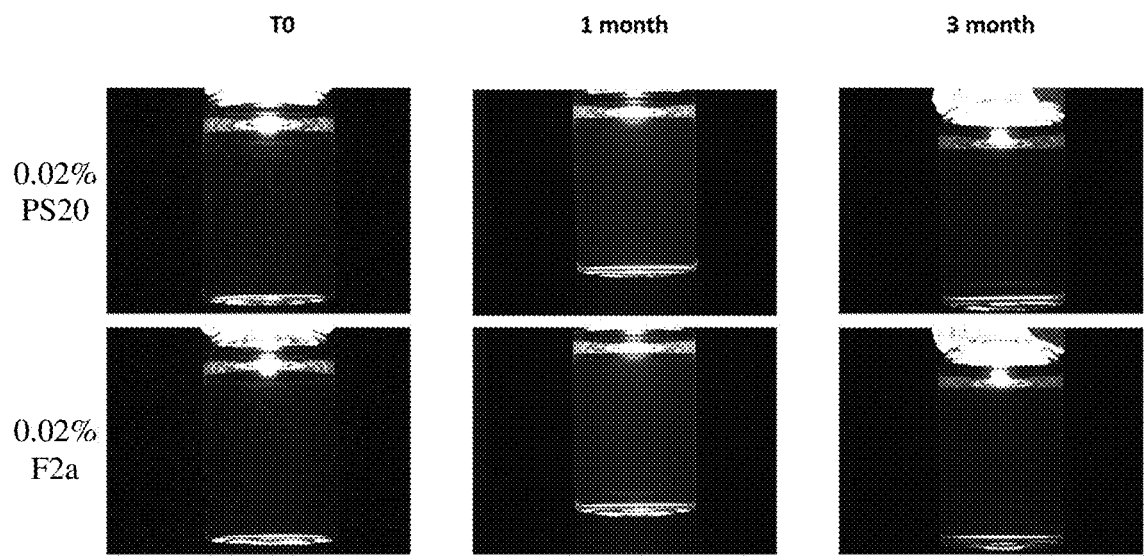

Visual inspection data for the formulations stored at 5° C. showed that both surfactants were effective at preventing aggregation for up to 3 months in formulations of mAb C (FIG. 20A) and mAb D (FIG. 20B).

Figure 21A:
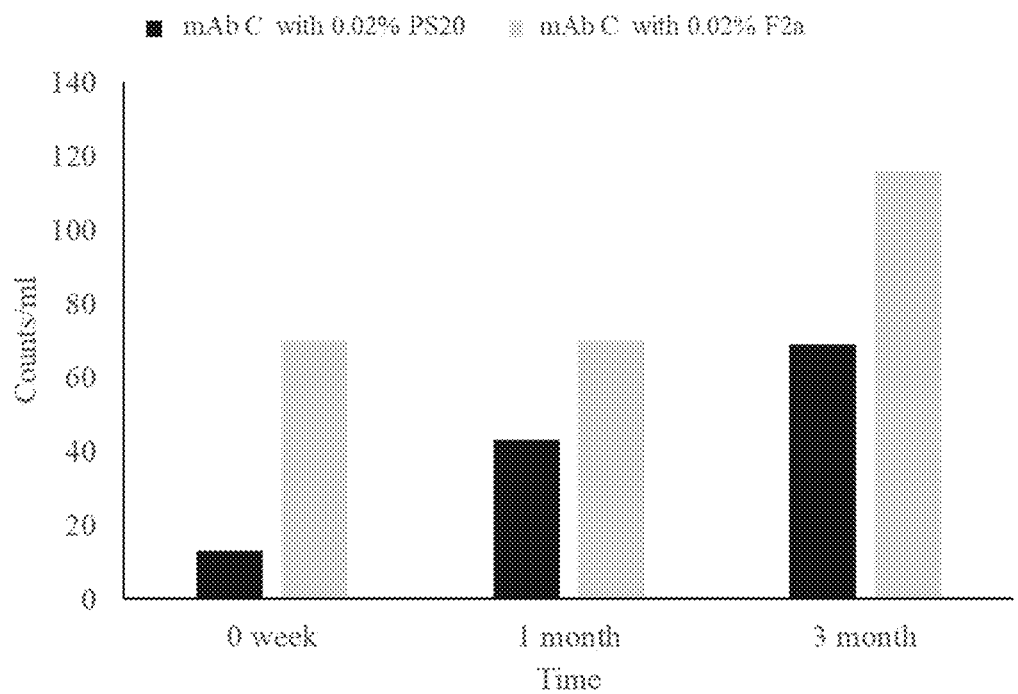
FIG. 21A and FIG. 21B show the results of HIAC for antibody formulations of mAb B and mAb C containing polysorbate 20 fractions at various concentrations stored at 5° C.
Figure 21B:
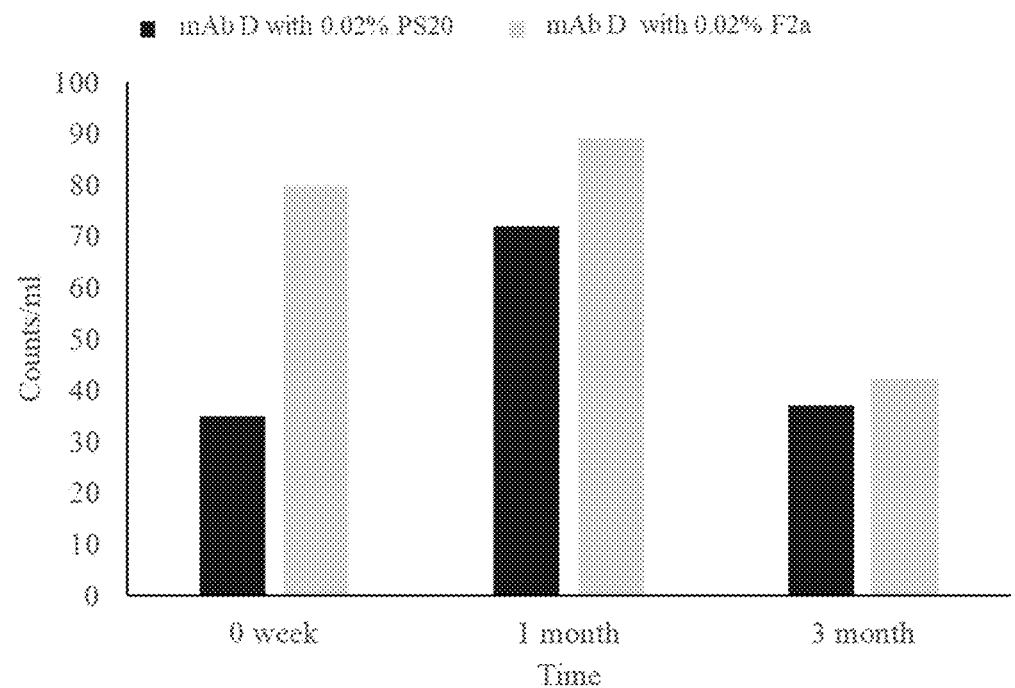

HIAC results for the formulations stored at 5° C. showed that both surfactants were effective at limiting the formation sub-visible particles in formulations of both mAb C (FIG. 21A) and mAb D (FIG. 21B) at 5° C., even when stored for up to 3 months.

Figure 22A:
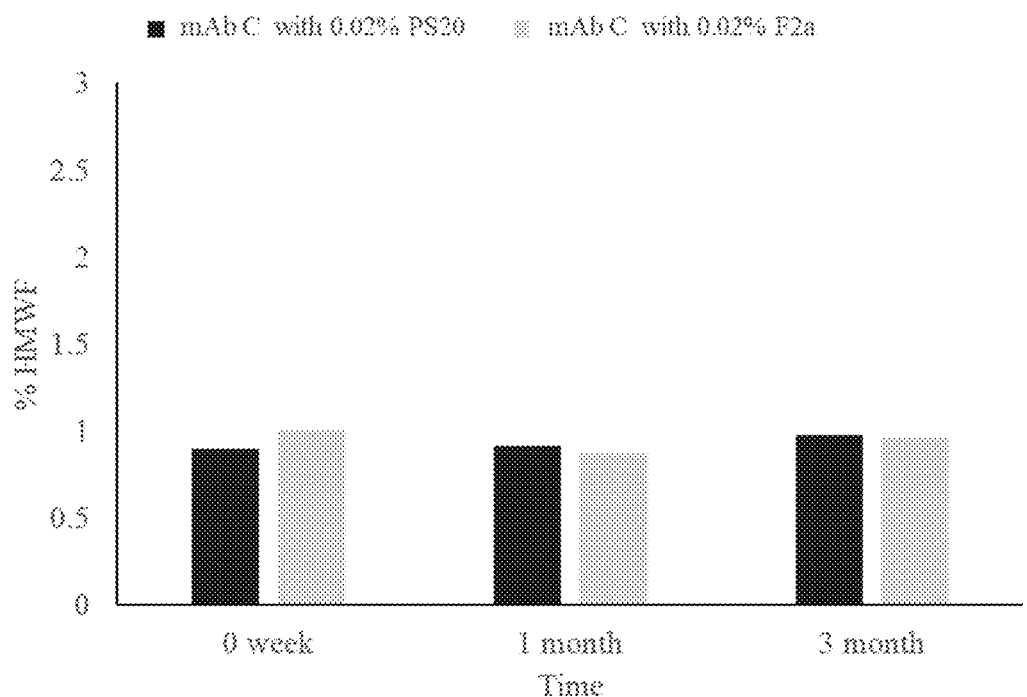
FIG. 22A, FIG. 22B, FIG. 23A, and FIG. 23B show the results of SEC-HPLC for antibody formulations of mAb B and mAb C containing polysorbate 20 fractions at various concentrations stored at 5° C.
Figure 22B:
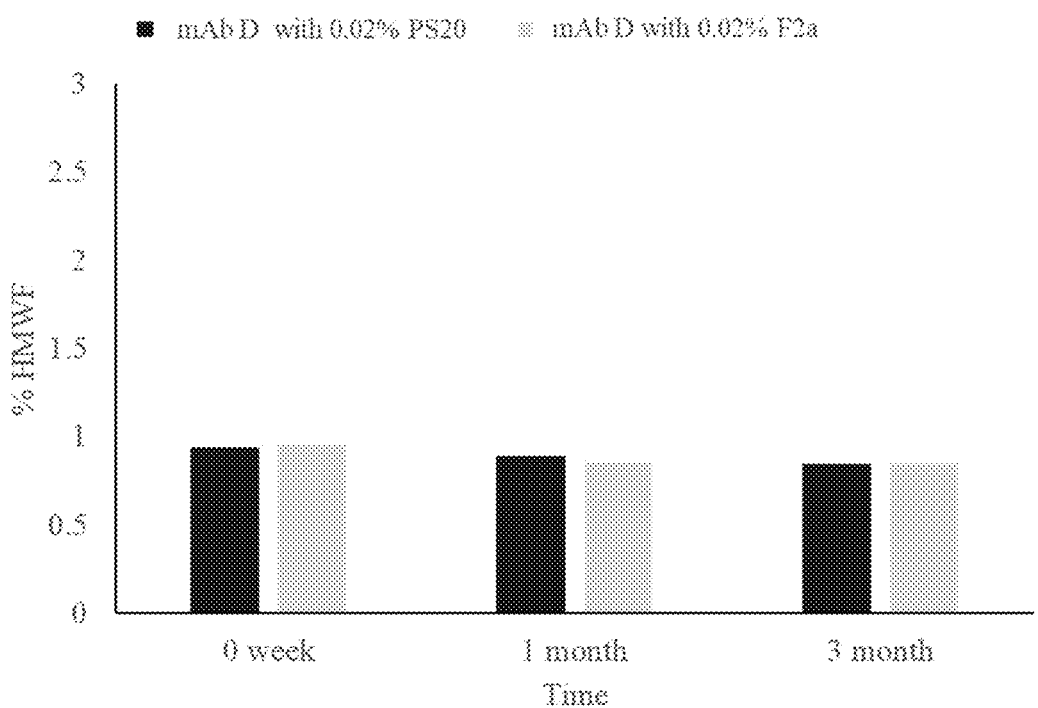
Figure 23A:
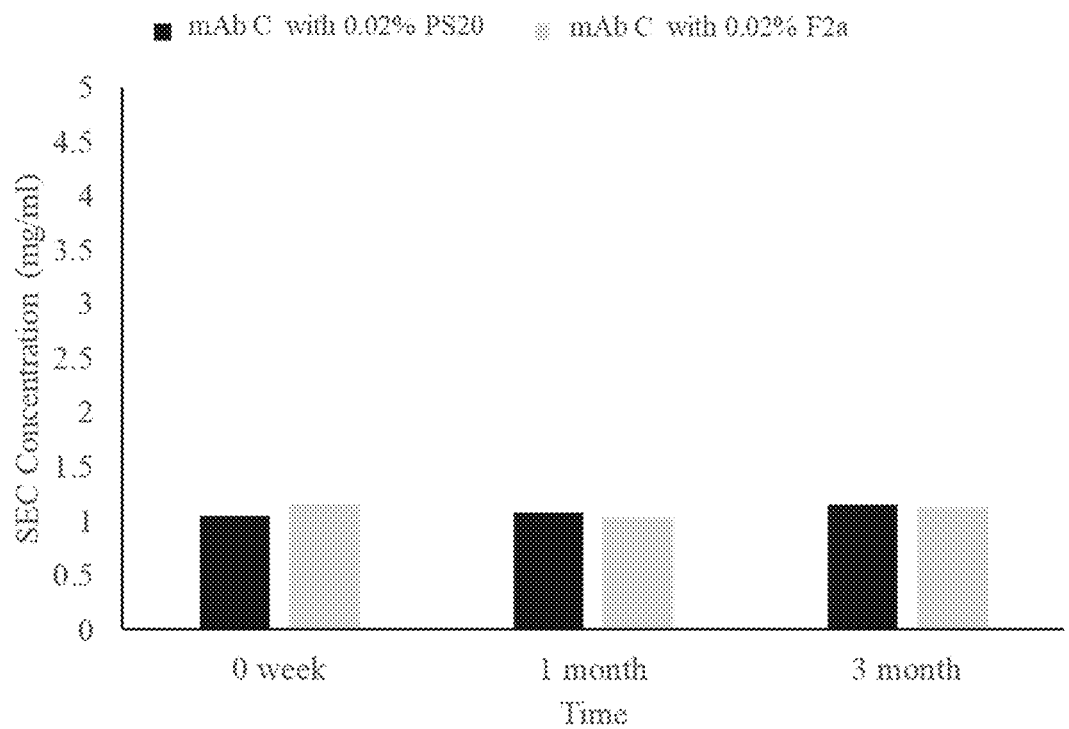
Figure 23B:
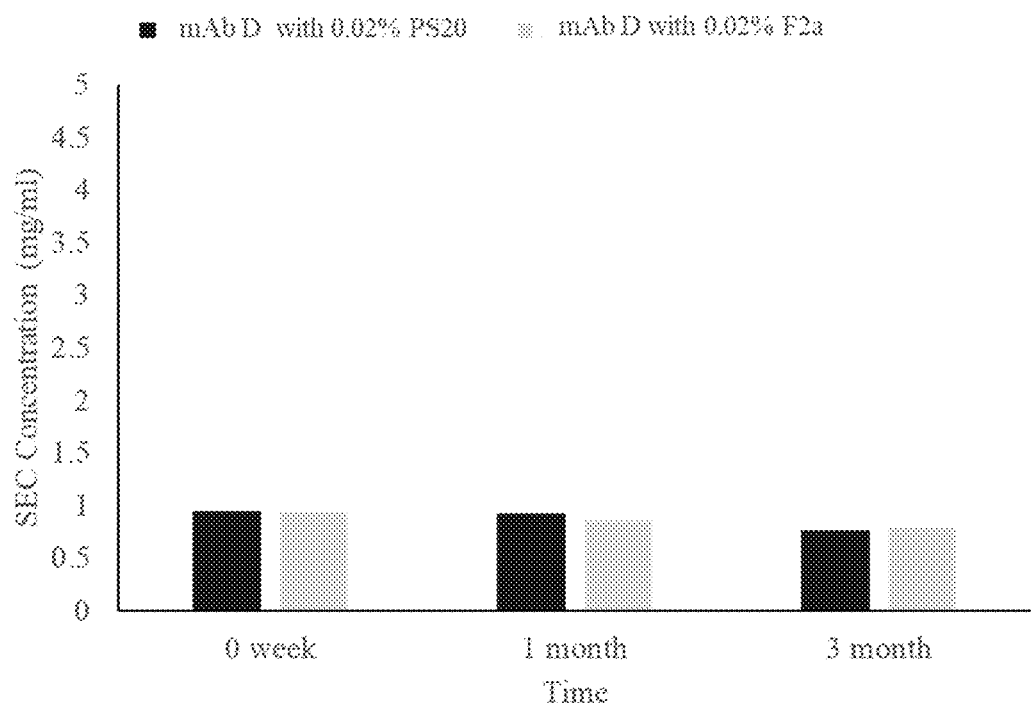

SEC-HPLC results for the formulations stored at 5° C. showed that both surfactants were effective at limiting aggregation in formulations of both mAb C (FIG. 22A) and mAb D (FIG. 22B). SEC results also showed that both surfactants were effective at maintaining active antibody concentration in formulations of both mAb C (FIG. 23A) and mAb D (FIG. 23B) at 5° C. for up to 3 months.

Figure 24:
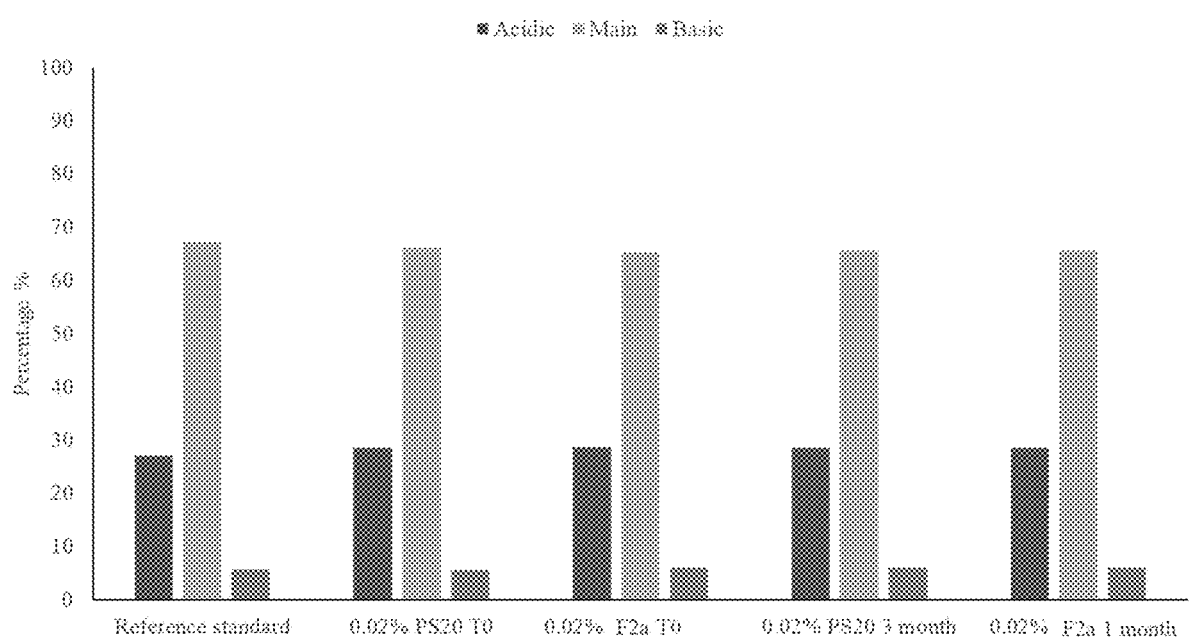
FIG. 24 shows the results of IEC for antibody formulations of mAb B containing polysorbate 20 fractions stored at 5° C.
Figure 25:
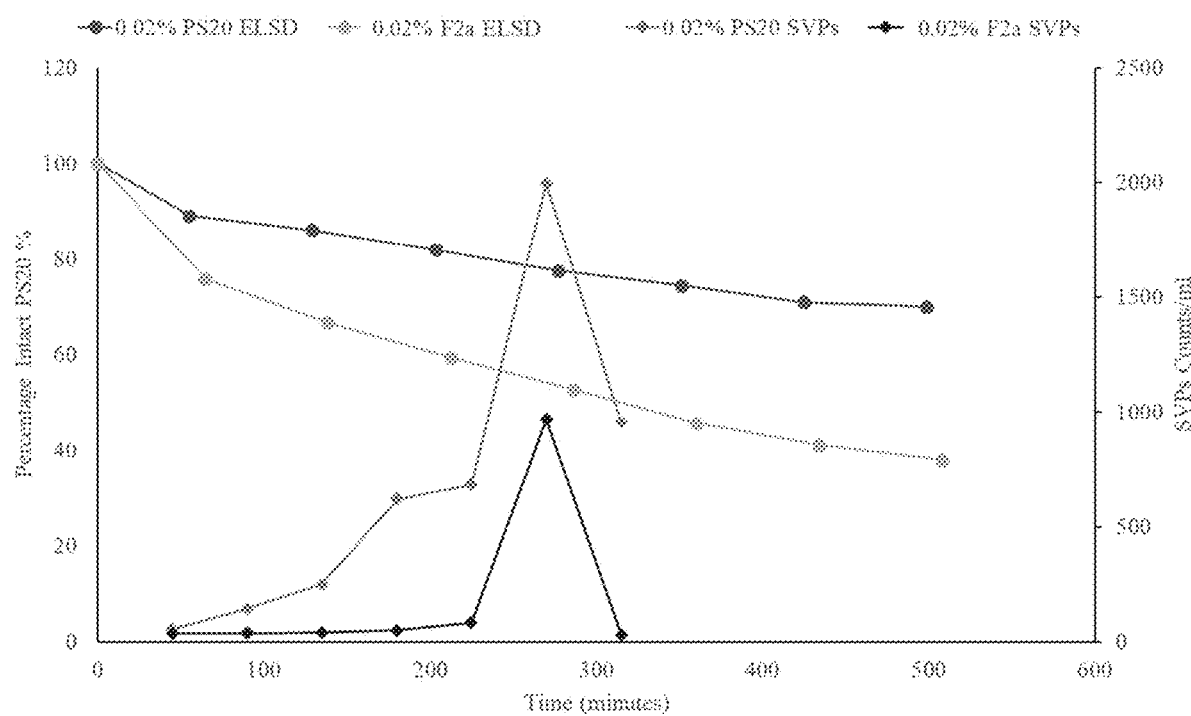
FIG. 25 shows the HIAC results from a forced degradation of PS20 and F2a (each in a formulation buffer at pH=6.0) by a lipase enzyme from *Pseudomonas* Ceoacia (PCL) at a concentration of 2.5 U/mL.

IEC data for the formulations stored at 5° C. showed that both surfactants limited degradation of mAb C with similar effectiveness for 3 months (FIG. 24) at 5° C. Example 8 Forced Degradation Study PS20 and F2a (each in a formulation buffer at pH=6.0) were subjected to forced degradation by a lipase enzyme from *Pseudomonas cepacia* (PCL) at a concentration of 2.5 U/mL. The resulting mixtures were subjected to HIAC to quantify sub-visible particles and the percentage of intact surfactant. The results indicated that F2a produced fewer SVPs despite more degradation by the enzyme (FIG. 25).

SUMMARY

F2a has been shown to be as or more protective for biopharmaceutical products when compared to PS20, a commonly used surfactant excipient. This surfactant has attractive properties which could make it a good alternative to traditional polysorbates like PS20 and PS80.

In agitation stress studies, F2a was found to be more protective from particle formation for mAb A when tested using APK. In a separate study, F2a showed similar protection from agitation stress between F2a and HP PS20 for mAbs B and C based on particle testing by APK, subvisible particle counts by HIAC, % HMWF by SEC-HPLC, and concentration of soluble antibody as tested by SEC-HPLC.

In a stability study, it was observed that F2a was similarly effective to HP PS20 at preventing particle formation by APK and HIAC for two mAbs, mAb C and mAb D. F2a also had similar protection to HP PS20 for prevention of HMWF by SEC-HPLC for both mAb C and mAb D over storage at 5° C., 25° C., and 40° C.

In a forced degradation study, it was shown that F2a could be enzymatically degraded more than HP PS20 before forming subvisible and visible fatty acid particles. This presents an advantage for F2a as a surfactant that would be less prone to this type of fatty acid related particle formation.

What is claimed is:

1. A liquid formulation comprising a polypeptide and a surfactant, wherein at least about 70% (wt %) of the surfactant are isosorbide polyoxyethylene (POE) fatty acid esters.

2. The liquid formulation of claim 1, wherein the isosorbide POE fatty acid esters comprise about 5-30 POE units.

3. The liquid formulation of claim 1, wherein the isosorbide POE fatty acid esters comprise about 20 POE units.

4. The liquid formulation of claim 1, wherein the isosorbide POE fatty acid esters comprise fatty acid chains selected from the group consisting of an optionally substituted $C_{4-28}$ alkyl and an optionally substituted $C_{4-28}$ alkenyl.

5. The liquid formulation of claim 1, wherein the isosorbide POE fatty acid esters are monoesters.

6. The liquid formulation of claim 5, wherein the monoesters are selected from the group consisting of isosorbide POE monolaurate, isorsobide POE monomyristate, isosorbide POE monopalmitate, isosorbide POE monostearate and isosorbide POE monooleate.

7. The liquid formulation of claim 1, wherein the isosorbide POE fatty acid esters are monoesters, diesters, or a mixture of the foregoing.

8. The liquid formulation of claim 1, wherein the isosorbide POE fatty acid ester is a compound of Formula (I):

$$R^1O(CH_2CH_2O)_a\text{-[isosorbide]-}(OCH_2CH_2)_bOR^2; \quad R^3, R^4 \tag{I}$$

wherein:
- a and b are independently integers from 2 to 28, provided that the sum of a and b is an integer from 5-30;
- $R^1$ and $R^2$ are independently selected from the group consisting of hydrogen and —C(O)R", wherein R" is an optionally substituted $C_{3-27}$ alkyl or an optionally substituted $C_{3-27}$ alkenyl; and
- $R^3$ and $R^4$ are independently hydrogen.

9. The liquid formulation of claim 8, wherein the sum of a and b is 9.

10. The liquid formulation of claim 8, wherein $R^1$ is H and $R^2$ is —C(O)R".

11. The liquid formulation of claim 8, wherein $R^1$ is —C(O)R" and $R^2$ is H.

12. The liquid formulation of claim 8, wherein both $R^1$ and $R^2$ are —C(O)R".

13. The liquid formulation of claim 8, wherein R" is an unsubstituted $C_{3-27}$ alkyl.

14. The liquid formulation of claim 13, wherein R" is an unsubstituted $C_{11}$ alkyl.

15. The liquid formulation of claim 8, wherein R" is an unsubstituted $C_{3-27}$ alkenyl.

16. The liquid formulation of claim 15, wherein R" is an unsubstituted $C_{17}$ alkenyl.

17. The liquid formulation of claim 1, wherein at least about 80% (wt %) of the surfactant are isosorbide POE fatty acid esters.

18. The liquid formulation of claim 1, wherein the surfactant further comprises a POE fatty acid ester.

19. The liquid formulation of claim 18, wherein the surfactant comprises a greater amount of isosorbide POE fatty acid esters than POE fatty acid esters.

20. The liquid formulation of claim 18, wherein the POE fatty acid ester comprises a fatty acid chains selected from the group consisting of an optionally substituted $C_{4-28}$ alkyl and an optionally substituted $C_{4-28}$ alkenyl.

21. The liquid formulation of claim 20, wherein the POE fatty acid ester is selected from a group consisting of POE monolaurate, POE monomyristate, POE monopalmitate, POE monostearate, and POE monooleate.

22. The liquid formulation of claim 18, wherein less than about 20% (wt %) of the surfactant are POE fatty acid esters.

23. The liquid formulation of claim 18, wherein the surfactant is about 0.0005% to 0.2% (w:v) of the liquid formulation.

24. The liquid formulation of claim 18, wherein the surfactant further comprises a sorbitan POE fatty acid ester.

25. The liquid formulation of claim 1, wherein the polypeptide is an antibody.

26. The liquid formulation of claim 25, wherein the antibody is selected from the group consisting of a polyclonal antibody, a monoclonal antibody, a humanized antibody, a human antibody, a chimeric antibody, and an antibody fragment.

27. The liquid formulation of claim 26, wherein the antibody fragment is selected from the group consisting of Fab, Fab', F(ab')2, and Fv fragments.

28. The liquid formulation of any one of claims 25-27, wherein the antibody concentration is about 0.1 mg/mL to about 300 mg/mL or about 100 mg/mL to about 300 mg/mL.

29. The liquid formulation of claim 1, wherein the liquid formulation is a reconstituted lyophilized formulation.

30. The liquid formulation of claim 28, wherein the liquid formulation is further diluted with an infusion solution to a polypeptide concentration of about 0.001 mg/mL to about 0.5 mg/mL.

31. The liquid formulation of claim 18, wherein at least about 80% (wt %) of the surfactant are isosorbide polyoxyethylene (POE) fatty acid esters and POE fatty acid esters.

32. The liquid formulation of claim 18, wherein at least about 90% (wt %) of the surfactant are isosorbide polyoxyethylene (POE) fatty acid esters and POE fatty acid esters.

33. A lyophilized formulation comprising a comprising a polypeptide and a surfactant, wherein at least about 70% (wt %) of the surfactant are isosorbide polyoxyethylene (POE) fatty acid esters and POE fatty acid esters; and wherein the lyophilized formulation is prepared by lyophilizing the liquid formulation according to claim 18.

34. An article of manufacture comprising a container enclosing the liquid formulation of claim 1.

35. A method of making a liquid formulation comprising adding a polypeptide and a surfactant to an aqueous solution, wherein at least 70% (wt %) of the surfactant are isosorbide POE fatty acid esters.

* * * * *